(12) United States Patent
Goertzen

(10) Patent No.: US 8,940,002 B2
(45) Date of Patent: Jan. 27, 2015

(54) TISSUE ANCHOR SYSTEM

(75) Inventor: Douglas Goertzen, New Westminster (CA)

(73) Assignee: Kardium Inc., Burnaby, BC (CA)

( * ) Notice: Subject to any disclaimer, the term of this patent is extended or adjusted under 35 U.S.C. 154(b) by 78 days.

(21) Appl. No.: 13/247,380

(22) Filed: Sep. 28, 2011

(65) Prior Publication Data

US 2012/0083806 A1 Apr. 5, 2012

Related U.S. Application Data

(60) Provisional application No. 61/388,405, filed on Sep. 30, 2010.

(51) Int. Cl.
| | |
|---|---|
| *A61B 17/08* | (2006.01) |
| *A61B 17/064* | (2006.01) |
| *A61B 17/04* | (2006.01) |
| *A61B 17/068* | (2006.01) |
| *A61F 2/24* | (2006.01) |

(52) U.S. Cl.
CPC .......... *A61B 17/064* (2013.01); *A61B 17/0401* (2013.01); *A61B 17/068* (2013.01); *A61F 2/2448* (2013.01); *A61F 2/2466* (2013.01); *A61B 17/0644* (2013.01); *A61B 2017/0409* (2013.01); *A61B 2017/0414* (2013.01); *A61B 2017/0437* (2013.01); *A61B 2017/0441* (2013.01); *A61B 2017/0464* (2013.01); *A61B 2017/0645* (2013.01); *A61B 2017/0647* (2013.01); *A61B 2017/0649* (2013.01)
USPC .......................................... 606/151; 604/175

(58) Field of Classification Search
USPC ......... 606/151, 157, 231, 221, 232, 142, 143, 606/158, 213, 219; 623/2.11, 2.36; 604/174, 175
See application file for complete search history.

(56) References Cited

U.S. PATENT DOCUMENTS

| | | | |
|---|---|---|---|
| 566,521 A | 8/1896 | Leger | |
| 3,132,438 A | 5/1964 | Ward et al. | ...................... 43/53.5 |
| 4,041,955 A | 8/1977 | Kelly et al. | |
| 4,085,744 A | 4/1978 | Lewis et al. | |
| 4,114,202 A | 9/1978 | Roy et al. | ........................... 3/1.5 |

(Continued)

FOREIGN PATENT DOCUMENTS

| | | |
|---|---|---|
| EP | 0723467 B1 | 4/2002 |
| EP | 2082690 A1 | 7/2009 |

(Continued)

OTHER PUBLICATIONS

Dahlgren et al., "Medical Device for Constricting Tissue or a Bodily Orifice, for Example a Mitral Valve," Office Action mailed Sep. 13, 2012 for U.S. Appl. No. 12/899,407, 10 pages.

(Continued)

*Primary Examiner* — Elizabeth Houston
*Assistant Examiner* — Robert Lynch
(74) *Attorney, Agent, or Firm* — Rossi, Kimms & McDowell LLP

(57) ABSTRACT

A tissue anchor system includes a plurality of elongated members pivotally coupled by a pivot member and at least one coupler coupled to at least one of the elongated members between a pivot point and an end of the elongated member which coupler is operable to secure the elongated members in a configuration that securely couples the tissue anchor to tissue.

23 Claims, 61 Drawing Sheets

(56) References Cited

U.S. PATENT DOCUMENTS

| | | | |
|---|---|---|---|
| 4,164,046 A | 8/1979 | Cooley | 3/1.5 |
| 4,225,148 A | 9/1980 | Anderson | |
| 4,240,441 A | 12/1980 | Khalil | 128/692 |
| 4,261,342 A | 4/1981 | Aranguren Duo | 128/1 R |
| 4,263,680 A | 4/1981 | Reul et al. | 3/1.5 |
| 4,273,128 A | 6/1981 | Lary | |
| 4,411,266 A | 10/1983 | Cosman | |
| 4,490,859 A | 1/1985 | Black et al. | 3/1.5 |
| 4,527,554 A | 7/1985 | Klein | |
| 4,543,090 A | 9/1985 | McCoy | 604/95 |
| 4,699,147 A | 10/1987 | Chilson et al. | |
| 4,770,187 A | 9/1988 | Lash et al. | |
| 4,794,912 A | 1/1989 | Lia | 128/4 |
| 4,850,957 A | 7/1989 | Summers | 604/22 |
| 4,887,613 A | 12/1989 | Farr et al. | |
| 4,890,602 A | 1/1990 | Hake | 128/4 |
| 4,890,612 A | 1/1990 | Kensey | 606/213 |
| 4,893,613 A | 1/1990 | Hake | 128/4 |
| 4,895,166 A | 1/1990 | Farr et al. | |
| 4,921,499 A | 5/1990 | Hoffman et al. | 623/16 |
| 4,942,788 A | 7/1990 | Farr et al. | |
| 4,979,514 A | 12/1990 | Sekii et al. | |
| 4,994,698 A | 2/1991 | Kliman et al. | |
| 4,998,933 A | 3/1991 | Eggers et al. | |
| 5,021,059 A | 6/1991 | Kensey et al. | 606/213 |
| 5,026,384 A | 6/1991 | Farr et al. | |
| 5,039,894 A | 8/1991 | Teter et al. | |
| 5,047,047 A | 9/1991 | Yoon | 606/216 |
| 5,100,418 A | 3/1992 | Yoon et al. | 606/139 |
| 5,104,399 A | 4/1992 | Lazarus | 623/1 |
| 5,122,137 A | 6/1992 | Lennox | 606/40 |
| 5,127,902 A | 7/1992 | Fischell | |
| 5,156,151 A | 10/1992 | Imran | |
| 5,156,609 A | 10/1992 | Nakao et al. | 606/142 |
| 5,174,299 A | 12/1992 | Nelson | |
| 5,176,693 A | 1/1993 | Pannek, Jr. | |
| 5,178,620 A | 1/1993 | Eggers et al. | |
| 5,192,291 A | 3/1993 | Pannek, Jr. | |
| 5,192,314 A | 3/1993 | Daskalakis | 623/3 |
| 5,201,316 A | 4/1993 | Pomeranz et al. | |
| 5,228,442 A | 7/1993 | Imran | |
| 5,242,386 A | 9/1993 | Holzer | |
| 5,242,456 A * | 9/1993 | Nash et al. | 606/142 |
| 5,245,987 A | 9/1993 | Redmond et al. | |
| 5,258,000 A | 11/1993 | Gianturco | 606/151 |
| 5,279,299 A | 1/1994 | Imran | |
| 5,293,869 A | 3/1994 | Edwards et al. | |
| 5,312,435 A | 5/1994 | Nash et al. | 606/213 |
| 5,312,439 A | 5/1994 | Loeb | |
| 5,317,952 A | 6/1994 | Immega | |
| 5,320,632 A | 6/1994 | Heidmueller | 606/144 |
| 5,341,807 A | 8/1994 | Nardella | |
| 5,364,408 A | 11/1994 | Gordon | 606/144 |
| 5,366,443 A | 11/1994 | Eggers et al. | 604/114 |
| 5,366,459 A | 11/1994 | Yoon | 606/151 |
| 5,368,601 A | 11/1994 | Sauer et al. | 606/144 |
| 5,374,275 A | 12/1994 | Bradley et al. | 606/144 |
| 5,379,773 A | 1/1995 | Hornsby | |
| RE34,866 E | 2/1995 | Kensey et al. | |
| 5,390,664 A | 2/1995 | Redmond et al. | |
| 5,417,698 A | 5/1995 | Green et al. | |
| 5,419,767 A | 5/1995 | Eggers et al. | |
| 5,423,859 A | 6/1995 | Koyfman et al. | |
| 5,450,860 A | 9/1995 | O'Connor | 128/898 |
| 5,454,834 A | 10/1995 | Boebel et al. | |
| 5,478,353 A | 12/1995 | Yoon | 606/213 |
| 5,496,267 A | 3/1996 | Drasler et al. | |
| 5,507,811 A * | 4/1996 | Koike et al. | 606/151 |
| 5,531,760 A | 7/1996 | Alwafaie | 606/216 |
| 5,557,967 A | 9/1996 | Renger | |
| 5,558,091 A | 9/1996 | Acker et al. | |
| 5,593,424 A | 1/1997 | Northrup, III | 606/232 |
| 5,598,848 A | 2/1997 | Swanson et al. | |
| 5,645,566 A | 7/1997 | Brenneman et al. | |
| 5,662,587 A | 9/1997 | Grundfest et al. | |
| 5,681,308 A | 10/1997 | Edwards et al. | |
| 5,681,336 A | 10/1997 | Clement et al. | |
| 5,687,723 A | 11/1997 | Avitall | |
| 5,690,649 A | 11/1997 | Li | |
| 5,697,285 A | 12/1997 | Nappi et al. | |
| 5,713,896 A | 2/1998 | Nardella | 606/50 |
| 5,716,397 A | 2/1998 | Myers | 623/2 |
| 5,720,726 A | 2/1998 | Marcadis et al. | 604/96 |
| 5,728,114 A | 3/1998 | Evans et al. | 606/148 |
| 5,730,127 A | 3/1998 | Avitall | |
| 5,752,965 A | 5/1998 | Francis et al. | |
| 5,762,066 A | 6/1998 | Law et al. | |
| 5,769,846 A | 6/1998 | Edwards et al. | |
| 5,782,239 A | 7/1998 | Webster, Jr. | |
| 5,782,861 A | 7/1998 | Cragg et al. | 606/216 |
| 5,782,879 A | 7/1998 | Rosborough et al. | |
| 5,800,495 A | 9/1998 | Machek et al. | 607/116 |
| 5,824,066 A | 10/1998 | Gross | 623/2 |
| 5,830,222 A | 11/1998 | Makower | |
| 5,836,990 A | 11/1998 | Li | 607/28 |
| 5,865,791 A | 2/1999 | Whayne et al. | 604/49 |
| 5,871,505 A | 2/1999 | Adams et al. | |
| 5,876,343 A | 3/1999 | Teo | |
| 5,881,727 A | 3/1999 | Edwards | |
| 5,891,136 A | 4/1999 | McGee et al. | |
| 5,904,711 A | 5/1999 | Flom et al. | |
| 5,919,207 A | 7/1999 | Taheri | 606/219 |
| 5,921,924 A | 7/1999 | Avitall | |
| 5,935,075 A | 8/1999 | Casscells et al. | |
| 5,935,079 A | 8/1999 | Swanson et al. | |
| 5,941,251 A | 8/1999 | Panescu et al. | |
| 5,961,440 A | 10/1999 | Schweich, Jr. et al. | 600/16 |
| 5,964,782 A | 10/1999 | Lafontaine et al. | 606/213 |
| 5,971,994 A | 10/1999 | Fritzsch | 606/113 |
| 5,976,174 A | 11/1999 | Ruiz | |
| 5,980,473 A | 11/1999 | Korakianitis et al. | |
| 5,984,950 A | 11/1999 | Cragg et al. | 606/216 |
| 6,001,069 A | 12/1999 | Tachibana et al. | 601/2 |
| 6,024,096 A | 2/2000 | Buckberg | 128/898 |
| 6,063,082 A | 5/2000 | DeVore et al. | |
| 6,074,417 A | 6/2000 | Peredo | 623/2 |
| 6,074,418 A | 6/2000 | Buchanan et al. | 623/2.11 |
| 6,104,944 A | 8/2000 | Martinelli | 600/424 |
| 6,113,610 A | 9/2000 | Poncet | 606/139 |
| 6,123,702 A | 9/2000 | Swanson et al. | |
| 6,132,438 A | 10/2000 | Fleischman et al. | 606/139 |
| 6,138,043 A | 10/2000 | Avitall | |
| 6,142,993 A | 11/2000 | Whayne et al. | |
| 6,156,046 A | 12/2000 | Passafaro et al. | |
| 6,183,496 B1 | 2/2001 | Urbanski | |
| 6,203,554 B1 | 3/2001 | Roberts | 606/144 |
| 6,210,432 B1 | 4/2001 | Solem et al. | 623/1.15 |
| 6,214,032 B1 | 4/2001 | Loeb et al. | |
| 6,217,573 B1 | 4/2001 | Webster | |
| 6,221,103 B1 | 4/2001 | Melvin | 623/3.1 |
| 6,221,104 B1 | 4/2001 | Buckberg et al. | 623/3.1 |
| 6,241,747 B1 | 6/2001 | Ruff | 606/216 |
| 6,248,124 B1 | 6/2001 | Pedros et al. | 606/213 |
| 6,258,258 B1 | 7/2001 | Sartori et al. | 208/263 |
| 6,261,309 B1 | 7/2001 | Urbanski | |
| 6,266,550 B1 | 7/2001 | Selmon et al. | |
| 6,287,321 B1 | 9/2001 | Jang | 606/200 |
| 6,304,769 B1 | 10/2001 | Arenson et al. | 600/424 |
| 6,306,135 B1 | 10/2001 | Ellman et al. | 606/45 |
| 6,308,091 B1 | 10/2001 | Avitall | 600/374 |
| 6,332,864 B1 | 12/2001 | Schweich, Jr. et al. | 600/16 |
| 6,346,105 B1 | 2/2002 | Tu et al. | 606/41 |
| 6,358,258 B1 | 3/2002 | Arcia et al. | 606/139 |
| 6,358,277 B1 | 3/2002 | Duran | 623/2.12 |
| 6,360,749 B1 | 3/2002 | Jayaraman | 128/898 |
| 6,379,366 B1 | 4/2002 | Fleischman et al. | 606/139 |
| 6,383,151 B1 | 5/2002 | Diederich et al. | |
| 6,389,311 B1 | 5/2002 | Whayne et al. | |
| 6,391,048 B1 | 5/2002 | Ginn et al. | 606/213 |
| 6,391,054 B2 | 5/2002 | Carpentier et al. | 623/2.37 |
| 6,402,680 B2 | 6/2002 | Mortier et al. | 600/16 |
| 6,402,781 B1 | 6/2002 | Langberg et al. | 623/2.36 |
| 6,406,420 B1 | 6/2002 | McCarthy et al. | 600/16 |
| 6,409,760 B1 | 6/2002 | Melvin | 623/3.1 |

(56) References Cited

U.S. PATENT DOCUMENTS

| | | |
|---|---|---|
| 6,416,459 B1 | 7/2002 | Haindl .................... 600/37 |
| 6,432,115 B1 | 8/2002 | Mollenauer et al. |
| 6,436,052 B1 | 8/2002 | Nikolic et al. ............ 600/529 |
| 6,450,171 B1 | 9/2002 | Buckberg et al. ......... 128/898 |
| 6,475,223 B1 | 11/2002 | Werp et al. ............... 606/108 |
| 6,485,409 B1 | 11/2002 | Voloshin et al. |
| 6,485,489 B2 | 11/2002 | Teirstein et al. .......... 606/41 |
| 6,506,210 B1 | 1/2003 | Kanner .................... 606/213 |
| 6,514,249 B1 | 2/2003 | Maguire et al. |
| 6,529,756 B1 | 3/2003 | Phan et al. |
| 6,537,198 B1 | 3/2003 | Vidlund et al. ........... 600/16 |
| 6,537,314 B2 | 3/2003 | Langberg et al. ......... 623/2.36 |
| 6,540,670 B1 | 4/2003 | Hirata et al. ............. 600/152 |
| 6,551,312 B2 | 4/2003 | Zhang et al. ............. 606/41 |
| 6,569,160 B1 | 5/2003 | Goldin et al. ............. 606/41 |
| 6,569,198 B1 | 5/2003 | Wilson et al. ............ 623/2.37 |
| 6,575,971 B2 | 6/2003 | Hauck et al. ............. 606/52 |
| 6,589,208 B2 | 7/2003 | Ewers et al. .............. 604/104 |
| 6,626,930 B1 | 9/2003 | Allen et al. ............... 606/213 |
| 6,632,238 B2 | 10/2003 | Ginn et al. ............... 606/213 |
| 6,662,034 B2 | 12/2003 | Segner et al. ............ 600/373 |
| 6,676,685 B2 | 1/2004 | Pedros et al. ............ 606/213 |
| 6,681,773 B1 | 1/2004 | Murphy et al. |
| 6,704,590 B2 | 3/2004 | Haldeman |
| 6,723,038 B1 | 4/2004 | Schroeder et al. ........ 600/16 |
| 6,726,704 B1 | 4/2004 | Loshakove et al. ....... 606/213 |
| 6,726,716 B2 | 4/2004 | Marquez ................... 623/2.36 |
| 6,743,241 B2 | 6/2004 | Kerr ......................... 606/144 |
| 6,749,622 B2 | 6/2004 | McGuckin, Jr. et al. .. 606/213 |
| 6,752,810 B1 | 6/2004 | Gao et al. |
| 6,760,616 B2 | 7/2004 | Hoey et al. ............... 600/547 |
| 6,780,197 B2 | 8/2004 | Roe et al. .................. 606/213 |
| 6,797,001 B2 | 9/2004 | Mathis et al. ............. 623/2.37 |
| 6,800,090 B2 | 10/2004 | Alferness et al. ......... 623/2.36 |
| 6,824,562 B2 | 11/2004 | Mathis et al. ............. 623/2.36 |
| 6,837,886 B2 | 1/2005 | Collins et al. |
| 6,840,957 B2 | 1/2005 | DiMatteo et al. ......... 623/1.24 |
| 6,852,076 B2 | 2/2005 | Nikolic et al. ............ 600/37 |
| 6,855,143 B2 | 2/2005 | Davison et al. ........... 606/41 |
| 6,890,353 B2 | 5/2005 | Cohn et al. ............... 623/2.37 |
| 6,892,091 B1 | 5/2005 | Ben-Haim et al. |
| 6,899,674 B2 | 5/2005 | Viebach et al. ........... 600/152 |
| 6,907,297 B2 | 6/2005 | Wellman et al. |
| 6,908,478 B2 | 6/2005 | Alferness et al. ......... 623/1.11 |
| 6,913,576 B2 | 7/2005 | Bowman |
| 6,918,903 B2 | 7/2005 | Bass |
| 6,926,669 B1 | 8/2005 | Stewart et al. |
| 6,941,171 B2 | 9/2005 | Mann et al. |
| 6,942,657 B2 | 9/2005 | Sinofsky et al. |
| 6,949,122 B2 | 9/2005 | Adams et al. ............. 623/2.36 |
| 6,960,229 B2 | 11/2005 | Mathis et al. ............. 623/2.36 |
| 6,986,775 B2 | 1/2006 | Morales et al. ........... 606/139 |
| 6,989,010 B2 | 1/2006 | Francischelli et al. |
| 6,989,028 B2 | 1/2006 | Lashinski et al. ......... 623/2.37 |
| 6,991,649 B2 | 1/2006 | Sievers ..................... 623/2.23 |
| 6,994,093 B2 | 2/2006 | Murphy et al. ........... 128/898 |
| 6,997,951 B2 | 2/2006 | Solem et al. .............. 623/2.37 |
| 7,001,383 B2 | 2/2006 | Keidar |
| 7,025,776 B1 | 4/2006 | Houser et al. ............ 606/213 |
| 7,050,848 B2 | 5/2006 | Hoey et al. ............... 600/547 |
| 7,052,487 B2 | 5/2006 | Cohn et al. ............... 604/509 |
| 7,068,867 B2 | 6/2006 | Adoram et al. |
| 7,101,395 B2 | 9/2006 | Tremulis et al. .......... 623/2.11 |
| 7,141,019 B2 | 11/2006 | Pearlman |
| 7,144,363 B2 | 12/2006 | Pai et al. ................... 600/167 |
| 7,160,322 B2 | 1/2007 | Gabbay .................... 623/2.36 |
| 7,166,127 B2 | 1/2007 | Spence et al. ............ 623/2.37 |
| 7,177,677 B2 | 2/2007 | Kaula et al. ............... 600/546 |
| 7,186,210 B2 | 3/2007 | Feld et al. ................. 600/16 |
| 7,187,964 B2 | 3/2007 | Khoury |
| 7,189,202 B2 | 3/2007 | Lau et al. .................. 600/37 |
| 7,276,044 B2 | 10/2007 | Ferry et al. |
| 7,279,007 B2 | 10/2007 | Nikolic et al. ............ 623/11.11 |
| 7,280,863 B2 | 10/2007 | Shachar |
| 7,300,435 B2 | 11/2007 | Wham et al. ............. 606/34 |
| 7,303,526 B2 | 12/2007 | Sharkey et al. ........... 600/37 |
| 7,320,665 B2 | 1/2008 | Vijay |
| 7,335,196 B2 | 2/2008 | Swanson et al. |
| 7,374,530 B2 | 5/2008 | Schaller ................... 600/16 |
| 7,399,271 B2 | 7/2008 | Khairkhahan et al. .... 600/16 |
| 7,431,726 B2 | 10/2008 | Spence et al. ............ 606/151 |
| 7,452,325 B2 | 11/2008 | Schaller ................... 600/37 |
| 7,452,375 B2 | 11/2008 | Mathis et al. |
| 7,507,252 B2 | 3/2009 | Lashinski et al. ......... 623/2.37 |
| 7,513,867 B2 | 4/2009 | Lichtenstein |
| 7,582,051 B2 | 9/2009 | Khairkhahan et al. .... 600/16 |
| 7,611,534 B2 | 11/2009 | Kapadia et al. ........... 623/2.17 |
| 7,674,276 B2 | 3/2010 | Stone et al. |
| 7,704,277 B2 | 4/2010 | Zakay et al. .............. 623/2.12 |
| 7,736,388 B2 | 6/2010 | Goldfarb et al. .......... 623/2.11 |
| 7,738,967 B2 | 6/2010 | Salo |
| 7,749,249 B2 | 7/2010 | Gelbart et al. ............ 606/216 |
| 7,837,610 B2 | 11/2010 | Lichtenstein et al. |
| 7,869,854 B2 | 1/2011 | Shachar et al. |
| 7,873,402 B2 | 1/2011 | Shachar |
| 7,887,482 B2 | 2/2011 | Hamada |
| 8,027,714 B2 | 9/2011 | Shachar |
| 8,128,644 B2 | 3/2012 | Carley et al. |
| 8,150,499 B2 | 4/2012 | Gelbart et al. |
| 8,337,524 B2 | 12/2012 | Gelbart et al. |
| 8,449,605 B2 | 5/2013 | Lichtenstein et al. |
| 8,532,746 B2 | 9/2013 | Gelbart et al. |
| 8,672,998 B2 | 3/2014 | Lichtenstein et al. |
| 2001/0003158 A1 | 6/2001 | Kensey et al. ............ 606/213 |
| 2001/0005787 A1 | 6/2001 | Oz et al. ................... 606/142 |
| 2001/0018611 A1 | 8/2001 | Solem et al. .............. 623/2.37 |
| 2001/0020126 A1 | 9/2001 | Swanson et al. .......... 600/407 |
| 2001/0041915 A1 | 11/2001 | Roue et al. ................ 606/225 |
| 2001/0044568 A1 | 11/2001 | Langberg et al. ......... 600/37 |
| 2002/0002329 A1 | 1/2002 | Avitall |
| 2002/0013621 A1 | 1/2002 | Stobie et al. .............. 623/2.11 |
| 2002/0016628 A1 | 2/2002 | Langberg et al. ......... 623/2.36 |
| 2002/0026092 A1 | 2/2002 | Buckberg et al. ......... 600/37 |
| 2002/0055775 A1 | 5/2002 | Carpentier et al. ....... 623/2.17 |
| 2002/0082621 A1 | 6/2002 | Schurr et al. ............. 606/151 |
| 2002/0087156 A1 | 7/2002 | Maguire et al. |
| 2002/0087173 A1 | 7/2002 | Alferness et al. ......... 606/151 |
| 2002/0107478 A1 | 8/2002 | Wendlandt |
| 2002/0107511 A1 | 8/2002 | Collins et al. |
| 2002/0107530 A1 | 8/2002 | Sauer et al. |
| 2002/0111647 A1 | 8/2002 | Khairkhahan et al. .... 606/200 |
| 2002/0115944 A1 | 8/2002 | Mendes et al. ............ 600/594 |
| 2002/0161394 A1 | 10/2002 | Macoviak et al. ......... 606/200 |
| 2002/0161406 A1 | 10/2002 | Silvian |
| 2002/0169359 A1 | 11/2002 | McCarthy et al. ........ 600/16 |
| 2002/0169360 A1 | 11/2002 | Taylor et al. .............. 600/37 |
| 2002/0169504 A1 | 11/2002 | Alferness et al. ......... 623/2.36 |
| 2002/0177782 A1 | 11/2002 | Penner |
| 2002/0183836 A1 | 12/2002 | Liddicoat et al. ......... 623/2.11 |
| 2002/0183841 A1 | 12/2002 | Cohn et al. ............... 623/2.36 |
| 2002/0188170 A1 | 12/2002 | Santamore et al. ....... 600/37 |
| 2002/0198603 A1 | 12/2002 | Buckberg et al. ......... 623/23.71 |
| 2003/0018358 A1 | 1/2003 | Saadat |
| 2003/0023241 A1 | 1/2003 | Drewry et al. |
| 2003/0028202 A1 | 2/2003 | Sancoff et al. |
| 2003/0045896 A1 | 3/2003 | Murphy et al. ........... 606/191 |
| 2003/0050682 A1 | 3/2003 | Sharkey et al. ........... 607/126 |
| 2003/0050685 A1 | 3/2003 | Nikolic et al. ............ 623/1.11 |
| 2003/0050693 A1 | 3/2003 | Quijano et al. |
| 2003/0069570 A1 | 4/2003 | Witzel et al. .............. 606/28 |
| 2003/0069593 A1 | 4/2003 | Tremulis et al. |
| 2003/0069636 A1 | 4/2003 | Solem et al. .............. 623/2.37 |
| 2003/0078465 A1 | 4/2003 | Pai et al. ................... 600/16 |
| 2003/0078652 A1 | 4/2003 | Sutherland |
| 2003/0078671 A1 | 4/2003 | Lesniak et al. ............ 623/23.64 |
| 2003/0083742 A1 | 5/2003 | Spence et al. |
| 2003/0105384 A1 | 6/2003 | Sharkey et al. ........... 600/16 |
| 2003/0105520 A1 | 6/2003 | Alferness et al. ......... 623/2.36 |
| 2003/0109770 A1 | 6/2003 | Sharkey et al. ........... 600/16 |
| 2003/0124480 A1 | 7/2003 | Peacock |
| 2003/0149333 A1 | 8/2003 | Alferness ................. 600/16 |
| 2003/0158570 A1 | 8/2003 | Ferrazzi |
| 2003/0163191 A1 | 8/2003 | Nikolic et al. ............ 623/1.11 |
| 2003/0167055 A1* | 9/2003 | Kolata et al. ............. 606/1 |

(56) References Cited

U.S. PATENT DOCUMENTS

| | | |
|---|---|---|
| 2003/0181819 A1 | 9/2003 | Desai |
| 2003/0208210 A1 | 11/2003 | Dreyfuss et al. |
| 2003/0212453 A1 | 11/2003 | Mathis et al. |
| 2003/0220667 A1 | 11/2003 | van der Burg et al. ........ 606/200 |
| 2003/0229395 A1 | 12/2003 | Cox ............................. 623/2.36 |
| 2004/0002626 A1 | 1/2004 | Feld et al. ...................... 600/37 |
| 2004/0054279 A1 | 3/2004 | Hanley ........................ 600/424 |
| 2004/0122516 A1 | 6/2004 | Fogarty et al. |
| 2004/0127916 A1 | 7/2004 | Bolduc et al. |
| 2004/0133220 A1 | 7/2004 | Lashinski et al. |
| 2004/0133273 A1 | 7/2004 | Cox ............................. 623/2.11 |
| 2004/0138529 A1 | 7/2004 | Wiltshire et al. .............. 600/144 |
| 2004/0138744 A1 | 7/2004 | Lashinski et al. ............ 623/2.36 |
| 2004/0138745 A1 | 7/2004 | Macoviak et al. ............ 623/2.36 |
| 2004/0153146 A1 | 8/2004 | Lashinski et al. ............ 623/2.36 |
| 2004/0153147 A1 | 8/2004 | Mathis |
| 2004/0158321 A1 | 8/2004 | Reuter et al. ................ 623/2.36 |
| 2004/0176797 A1 | 9/2004 | Opolski |
| 2004/0176800 A1 | 9/2004 | Paraschac et al. |
| 2004/0186566 A1 | 9/2004 | Hindrichs et al. ............ 623/2.37 |
| 2004/0193187 A1 | 9/2004 | Boehringer et al. |
| 2004/0215232 A1 | 10/2004 | Belhe et al. .................. 606/213 |
| 2004/0220593 A1 | 11/2004 | Greenhalgh |
| 2004/0236419 A1 | 11/2004 | Milo |
| 2004/0243170 A1 | 12/2004 | Suresh et al. ................ 606/198 |
| 2004/0249408 A1 | 12/2004 | Murphy et al. ............... 606/198 |
| 2004/0249453 A1 | 12/2004 | Cartledge et al. ............ 623/2.37 |
| 2004/0260390 A1 | 12/2004 | Sarac et al. .................. 623/1.24 |
| 2004/0260393 A1 | 12/2004 | Rahdert et al. .............. 623/2.36 |
| 2004/0267191 A1 | 12/2004 | Gifford, III et al. |
| 2004/0267358 A1 | 12/2004 | Reitan ......................... 623/2.37 |
| 2005/0004668 A1 | 1/2005 | Aklog et al. ................. 623/2.36 |
| 2005/0015109 A1 | 1/2005 | Lichtenstein ................. 606/200 |
| 2005/0038509 A1 | 2/2005 | Ashe ............................ 623/2.36 |
| 2005/0054938 A1 | 3/2005 | Wehman et al. .............. 600/483 |
| 2005/0055089 A1 | 3/2005 | Macoviak et al. ............ 623/2.36 |
| 2005/0060030 A1 | 3/2005 | Lashinski et al. ............ 623/2.37 |
| 2005/0064665 A1 | 3/2005 | Han ............................. 438/286 |
| 2005/0065420 A1 | 3/2005 | Collins et al. |
| 2005/0065504 A1 | 3/2005 | Melsky et al. |
| 2005/0075727 A1 | 4/2005 | Wheatley ..................... 623/2.17 |
| 2005/0080402 A1 | 4/2005 | Santamore et al. ............ 606/1 |
| 2005/0090840 A1 | 4/2005 | Gerbino et al. |
| 2005/0096047 A1 | 5/2005 | Haberman et al. |
| 2005/0096498 A1 | 5/2005 | Hauser et al. |
| 2005/0096589 A1 | 5/2005 | Shachar |
| 2005/0096647 A1 | 5/2005 | Steinke et al. |
| 2005/0107723 A1 | 5/2005 | Wehman et al. .............. 600/595 |
| 2005/0107871 A1 | 5/2005 | Realyvasquez et al. ..... 623/2.11 |
| 2005/0125030 A1 | 6/2005 | Forsberg et al. ............. 606/213 |
| 2005/0131441 A1 | 6/2005 | Iio et al. |
| 2005/0137659 A1 | 6/2005 | Garabedian et al. |
| 2005/0137689 A1 | 6/2005 | Salahieh et al. |
| 2005/0137700 A1 | 6/2005 | Spence et al. ................ 623/2.36 |
| 2005/0143809 A1 | 6/2005 | Salahieh et al. ............. 623/2.11 |
| 2005/0148892 A1 | 7/2005 | Desai |
| 2005/0149014 A1 | 7/2005 | Hauck et al. .................. 606/41 |
| 2005/0149114 A1 | 7/2005 | Cartledge et al. |
| 2005/0154252 A1 | 7/2005 | Sharkey et al. ............... 600/37 |
| 2005/0177180 A1 | 8/2005 | Kaganov et al. ............. 606/151 |
| 2005/0177227 A1 | 8/2005 | Heim et al. .................. 623/2.12 |
| 2005/0182365 A1 | 8/2005 | Hennemann et al. ......... 604/113 |
| 2005/0187620 A1 | 8/2005 | Pai et al. ...................... 623/2.37 |
| 2005/0197692 A1 | 9/2005 | Pai et al. ...................... 623/2.1 |
| 2005/0197693 A1 | 9/2005 | Pai et al. ...................... 623/2.1 |
| 2005/0197694 A1 | 9/2005 | Pai et al. ...................... 623/2.1 |
| 2005/0197716 A1 | 9/2005 | Sharkey et al. .............. 623/23.67 |
| 2005/0203558 A1 | 9/2005 | Maschke |
| 2005/0209636 A1 | 9/2005 | Widomski et al. ........... 606/213 |
| 2005/0216052 A1 | 9/2005 | Mazzocchi et al. .......... 606/200 |
| 2005/0216054 A1 | 9/2005 | Widomski et al. ........... 606/213 |
| 2005/0240249 A1 | 10/2005 | Tu et al. ........................ 607/96 |
| 2005/0251116 A1 | 11/2005 | Steinke et al. ................. 606/8 |
| 2005/0251132 A1 | 11/2005 | Oral et al. |
| 2005/0256521 A1 | 11/2005 | Kozel |
| 2005/0267573 A9 | 12/2005 | Macoviak et al. ........... 623/2.36 |
| 2005/0267574 A1 | 12/2005 | Cohn et al. .................. 623/2.36 |
| 2005/0273138 A1 | 12/2005 | To et al. |
| 2006/0004424 A1 | 1/2006 | Loeb et al. |
| 2006/0009755 A1 | 1/2006 | Sra |
| 2006/0009756 A1 | 1/2006 | Francischelli et al. |
| 2006/0014998 A1 | 1/2006 | Sharkey et al. ............... 600/16 |
| 2006/0015002 A1 | 1/2006 | Moaddeb et al. .............. 600/37 |
| 2006/0015003 A1 | 1/2006 | Moaddes et al. ............... 600/37 |
| 2006/0015038 A1 | 1/2006 | Weymarn-Scharli ......... 600/585 |
| 2006/0015096 A1 | 1/2006 | Hauck et al. |
| 2006/0025784 A1 | 2/2006 | Starksen et al. |
| 2006/0025800 A1 | 2/2006 | Suresh ......................... 606/198 |
| 2006/0030881 A1 | 2/2006 | Sharkey et al. .............. 606/213 |
| 2006/0058871 A1 | 3/2006 | Zakay et al. ................. 623/2.18 |
| 2006/0085049 A1 | 4/2006 | Cory et al. |
| 2006/0135968 A1 | 6/2006 | Schaller ....................... 606/144 |
| 2006/0135970 A1 | 6/2006 | Schaller ....................... 606/152 |
| 2006/0173536 A1 | 8/2006 | Mathis et al. ................ 623/2.11 |
| 2006/0184242 A1 | 8/2006 | Lichtenstein ................. 623/2.37 |
| 2006/0199995 A1 | 9/2006 | Vijay .............................. 600/37 |
| 2006/0229491 A1 | 10/2006 | Sharkey et al. ............... 600/37 |
| 2006/0235286 A1 | 10/2006 | Stone et al. .................. 600/381 |
| 2006/0235314 A1 | 10/2006 | Migliuolo et al. |
| 2006/0241334 A1 | 10/2006 | Dubi et al. ..................... 600/16 |
| 2006/0241745 A1 | 10/2006 | Solem ......................... 623/2.18 |
| 2006/0264980 A1 | 11/2006 | Khairkhahan et al. ........ 606/153 |
| 2006/0276683 A1 | 12/2006 | Feld et al. ..................... 600/16 |
| 2006/0281965 A1 | 12/2006 | Khairkhahan et al. ......... 600/37 |
| 2006/0293698 A1 | 12/2006 | Douk ........................... 606/142 |
| 2006/0293725 A1 | 12/2006 | Rubinsky et al. |
| 2007/0016006 A1 | 1/2007 | Shachar |
| 2007/0016068 A1 | 1/2007 | Grunwald et al. ............ 600/468 |
| 2007/0016288 A1 | 1/2007 | Gurskis et al. |
| 2007/0027533 A1 | 2/2007 | Douk ........................... 623/2.11 |
| 2007/0038208 A1 | 2/2007 | Kefer |
| 2007/0050019 A1 | 3/2007 | Hyde |
| 2007/0060895 A1 | 3/2007 | Sibbitt et al. |
| 2007/0083076 A1 | 4/2007 | Lichtenstein |
| 2007/0088362 A1 | 4/2007 | Bonutti et al. |
| 2007/0115390 A1 | 5/2007 | Makara et al. |
| 2007/0118215 A1 | 5/2007 | Moaddeb ..................... 623/2.37 |
| 2007/0129717 A1 | 6/2007 | Brown, III et al. |
| 2007/0135826 A1 | 6/2007 | Zaver et al. .................. 606/157 |
| 2007/0135913 A1 | 6/2007 | Moaddeb et al. |
| 2007/0156233 A1 | 7/2007 | Kapadia et al. .............. 623/2.11 |
| 2007/0161846 A1 | 7/2007 | Nikolic et al. ................. 600/16 |
| 2007/0185571 A1 | 8/2007 | Kapadia et al. .............. 623/2.11 |
| 2007/0198057 A1 | 8/2007 | Gelbart et al. |
| 2007/0198058 A1 | 8/2007 | Gelbart et al. ............... 606/213 |
| 2007/0213578 A1 | 9/2007 | Khairkhahan et al. ......... 600/16 |
| 2007/0213815 A1 | 9/2007 | Khairkhahan et al. ........ 623/3.1 |
| 2007/0219460 A1 | 9/2007 | Goldenberg ................. 600/566 |
| 2007/0225736 A1 | 9/2007 | Zeiner et al. |
| 2007/0249999 A1 | 10/2007 | Sklar et al. |
| 2007/0250160 A1 | 10/2007 | Rafiee .......................... 623/2.11 |
| 2007/0270681 A1* | 11/2007 | Phillips et al. ................ 600/407 |
| 2007/0270688 A1 | 11/2007 | Gelbart et al. ................ 600/427 |
| 2007/0270943 A1 | 11/2007 | Solem et al. ................. 623/2.11 |
| 2007/0299343 A1 | 12/2007 | Waters |
| 2008/0004534 A1 | 1/2008 | Gelbart et al. |
| 2008/0004643 A1 | 1/2008 | To et al. ........................ 606/159 |
| 2008/0004697 A1 | 1/2008 | Lichtenstein et al. ........ 623/2.11 |
| 2008/0033541 A1 | 2/2008 | Gelbart et al. ............... 623/2.11 |
| 2008/0045778 A1 | 2/2008 | Lichtenstein et al. .......... 600/16 |
| 2008/0051802 A1 | 2/2008 | Schostek et al. |
| 2008/0071298 A1 | 3/2008 | Khairkhanan et al. ........ 606/151 |
| 2008/0082538 A1 | 4/2008 | Meijer et al. |
| 2008/0086164 A1 | 4/2008 | Rowe ........................... 606/191 |
| 2008/0132915 A1* | 6/2008 | Buckman et al. ............. 606/138 |
| 2008/0133002 A1 | 6/2008 | Gelbart et al. |
| 2008/0140188 A1 | 6/2008 | Rahdert et al. ................ 623/2.1 |
| 2008/0177300 A1 | 7/2008 | Mas et al. |
| 2008/0228266 A1 | 9/2008 | McNamara et al. |
| 2008/0262609 A1 | 10/2008 | Gross et al. .................. 623/2.36 |
| 2008/0269785 A1 | 10/2008 | Lampropoulos et al. |
| 2008/0275477 A1 | 11/2008 | Sterrett et al. |
| 2008/0288060 A1 | 11/2008 | Kaye et al. ................... 623/2.36 |
| 2008/0312713 A1 | 12/2008 | Wilfley et al. |

(56) References Cited

U.S. PATENT DOCUMENTS

| | | | |
|---|---|---|---|
| 2009/0076597 A1 | 3/2009 | Dahlgren et al. | 623/2.1 |
| 2009/0131930 A1 | 5/2009 | Gelbart et al. | |
| 2009/0157058 A1 | 6/2009 | Ferren et al. | |
| 2009/0192441 A1 | 7/2009 | Gelbart et al. | |
| 2009/0192527 A1* | 7/2009 | Messas | 606/144 |
| 2009/0192539 A1 | 7/2009 | Lichtenstein | |
| 2009/0204180 A1 | 8/2009 | Gelbart | |
| 2009/0287304 A1 | 11/2009 | Dahlgren et al. | 623/2.37 |
| 2010/0087836 A1 | 4/2010 | Jaramillo et al. | |
| 2010/0087837 A1 | 4/2010 | Jaramillo et al. | |
| 2010/0161047 A1 | 6/2010 | Cabiri | 623/2.37 |
| 2010/0222789 A1 | 9/2010 | Gelbart et al. | 606/142 |
| 2011/0022166 A1 | 1/2011 | Dahlgren et al. | 623/2.11 |
| 2011/0082538 A1 | 4/2011 | Dahlgren et al. | 623/2.11 |
| 2011/0087203 A1 | 4/2011 | Lichtenstein et al. | |
| 2011/0087227 A1 | 4/2011 | Mazur et al. | 606/62 |
| 2011/0125172 A1 | 5/2011 | Gelbart et al. | |
| 2011/0172658 A1 | 7/2011 | Gelbart et al. | |
| 2011/0301618 A1 | 12/2011 | Lichtenstein | 606/142 |
| 2012/0083806 A1 | 4/2012 | Goertzen | |
| 2012/0158016 A1 | 6/2012 | Gelbart et al. | |
| 2012/0245604 A1 | 9/2012 | Tegzes | 606/151 |
| 2013/0041405 A1 | 2/2013 | Gelbart et al. | |
| 2013/0238089 A1 | 9/2013 | Lichtenstein et al. | |
| 2013/0345797 A1 | 12/2013 | Dahlgren et al. | |
| 2014/0135913 A1 | 5/2014 | Lichtenstein et al. | |

FOREIGN PATENT DOCUMENTS

| | | | |
|---|---|---|---|
| WO | 90/15582 A1 | 12/1990 | |
| WO | 95/10320 A1 | 4/1995 | |
| WO | 01/78625 A1 | 10/2001 | |
| WO | 03/015611 | 2/2003 | |
| WO | 03/077800 | 9/2003 | |
| WO | 2004/012629 | 2/2004 | |
| WO | 2004/047679 | 6/2004 | |
| WO | 2004/084746 | 10/2004 | |
| WO | 2004/100803 | 11/2004 | |
| WO | 2005/007031 A2 | 1/2005 | |
| WO | 2005/046520 A2 | 5/2005 | |
| WO | 2005/070330 | 8/2005 | |
| WO | 2005/102181 | 11/2005 | |
| WO | 2006/017809 | 2/2006 | |
| WO | 2006/105121 A2 | 10/2006 | |
| WO | 2006/135747 | 12/2006 | |
| WO | 2006/135749 | 12/2006 | |
| WO | 2007/021647 | 2/2007 | |
| WO | 2007/115390 | 10/2007 | |
| WO | 2008/002606 A2 | 1/2008 | |
| WO | 2009/065042 A2 | 5/2009 | |

OTHER PUBLICATIONS

Gelbart et al., "Method and Device for Closing Holes in Tissue," Office Action mailed Feb. 23, 2012 for U.S. Appl. No. 12/777,883, 8 pages.

Gelbart et al., "Method and Device for Closing Holes in Tissue," Amendment filed May 4, 2012 for U.S. Appl. No. 12/777,883, 12 pages.

International Search Report, mailed Jun. 16, 2011, for PCT/US2010/050945, 5 pages.

Mazur et al., "Bone Fixation Device, Tools and Methods," U.S. Appl. No. 61/138,920, filed Dec. 18, 2008, 88 pages.

Written Opinion, mailed Jun. 16, 2011, for PCT/US2010/050945, 4 pages.

Athanasuleas et al., "Surgical Anterior Ventricular Restoration for Ischemic Cardiomyopathy," *Operative Techniques in Thoracic and Cardiovascular Surgery* 7(2):66-75, May 2002.

Buchbinder, Maurice, MD, "Dynamic Mitral Valve Annuloplasty: A Reshapable Ring for Residual and Recurring MR," from the *Foundation for Cardiovascular Medicine,* La Jolla, CA. May 24, 2007.

Cardiac Implants, URL=http://nmtmedical.com/products/ci/index.htm, download date May 13, 2006, 1 page.

Cooley, "Ventricular Aneurysms and Akinesis," *Cleveland Clinic Quarterly* 45(1):130-132, 1978.

Dahlgren et al., "Medical Device for Constricting Tissue or a Bodily Orifice, for Example a Mitral Valve," Office Action mailed Dec. 18, 2009, for U.S. Appl. No. 12/120,195, 9 pages.

Dahlgren et al., "Medical Device for Constricting Tissue or a Bodily Orifice, for Example a Mitral Valve," Amendment filed Apr. 13, 2010, for U.S. Appl. No. 12/120,195, 22 pages.

Dahlgren et al., "Medical Device for Constricting Tissue or a Bodily Orifice, for Example a Mitral Valve," Office Action mailed Jul. 7, 2010, for U.S. Appl. No. 12/120,195, 14 pages.

Dahlgren et al., "Medical Device, Kit and Method for Constricting Tissue or a Bodily Orifice, for Example a Mitral Valve," U.S. Appl. No. 61/278,232, filed Oct. 1, 2009, 215 pages.

Dahlgren et al., "Medical Device for Constricting Tissue or a Bodily Orifice, for Example a Mitral Valve," Preliminary Amendment filed Oct. 6, 2010 for U.S. Appl. No. 12/899,407, 8 pages.

David et al., "Postinfarction Ventricular Septal Rupture: Repair by Endocardial Patch with Infarct Exclusion," *Journal of Thoracic and Card Surgery* 110(5):1315-1322, 1995.

Dor et al., "Left Ventricular Aneurysm: a New Surgical Approach," *Thoracic Cardiovascular Surgery* 37:11-19, 1989.

Dor et al., "Late Hemodynamic Results After Left Ventricular Patch Repair Associated with Coronary Grafting in Patients with Postinfarction Akinetic or Dyskinetic Aneurysm of the Left Ventricle," *Journal of Thoracic and Cardiovascular Surgery* 110(5):1291-1301, 1995.

Dor, "Left Ventricular Aneurysms: The Endoventricular Circular Patch Plasty," *Seminars in Thoracic and Cardiovascular Surgery* 9(2):123-130, Apr. 1997.

Gelbart et al., "Method and Device for Closing Holes in Tissue," Office Action mailed Sep. 4, 2008, for U.S. Appl. No. 11/436,585, 8 pages.

Gelbart et al., "Method and Device for Closing Holes in Tissue," Amendment filed Sep. 22, 2008, for U.S. Appl. No. 11/436,585, 3 pages.

Gelbart et al., "Method and Device for Closing Holes in Tissue," Office Action mailed Jan. 2, 2009, for U.S. Appl. No. 11/436,585, 11 pages.

Gelbart et al., "Method and Device for Closing Holes in Tissue," Amendment filed Jan. 30, 2009, for U.S. Appl. No. 11/436,585, 5 pages.

Gelbart et al., "Method and Device for Closing Holes in Tissue," Amendment filed Jun. 2, 2009, for U.S. Appl. No. 11/436,585, 7 pages.

Gelbart et al., "Method and Device for Closing Holes in Tissue," Office Action mailed Jul. 7, 2009, for U.S. Appl. No. 11/436,585, 9 pages.

Gelbart et al., "Method and Device for Closing Holes in Tissue," Amendment filed Oct. 26, 2009, for U.S. Appl. No. 11/436,585, 13 pages.

Gelbart et al., "Automatic Atherectomy System," Amendment filed Aug. 4, 2009 for U.S. Appl. No. 11/436,584, 35 pages.

Gelbart et al., "Automatic Atherectomy System," Amendment filed Mar. 30, 2010 for U.S. Appl. No. 11/436,584, 20 pages.

Gelbart et al., "Automatic Atherectomy System," Amendment filed Oct. 25, 2010 for U.S. Appl. No. 11/436,584, 9 pages.

Gelbart et al., "Automatic Atherectomy System," Office Action mailed Mar. 4, 2009 for U.S. Appl. No. 11/436,584, 7 pages.

Gelbart et al., "Automatic Atherectomy System," Office Action mailed Dec. 1, 2009 for U.S. Appl. No. 11/436,584, 10 pages.

Gelbart et al., "Automatic Atherectomy System," Office Action mailed Dec. 14, 2010 for U.S. Appl. No. 11/436,584, 12 pages.

Gelbart et al., "Artificial Valve," Office Action mailed May 7, 2010 for U.S. Appl. No. 11/497,306, 12 pages.

Gelbart et al., "Artificial Valve," Amendment filed Jan. 29, 2010 for U.S. Appl. No. 11/497,306, 22 pages.

International Search Report, mailed Jan. 8, 2007, for PCT/CA2006/001123, 5 pages.

International Search Report, mailed Sep. 4, 2009, for PCT/US2009/043612, 7 pages.

Jatene, "Left Ventricular Aneurysmectomy," *Journal of Thoracic and Cardiovascular Surgery* 89(3):321-331, 1985.

(56) References Cited

OTHER PUBLICATIONS

Konings et al., "Development of an Intravascular Impedance Catheter for Detection of Fatty Lesions in Arteries," *IEEE Transactions on Medical Imaging,* 16(4):439-446, 1997.
Lichtenstein et al., "Method for Anchoring a Mitral Valve," Office Action mailed May 1, 2009, for U.S. Appl. No. 11/475,978, 6 pages.
Lichtenstein et al, "Method for Anchoring a Mitral Valve," Amendment filed Aug. 31, 2009, for U.S. Appl. No. 11/475,978, 24 pages.
Lichtenstein et al, "Method for Anchoring a Mitral Valve," Amendment filed Mar. 26, 2010, for U.S. Appl. No. 11/475,978, 19 pages.
Lichtenstein et al, "Method for Anchoring a Mitral Valve," Office Action mailed Dec. 29, 2009, for U.S. Appl. No. 11/475,978, 7 pages.
Lichtenstein, "Method and Apparatus for Percutaneous Reduction of Anterior-Posterior Diameter of Mitral Valve," Office Action mailed May 15, 2006, for U.S. Appl. No. 10/690,131, 9 pages.
Lichtenstein, "Method and Apparatus for Percutaneous Reduction of Anterior-Posterior Diameter of Mitral Valve," Office Action mailed Dec. 1, 2008, for U.S. Appl. No. 11/400,260, 10 pages.
Lichtenstein et al., "System for Improving Diastolic Dysfunction," Office Action mailed Dec. 24, 2008 for U.S. Appl. No. 11/497,309, 8 pages.
Lichtenstein et al., "System for Improving Diastolic Dysfunction," Amendment filed Apr. 22, 2009 for U.S. Appl. No. 11/497,309, 23 pages.
Lichtenstein et al., "System for Improving Diastolic Dysfunction," Office Action mailed Aug. 5, 2009 for U.S. Appl. No. 11/497,309, 10 pages.
Lichtenstein et al., "System for Improving Diastolic Dysfunction," Amendment filed Oct. 23, 2009 for U.S. Appl. No. 11/497,309, 9 pages.
Lichtenstein et al., "System for Improving Diastolic Dysfunction," Office Action mailed Jan. 20, 2010 for U.S. Appl. No. 11/497,309, 10 pages.
Lichtenstein et al., "System for Improving Diastolic Dysfunction," Amendment filed Apr. 7, 2010 for U.S. Appl. No. 11/497,309, 8 pages.
Mack, "New Techniques for Percutaneous Repair of the Mitral Valve," *Heart Failure Review,* 11:259-268, 2006.
Menicanti et al., "The Dor Procedure: What has Changed After Fifteen Years of Clinical Practice?" *Journal of Thoracic and Cardiovascular Surgery* 124(5):886-890, Nov. 2002.
Otasevic et al., "First-in-Man Implantation of Left Ventricular Partitioning Device in a Patient With Chronic Heart Failure: Twelve-Month Follow-up," *Journal of Cardiac Failure* 13(7):517-520, 2007.
Rivera et al., "Ventricular Aneurysms and Akinesis," *Cleveland Clinic Quarterly* 45(1):133-135, 1978.
Sharkey et al., "Left Ventricular Apex Occluder. Description of a Ventricular Partitioning Device," *EuroIntervention* 2:125-127, 2006.
Stiles, et al., "Simulated Characterization of Atherosclerotic Lesions in the Coronary Arteries by Measurement of Bioimpedance," *IEE Transactions on Biomedical Engineering,* 50(7):916-921, 2003.
Tanaka et al., "Artificial SMA Valve for Treatment of Urinary Incontinence: Upgrading of Valve and Introduction of Transcutaneous Transformer," *Bio-Medical Materials and Engineering* 9:97-112, 1999.
Timek et al., "Septal-Lateral Annular Cinching Abolishes Acute Ischemic Mitral Regurgitation," *Journal of Thoracic and Cardiovascular Surgery,* 123(5):881-888, 2002.
Torrent-Guasp et al., "Spatial Orientation of the Ventricular Muscle Band and Approach to Partial Ventriculotomy in Heart Failure," *Pathogenesis and Treatment,* Ch. 36, pp. 685-693.
Valvano et al., "Thermal Conductivity and Diffusivity of Biomaterials Measured with Self-Heated Thermistors," *International Journal of Thermodynamics,* 6(3):301-311, 1985.
Written Opinion, mailed Jan. 8, 2007, for PCT/CA2006/001123, 6 pages.
Written Opinion, mailed Sep. 4, 2009, for PCT/US2009/043612, 6 pages.
"Constellation Mapping Catheters", Brochure, Boston Scientific Corp., 2 pgs, © 2007 Boston Scientific Corporation.

"Phased RF Catheter Ablation System", 2014 Medtronic Inc., 2 pgs, http://www.medtronic.eu/your-health/atrial-fibrillation/about-the-therapy/our-phased-rf-ablation-system/[Jun. 24, 2014 2:38:05 PM].
"ThermoCool® Irrigated Tip Catheter", Brochure, Biosense Webster, 4 pgs, Biosense Webster, Inc. 3333 Diamond Canyon Road Diamond Bar, CA 91765, USA, © Biosense Webster, Inc. 2009 All rights reserved. 1109003.0.
Biotronik's "AlCath Flutter Gold Cath for Atrial Flutter Available in EU", medGadget, 3 pgs, http://www.medgadget.com/2013/09/biotroniks-alcath-flutter-gold-cath-for-atrial-flutter-unveiled-in-europe.html[Jun. 24, 2014 2:37:09 PM].
Dahlgren et al., "Medical Device for Constricting Tissue or a Bodily Orifice, for Example a Mitral Valve", Amendment filed Aug. 8, 2013 for U.S. Appl. No. 12/899,407, 65 pages.
Dahlgren et al., "Medical Device for Constricting Tissue or a Bodily Orifice, for Example a Mitral Valve", Amendment filed Dec. 13, 2012 for U.S. Appl. No. 12/899,407, 22 pages.
Dahlgren et al., "Medical Device for Constricting Tissue or a Bodily Orifice, for Example a Mitral Valve", Office Action mailed Mar. 8, 2013 for U.S. Appl. No. 12/899,407, 23 pages.
Dahlgren et al., "Medical Device, Kit and Method for Constricting Tissue or a Bodily Orifice, For Example a Mitral Valve", Amendment filed Nov. 30, 2012 for U.S. Appl. No. 12/894,912, 30 pgs.
Dahlgren et al., "Medical Device, Kit and Method for Constricting Tissue or a Bodily Orifice, For Example a Mitral Valve", Final Office Action mailed Feb. 13, 2013 for U.S. Appl. No. 12/894,912, 35 pgs.
Dahlgren et al., "Medical Device, Kit and Method for Constricting Tissue or a Bodily Orifice, For Example a Mitral Valve", Office Action mailed Aug. 30, 2012 for U.S. Appl. No. 12/894,912, 16 pgs.
Dahlgren et al., "Medical Device, Kit and Method for Constricting Tissue or a Bodily Orifice, For Example a Mitral Valve", Response filed Jun. 13, 2013 for U.S. Appl. No. 12/894,912, 3 pgs.
Dahlgren et al., "Medical Device, Kit and Method for Constricting Tissue or a Bodily Orifice, for Example, a Mitral Valve", Office Action mailed Jul. 9, 2014 for U.S. Appl. No. 13/917,469, 37 pgs.
Dahlgren et al., "System for Mechanical Adjustment of Medical Implants", Amendment filed Apr. 2, 2010 for U.S. Appl. No. 11/902,099, 19 pgs.
Dahlgren et al., "System for Mechanical Adjustment of Medical Implants", Amendment filed Nov. 1, 2010 for U.S. Appl. No. 11/902,099, 12 pgs.
Dahlgren et al., "System for Mechanical Adjustment of Medical Implants", Office Action mailed Jul. 8, 2010 for U.S. Appl. No. 11/902,099, 37 pgs.
Dahlgren et al., "System for Mechanical Adjustment of Medical Implants", Office Action mailed Oct. 5, 2009 for U.S. Appl. No. 11/902,099, 13 pgs.
European Search Report, mailed Jun. 26, 2008 for EP 08100878.1, 11 pgs.
Gelbart, "System for Implanting a Microstimulator", Amendment filed Jan. 20, 2010 for U.S. Appl. No. 12/068,878, 26 pgs.
Gelbart, "System for Implanting a Microstimulator", Office Action mailed Aug. 18, 2010 for U.S. Appl. No. 12/068,878, 11 pgs.
Gelbart, "System for Implanting a Microstimulator", Office Action mailed Aug. 20, 2009 for U.S. Appl. No. 12/068,878, 12 pgs.
Goertzen et al., "Tissue Anchor System", Amendment filed Apr. 29, 2013 for U.S. Appl. No. 13/247,380, 22 pgs.
International Search Report mailed Dec. 6, 2004 for PCT/IB2004/002581, 3 pgs.
Lichtenstein "Closing Openings in Anatomical Tissue", Amendment filed Aug. 8, 2013 for U.S. Appl. No. 13/112,695, 23 pgs.
Lichtenstein "Closing Openings in Anatomical Tissue", Office Action mailed May 8, 2013 for U.S. Appl. No. 13/112,695, 12 pgs.
Lichtenstein "Method and Apparatus for Percutaneous Reduction of Anterior-Posterior Diameter of Mitral Valve", U.S. Appl. No. 10/690,131, filed Oct. 20, 2003, 31 pgs.
Lichtenstein et al., "System for Improving Diastolic Dysfunction", Office Action mailed Sep. 18, 2012 for U.S. Appl. No. 12/904,885, 15 pgs.
Lichtenstein et al., "System for Improving Diastolic Dysfunction", Preliminary Amendment filed Oct. 14, 2010 for U.S. Appl. No. 12/904,885, 23 pgs.

(56) References Cited

OTHER PUBLICATIONS

Lichtenstein, "Closing Openings in Anatomical Tissue", Final Office Action mailed Dec. 4, 2013 for U.S. Appl. No. 13/112,695, 31 pages.
Lichtenstein, "Methods and Devices for Altering Blood Flow Through the Left Ventricle", Amendment filed Jul. 26, 2007 for U.S. Appl. No. 10/922,129, 17 pages.
Lichtenstein, "Methods and Devices for Altering Blood Flow Through the Left Ventricle", Examiner's Amendment mailed Mar. 2, 2009 for U.S. Appl. No. 10/622,129, 5 pages.
Lichtenstein, "Methods and Devices for Altering Blood Flow Through the Left Ventricle", Office Action mailed Jul. 9, 2010 for U.S. Appl. No. 10/571,165, 11 pages.
Lichtenstein, "Methods and Devices for Altering Blood Flow Through the Left Ventricle", Office Action mailed Mar. 26, 2007 for U.S. Appl. No. 10/622,129, 17 pages.
Lichtenstein, "Methods and Devices for Altering Blood Flow Through the Left Ventricle", Office Action mailed Nov. 14, 2007 for U.S. Appl. No. 10/622,129, 6 pages.
Lichtenstein, "Methods and Devices for Altering Blood Flow Through the Left Ventricle", Preliminary Amendment filed Feb. 14, 2008 for U.S. Appl. No. 10/622,129, 15 pages.
Lichtenstein, "Methods and Devices for Altering Blood Flow Through the Left Ventricle", Preliminary Amendment filed Mar. 6, 2006 for U.S. Appl. No. 10/571,165, 7 pages.
Tegzes, "Medical Kit for Constricting Tissue or a Bodily Orifice, for Example, a Mitral Valve", Office Action mailed Jul. 11, 2014 for U.S. Appl. No. 13/421,677, 9 pgs.
Timek, et al., "Septal-Lateral Annular Cinching (SLAC) Reduces Mitral Annular Size Without Perturbing Normal Annular Dynamics", Journal of Heart Valve Disease, vol. 11, No. 1, Jan. 2002; pp. 2-10.
Written Opinion mailed Dec. 6, 2004 for PCT/IB2004/002581, 8 pgs.
Star Close Vascular Closure System Brochure, 2005, Abbott Vascular, pp. 1-4.
Extended European Search Report mailed Sep. 18, 2014 for EP 10821276.2, 10 pages.
Gelbart et al., "Automatic Atherectomy System", Notice of Allowance mailed May 10, 2013 and Certificate of Correction mailed May 6, 2014 for U.S. Appl. No. 13/404,834, 11 pgs.
Gelbart et al., "Automatic Atherectomy System", Amendment filed Jan. 16, 2013 for U.S. Appl. No. 13/404,834, 13 pgs.
Gelbart et al., "Automatic Atherectomy System", Notice of Allowance mailed Aug. 20, 2010 for U.S. Appl. No. 11/436,584, 12 pgs.
Gelbart et al., "Automatic Atherectomy System", Notice of Allowance mailed Nov. 25, 2011 and Certificate of Correction mailed Jul. 17, 2012 for U.S. Appl. No. 12/950,871, 24 pgs.
Gelbart et al., "Method and Device for Closing Holes in Tissue", Response to Quayle Action filed Jul. 14, 2014 for U.S. Appl. No. 13/652,299, 29 pages.
Gelbart et al., "Method and Device for Closing Holes in Tissue", Quayle Action mailed May 20, 2014 for U.S. Appl. No. 13/652,299, 25 pages.
Gelbart et al., "Method and Device for Closing Holes in Tissue", Preliminary Amendment fiiled Feb. 21, 2013 for U.S. Appl. No. 13/652,299, 9 pages.
Gelbart et al., "Method and Device for Closing Holes in Tissue", Notice of Allowance mailed Feb. 24, 2010, Supplemental Notice of Allowance mailed Mar. 24, 2010 and Remarks filed after allowance on Apr. 9, 2010 for U.S. Appl. No. 11/436,585, 20 pgs.
Gelbart et al., "Method and Device for Closing Holes in Tissue", Notice of Allowance mailed Aug. 22, 2012 for U.S. Appl. No. 12/777,883, 12 pgs.
Lichtenstein et al., "System for Improving Diastolic Dysfunction", Amendment filed Dec. 18, 2012 for U.S. Appl. No. 12/904,885, 23 pgs.
Lichtenstein et al., "System for Improving Diastolic Dysfunction", Amendment filed Apr. 9, 2014 for U.S. Appl. No. 12/904,885, 24 pgs.
Lichtenstein et al., "Method for Anchoring a Mitral Valve", Notices of Allowance mailed Oct. 2, 2013 and Nov. 13, 2013 for U.S. Appl. No. 13/872,870, 35 pgs.
Lichtenstein et al., "Method for Anchoring a Mitral Valve", Notice of Allowance mailed Jan. 28, 2013 for U.S. Appl. No. 11/475,978, 24 pgs.
Lichtenstein et al., "Method for Anchoring a Mitral Valve", Preliminary Amendment filed Jan. 24, 2014 for U.S. Appl. No. 14/162,469, 9 pgs.
Lichtenstein et al., "System for Improving Diastolic Dysfunction", Notice of Allowance mailed Jul. 12, 2010 for U.S. Appl. No. 11/497,309, 8 pgs.
Lichtenstein et al., "System for Improving Diastolic Dysfunction", Office Action mailed Jan. 29, 2014 for U.S. Appl. No. 12/904,885, 38 pgs.
Dahlgren et al., "Medical Device for Constricting Tissue or a Bodily Orifice, for Example a Mitral Valve", Amendment filed Jul. 23, 2013 for U.S. Appl. No. 12/899,407, 60 pages.

* cited by examiner

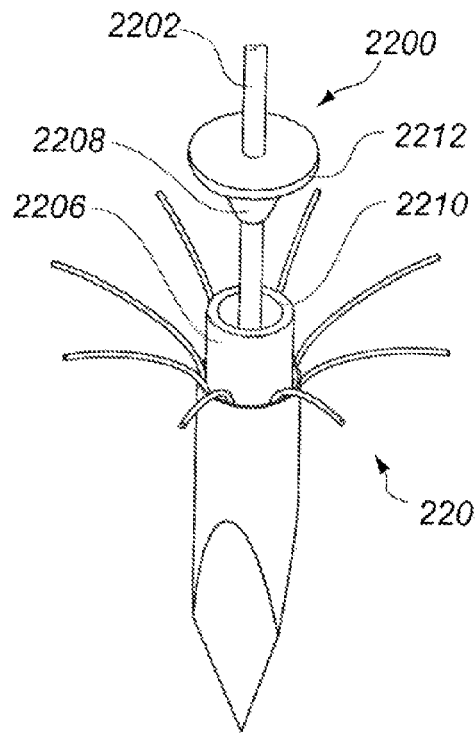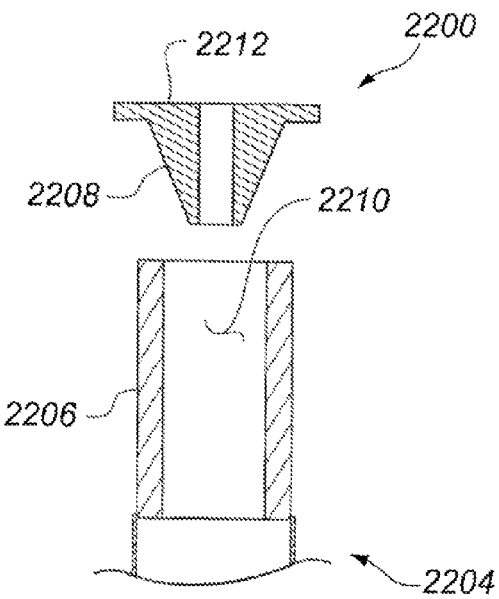
FIG. 22A    FIG. 22B
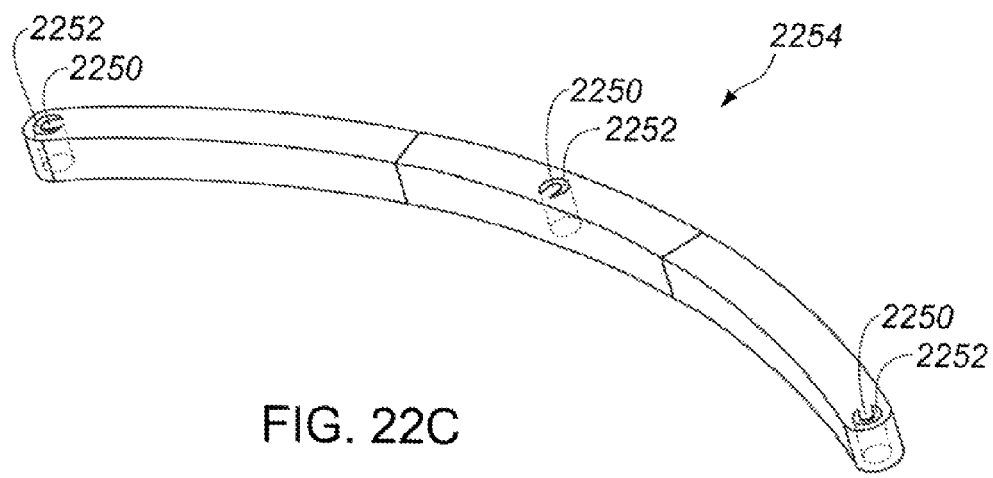
FIG. 22C

TISSUE ANCHOR SYSTEM

CROSS-REFERENCE TO RELATED APPLICATIONS

This application claims benefit under 37 U.S.C. 119(e) to U.S. patent application Ser. No. 61/388,405, filed Sep. 30, 2010, which is incorporated by reference herein in its entirety.

BACKGROUND

1. Field

This disclosure is generally related to percutaneous or minimally invasive surgery, and more particularly to tissue anchor systems for use in percutaneously or minimally invasive surgery.

2. Description of the Related Art

Cardiac surgery was initially undertaken only by performing a sternotomy, a type of incision in the center of the chest, which separates the sternum (chest bone) to allow access to the heart. In the previous several decades, more and more cardiac operations are performed using a percutaneous technique, which is a medical procedure where access to inner organs or other tissue is gained via a catheter.

Percutaneous surgeries benefit patients by reducing surgery risk, complications, and recovery time. However, the use of percutaneous technologies also raises some particular challenges. Medical devices used in percutaneous surgery need to be deployed via narrow tubes called catheter sheaths, which significantly increase the complexity of the device structure. As well, doctors do not have direct visual contact with the medical tools used once they are placed within the body, and positioning the tools correctly and operating the tools successfully can often be very challenging. Various catheters can be deployed through a catheter sheath in percutaneous surgical applications.

One example of where percutaneous medical techniques are starting to be used is in the treatment of a heart disorder called mitral regurgitation. Mitral regurgitation is a condition in which blood flows backward from the left ventricle into the left atrium. The mitral apparatus is made up of four major structural components and includes the annulus, the two leaflets, the chordae and the papillary muscles. Improper function of any one of these structures, alone or in combination can lead to mitral regurgitation. Annular dilation is a major component in the pathology of mitral regurgitation regardless of cause and is manifested in mitral regurgitation related to dilated cardiomyopathy and chronic mitral regurgitation due to ischemia.

The mitral valve is intended to prevent the undesired flow of blood from the left ventricle into the left atrium when the left ventricle contracts. In a normal mitral valve, the geometry of the mitral valve ensures the cusps overlay each other to preclude the regurgitation of blood during left ventricular contraction and thereby prevent elevation of pulmonary vascular pressures and resultant symptoms of shortness of breath. Studies of the natural history of mitral regurgitation have found that totally asymptomatic patients with severe mitral insufficiency usually progress to severe disability within 5 years.

At present, treatment consists of either mitral valve replacement or repair. Both methods require open heart surgery. Replacement can be performed with either mechanical or biological valves and is particularly suitable when one of the mitral cusps has been severely damaged or deformed. The mechanical valve carries the risk of thromboembolism and requires anticoagulation with all of its potential hazards, whereas the biological prosthesis suffers from limited durability. Another hazard with replacement is the risk of endocarditis. These risks and other valve related complications are greatly diminished with valve repair. Mitral valve repair is theoretically possible if the mitral valve leaflets are structurally normal but fail to appropriately coapt because of annular dilatation and/or papillary muscle dysfunction. Various surgical procedures have been developed to improve coaptation of the leaflet and to correct the deformation of the mitral valve annulus and retain the intact natural heart valve function. These procedures generally involve reducing the circumference of the posterior mitral leaflet annulus (lateral annulus) where most of the dilatation occurs. The annulus of the anterior leaflet (septal annulus) does not generally dilate because it is anchored to the fibrous skeleton at the base of the heart. Such techniques, known as mitral annuloplasty, typically suture a prosthesis around the base of the valve leaflets shortening the lateral annulus to reshape the mitral valve annulus and minimize further dilation. Different types of mitral annuloplasty prostheses have been developed for use in such surgery. In general, such prostheses are annular or partially annular shaped and may be formed from rigid or flexible material.

Mitral valve surgery requires an extremely invasive approach that includes a chest wall incision, cardiopulmonary bypass, cardiac and pulmonary arrest, and an incision on the heart itself to gain access to the mitral valve. Such a procedure is expensive, requires considerable time, and is associated with high morbidity and mortality. Due to the risks associated with this procedure, many of the sickest patients are denied the potential benefits of surgical correction of mitral regurgitation. In addition, patients with moderate, symptomatic mitral regurgitation are denied early intervention and undergo surgical correction only after the development of cardiac dysfunction. Furthermore, the effectiveness of such procedures is difficult to assess during the procedure and may not be known until a much later time. Hence, the ability to make adjustments to or changes in the prosthesis function to obtain optimum effectiveness is extremely limited. Correction at a later date would require another open heart procedure.

In an attempt to treat mitral regurgitation without the need for cardiopulmonary bypass and without opening the chest, percutaneous approaches have been devised to repair the valve or place a correcting apparatus for correcting the annulus relaxation. Such approaches make use of devices which can be generally grouped into two types: 1) devices deforming (mainly shortening) the coronary sinus; and 2) devices pulling together two anchor points in order to affect the mitral valve, one of the anchor points can be the coronary sinus (typically using a wire that is pulled and secured).

Neither approach emulates the current "gold standard" in mitral valve repair—annuloplasty using an open or closed ring. Both approaches suffer from several problems as a result of attempting to reshape the mitral annulus using an alternative method. Devices that deform the coronary sinus, while suitable for percutaneous procedures, are not effective in controlling the leakage of the mitral valve as the forces are not applied from the correct opposite sides of the valve, which are the lateral annulus and the septal annulus. The devices of the second type are not easily adapted to a percutaneous procedure. In order to achieve shortening in the direction connecting the lateral annulus to the septal annulus the anchor points have to be located along this line, so pulling them together will affect the desired direction of shortening. Pulling applied along a different direction will distort the mitral valve but will not achieve the optimal approximation of the two leaflets.

Thus, there is a need for methods and apparatus that enable the ability to create a mitral annuloplasty that applies forces from various desired directions via a percutaneous or intravascular procedure.

BRIEF SUMMARY

The subject of the present application is a medical device with enhanced capabilities for percutaneous deployment and annulus shape modification and a superior method for constricting tissue or a bodily orifice, such as the mitral valve, tricuspid valve, or aortic valve via such device. The device may enable methods that enable a closed or open (i.e., split) ring to be anchored to tissue in the vicinity of an orifice or annulus and may enable a change in the shape of said annulus by the anchored ring. Reference throughout this specification is made to cardiac surgery, but the methods and apparatus described herein may also be used in gastric surgery, bowel surgery, or other surgeries in which tissue may be drawn together. The methods and apparatus described herein may also be used to draw or hold tissue not part of an orifice or annulus together. The methods and apparatus described herein may be used in minimally invasive surgery as well as intravascular or percutaneous surgery. Other advantages will become apparent from the teaching herein to those of skill in the art.

An implant kit may be summarized as including a plurality of tissue anchors comprising at least a first tissue anchor, a second tissue anchor and a third tissue anchor; a percutaneous delivery system operable to at least partially embed each of the tissue anchors into a respective location about a periphery of an orifice in a tissue within a body during an implant procedure in which a location of the embedded third tissue anchor is laterally offset by a first distance from a first axis, the first axis extending between a location of the embedded first tissue anchor and a location of the embedded second tissue anchor; an implant member reconfigurable between a delivery configuration in which the implant member is manipulable to a size and dimension to be deliverable percutaneously to the tissue within the body, and an implantable configuration in which the implantable member forms a structure sufficiently rigid to affect a shape of the orifice in the tissue, the implant member further comprising a plurality of tissue anchor receivers, each of the tissue anchor receivers positioned to physically couple with a respective one of the embedded tissue anchors, the plurality of tissue anchor receivers comprising at least a first tissue anchor receiver corresponding to the first tissue anchor, a second tissue anchor receiver corresponding to the second tissue anchor, and a third tissue anchor receiver corresponding to the third tissue anchor, wherein a location of the third tissue anchor receiver on the implant member in the implantable configuration is laterally offset by a second distance from a second axis, the second axis extending between a location of the first tissue anchor receiver on the implant member and a location of the second tissue anchor receiver on the implant member, wherein the second distance is smaller than the first distance; and a plurality of implant guide lines that in use during the implant procedure provide a physical path for the implant member to the embedded tissue anchors.

The implant member may include a plurality of segments physically coupled to one another, the segments being articuable with respect to one another as the implant member is moved between the deliverable configuration and the implantable configuration. The implant member may include a number of hinges that physically couple each of the segments to at least one other of the segments. The implant member may include a number of stops configured to increase a torsional stiffness of each of the hinges when each of the segments pivots by a defined amount with respect to another of the segments. The implant member may include a number of flexure joints that physically couple each of the segments to at least one other of the segments. The implant member may include a number of stops configured to increase a bending stiffness of each of the flexure joints when each of the segments flexes by a defined amount with respect to another of the segments. The implant member may include a number of stops configured to restrain articulation between the coupled segments.

Each of the tissue anchors may include at least one barb. Each of the tissue anchors may be a helical tissue anchor. Each of the tissue anchors may be a grapple tissue anchor, each grapple tissue anchor may include at least two prongs pivotally coupled to each other, and each of the two prongs may have a tip shaped to pierce the tissue.

The implant member may have at least three guide line receivers that each ride on respective ones of the guide lines, wherein a circumference defined by a circle passing through at least three locations of the at least three guide line receivers on the implant member in the implantable configuration may be smaller than a circumference defined by a circle passing through the respective locations of the embedded first, second and third tissue anchors prior to a physical coupling between each of the embedded first, second and third tissue anchors and respective ones of the first, second and third tissue anchor receivers.

An implant kit may be summarized as including an implant member configured to affect a shape of an orifice in tissue within a body during an implant procedure, a portion of the implant member having a variable bending stiffness in at least one dimensional plane, the implant member comprising a first end, a second end and a plurality of guide line receivers positioned between the first end and the second end along the implant member, the implant member configured to be bendable between a first configuration in which implant member has an elongated shape and a second configuration in which the implant has an arcuate shape, the first end being spaced apart from the second end by a greater distance when the implant member is in the first configuration than when the implant member is in the second configuration, and the portion of the implant member having a reduced bending stiffness in the at least one dimensional plane when the implant member is in first configuration and an increased bending stiffness in the at least one dimensional plane when the implant member is in the second configuration; a plurality of tissue anchors configured to be at least partially embedded into tissue at respective locations about the orifice in the tissue within the body; and a plurality of guide lines, each of the guide lines sized to be received by a respective one of the guide line receivers and a respective one of the tissue anchors, each of at least one of the guide lines being configured to receive a tensile force sufficient to move a portion of the tissue into which a respective tissue anchor is embedded towards the implant member in the second configuration.

The implant member may include a plurality of tissue anchor receivers positioned along the implant member between the first end and the second end, each of the tissue anchor receivers configured to physically receive a respective one of the tissue anchors, and wherein each of the at least one of the guide lines may be configured to receive a tensile force sufficient to move the portion of the tissue to a position where the respective tissue anchor embedded into the portion of the tissue is physically received by a respective tissue anchor receiver when the implant member in the second configuration.

The implant member may include a plurality of segments physically coupled to one another, the segments being articulable with respect to one another to provide the reduced bending stiffness in the at least one dimensional plane when the implant member is in the first configuration. The implant member may include a number of hinges that physically couple each of the segments to at least one other of the segments. The implant member may include a number of stops configured to increase a torsional stiffness of each of the hinges when each of the segments pivots by a defined amount with respect to another of the segments to provide the increased bending stiffness in the at least one dimensional plane when the implant member is in the second configuration. The implant member may include a number of flexure joints that physically couple each of the segments to at least one other of the segments. The implant member may include a number of stops configured to provide the increased bending stiffness in the at least one dimensional plane when the implant member is in the second configuration. The implant member may include a number of stops configured to restrain articulation between the coupled segments to provide the increased bending stiffness in the at least one dimensional plane when the implant member is in the second configuration.

The embedded tissue anchors may apply tension to implant member in the second configuration when each of the tissue anchor receivers is coupled with a respective one of the embedded tissue anchors. The applied tension may be sufficient to restrain disengagement of each of the coupled segments with an associated one of the stops. The applied tension may be sufficient to flex at least one of segments while each of the at least one of the segments is engaged with an associated one of the stops.

Each of the tissue anchors may include at least one piercing element configured for piercing the tissue. Each of the tissue anchors may be a helical tissue anchor. Each of the tissue anchors may be a grapple tissue anchor, each grapple tissue anchor may include at least two prongs pivotally coupled to each other, and each of the two prongs may have a tip shaped to pierce the tissue. The plurality of guide line receivers may include at least three guide line receivers, a circumference defined by a circle passing through at least three locations of the at least three guide line receivers on the implant member in the second configuration being smaller than a circumference defined by a circle passing through at least three locations of their respective embedded tissue anchors about the orifice in the tissue prior to a physical coupling between any of the tissue anchor receivers and their respective embedded tissue anchors.

The implant member in the first configuration may be manipulable to a size and dimension to be deliverable via a catheter. The portion of the implant member may have a substantially equal bending stiffness in each of a plurality of directions in the at least one dimensional plane when the implant member is in the first configuration and the portion of the implant member may have a substantially unequally bending stiffness in each of the plurality of directions in the at least one dimensional plane when the implant member is in the second configuration.

An implant kit may be summarized as including a plurality of tissue anchors configured to be at least partially embedded into tissue at respective locations about an orifice in the tissue during an implant procedure; an implant member having a plurality of segments physically coupled to one another, in a delivery configuration the segments being articulable with respect to one another by a respective articulation joint such that the implant member is manipulable to a size and dimension to be deliverable via a catheter and in an deployed configuration the segments form a structure sufficiently rigid to affect a shape of the orifice in the tissue when the implant member is positioned to physically couple with the embedded tissue anchors; and a plurality of implant guide lines that in use during the implant procedure provide a physical path for the implant member to respective ones of the embedded tissue anchors, the implant member moveable along the physical path to a position where the implant member is secured to the tissue under tension in the deployed configuration.

The tissue anchors and respective ones of the guide lines may be integral structures comprised of at least one of a metal wire. The tissue anchors and respective ones of the guide lines may be unitary structures, each of the tissue anchors may include at least one piercing element at a distal end of a respective one of the guide lines, wherein the at least one piercing element may be configured to pierce the tissue. The structure formed by the segments of the implant member may have a C-shape profile.

The implant kit may further include an implant cross connector attachable across an open portion of the implant member such that when attached, the implant cross connector and the structure formed by the segments of the implant member have a D-shape profile.

The implant member may have a number of guide line receivers that ride on respective ones of the guide lines. The implant member may have at least three guide line receivers, at least a first guide line receiver proximate a first end of the implant member, a second guide line receiver proximate a second end of the implant member, and a third guide line receiver positioned along the structure formed by the segments between the first and the second guide line receivers.

The respective articulation joint of the implant member may include a number of hinges that physically couple each of the segments of the implant member to at least one other of the segments of the implant member.

The implant member may include a number of stops configured to limit a travel of each of the segments of the implant member with respect to another of the segments of the implant member. The implant member may include a number of stops configured to increase a torsional stiffness of each of the hinges when each of the segments of the implant member pivots by a defined amount with respect to another of the segments of the implant member.

The respective articulation joint of the implant member may include a number of flexure joints that physically couple each of the segments of the implant member to at least one other of the segments of the implant member.

The implant member may include a number of stops configured to limit a travel of each of the segments of the implant member with respect to another of the segments of the implant member. The implant member may include a number of stops configured to increase a bending stiffness of each of the flexure joints when each of the segments of the implant member flexes by a defined amount with respect to another of the segments of the implant member.

The implant kit may further include an anchor guide frame having at least three anchor guide arms, wherein each of the tissue anchors may be configured to be physically releasably guided by a respective one of the anchor guide arms of the anchor guide frame to a respective location on an annulus about the orifice in the tissue and embedded in the annulus at least proximate the respective locations.

The anchor guide arms may each include an outer tube having at least a first outer tube lumen, and an inner tube having an inner tube lumen, the inner tube received in the first outer tube lumen of the outer tube for translational movement between a retracted position in which a distal end of the inner tube does not extend beyond a distal end of the first outer tube lumen and an extended position in which the distal end of the inner tube extends beyond the distal end of the first outer tube lumen, the inner tube lumen of the inner tube receiving a respective one of the guide lines for translation with respect thereto.

The distal end of the inner tube may be in butting engagement with a portion of a respective one of the tissue anchors until the inner tube is withdrawn from the tissue anchor after the tissue anchor has been embedded in the tissue.

The tissue anchors may each include at least one resilient barb, the at least one resilient barb protectively retained in the inner tube lumen of the inner tube until the inner tube is withdrawn from the tissue anchor after the tissue anchor has been embedded in the tissue.

The outer tube of each of the anchor guide arms may further have a second outer tube lumen; and the anchor guide frame may further include a plurality of arms, each of the arms received in the second outer tube lumen of a respective one of the anchor guide arms.

The implant member may have at least three guide line receivers that each ride on respective ones of the guide lines, wherein a circumference defined by a circle passing through at least three locations of the at least three guide line receivers on the implant member in the deployed configuration may be smaller than a circumference defined by a circle passing through at least three locations of the embedded tissue anchors in the tissue prior to a physical coupling between the implant member and the embedded tissue anchors.

The implant member may have at least three guide line receivers that each ride on respective ones of the guide lines, wherein a circumference defined by a circle passing through at least three locations of the at least three guide line receivers on the implant member in the deployed configuration may be smaller than a circumference of an annulus of the orifice in the tissue prior to a physical coupling between the implant member and the embedded tissue anchors.

The implant member may have at least three tissue anchor receivers, each of the tissue anchor receivers positioned to physically couple with a respective one of the plurality of tissue anchors, wherein a circumference defined by a circle passing through at least three locations of the at least three tissue anchor receivers on the implant member in the deployed configuration may be smaller than a circumference defined by a circle passing through at least three locations of the embedded tissue anchors in the tissue prior to a physical coupling between the implant member and the embedded tissue anchors.

At least one of the tissue anchors may include a helical tissue anchor. The at least one of the tissue anchors may include a grapple tissue anchor that may include at least two prongs pivotally coupled to each other, each of the two prongs having a tip shaped to pierce the tissue.

The implant kit may further include a plurality of fasteners, each fastener movable along a respective one of the guide lines to a position where at least some of the fasteners secure the implant member to the tissue under tension in the deployed configuration. Each of the fasteners may include a unidirectional clutch that in use allows the fastener to advance along a respective one of the guide lines toward a respective one of the embedded tissue anchors and prevents the fastener from retreating along the guide line away from the respective embedded tissue anchor. The plurality of fasteners and the implant member may be provided in a unitary structure. The at least some of the fasteners may each be fastenable to a respective one of the guide lines to secure the implant member to the tissue under tension in the deployed configuration. The at least some of the fasteners may each be fastenable to a respective one of the embedded tissue anchors to secure the implant member to the tissue under tension in the deployed configuration.

The implant member may include a plurality of receivers, each of the receivers having at least one of the guidelines passing therethrough, where all of the guidelines passing through a respective one of the receivers extend to a single respective one of the tissue anchors embedded in the tissue.

A tissue anchor system for securing an implant member to tissue within a body during an implant procedure may be summarized as including a tissue anchor comprising plurality of elongated members, each of the elongated members comprising a first end, a second end and an intermediate portion positioned between the first and the second ends, wherein each of the second ends comprises a tip shaped to penetrate the tissue, and the intermediate portions of at least two of the elongate members are pivotably coupled together by a pivot member; and at least one coupler physically coupled to at least one of the elongated members at location on a portion of the at least one of the elongated members extending between the pivot point and the first end of the at least one of the elongated members, the coupler configured to securely couple the tissue anchor to the implant member during the implant procedure.

Each elongated member of the at least two elongated members may include an arcuate shaped portion. Each elongated member of the at least two elongated members may include a portion between the pivot point and the second end of the elongated member that extends along an arcuate path. Each of the second ends may include a barb. The at least one coupler may be physically coupled to each of the at least two elongated members. The at least one coupler may include a flexible line sized to be received through an opening provided in an elongated member of the at least two elongated members. The at least one coupler may include a flexible line sized to be received through a respective opening provided in each elongated member of the at least two elongated members. The at least one coupler may include a plurality of a flexible lines, each of the flexible lines sized to be received through an opening provided in an elongated member of the at least two elongated members. The at least one coupler and the at least one elongated member may be a unitary structure. The at least one coupler may include a flexible line sized to be received though an opening provided in the at least one elongated member and through an opening provided in the implant member.

An opening may be provided in each of one or more of the elongated members, each opening sized to receive a guide line therethrough.

The at least one coupler may include a clamp configured to clamp a portion of the implant member. The at least one coupler may include an extension sized to be received within an opening provided in the implant member. The at least one coupler may include an expansion member configured to expand and grip one or more surfaces of the implant member. The at least one coupler may include a contraction member configured to contract and grip one or more surfaces of the implant member. The at least one coupler may include a detent. Each of the tissue anchor and the coupler may be sized to be delivered percutaneously to the tissue in the body during the implant procedure.

A method of operating a medical device system to constrict an orifice in tissue may be summarized as including positioning a tool having a guide frame with a plurality of guide members such that distal ends of the guide members are at least proximate respective locations about a periphery of an orifice in a tissue internally within a body; actuating the guide members to embed a plurality of tissue anchors in the tissue at least proximate respective ones of the respective locations about the periphery of the orifice in the tissue; advancing an annuloplasty implant member to the tissue along a plurality of guide lines that extend from the embedded tissue anchors; and securing the annuloplasty implant member to the embedded tissue anchors via a plurality of fasteners, the annuloplasty implant secured in an anchored configuration.

The method of operating a medical device system to constrict an orifice in tissue may further include percutaneously delivering the guide frame into the body in a compressed configuration; expanding the guide frame into an uncompressed configuration before positioning the tool such that the distal ends of the guide members are at least proximate their respective locations about the periphery of the orifice; compressing the guide frame after actuating the guide members to embed the plurality of tissue anchors; and percutaneously removing the guide frame from the body after compressing the guide frame.

The method of operating a medical device system to constrict an orifice in tissue may further include percutaneously delivering the annuloplasty implant member into the body in an unanchored configuration after percutaneously removing the guide frame from the body.

Securing the annuloplasty implant member to the embedded tissue anchors via a plurality of fasteners, the annuloplasty implant secured in an anchored configuration may include securing the annuloplasty implant member in an arch shape anchored proximate each of two ends, and proximate a location between the two ends, and percutaneously delivering the annuloplasty implant member into the body in an unanchored configuration comprises percutaneously delivering the annuloplasty implant member in an elongated scallop shape.

The method of operating a medical device system to constrict an orifice in tissue may further include passing the guide lines through respective ones of a number of guide line receivers of the annuloplasty implant member before percutaneously delivering the annuloplasty implant member into the body in an unanchored configuration.

Actuating the guide members to embed a plurality of tissue anchors in the tissue at least proximate respective ones of the respective locations about the periphery of the orifice in the tissue may include embedding the tissue anchors such that a circumference defined by a circle passing through at least three locations of respective ones of the tissue anchors embedded about the periphery of the orifice in the tissue is greater than a circumference defined by a circle passing through at least three locations of the guide line receivers on the annuloplasty member in the anchored configuration. Actuating the guide members to embed a plurality of tissue anchors in the tissue may include actuating the guide members to embed the plurality of tissue anchors having respective ones of the guide lines extending therefrom in the tissue.

Securing the annuloplasty implant member to the embedded tissue anchors via a plurality of fasteners, the annuloplasty implant secured in an anchored configuration may include advancing each fastener along a respective one of the guide lines into contact with a respective portion of the annuloplasty implant member. Securing the annuloplasty implant member to the embedded tissue anchors via a plurality of fasteners, the annuloplasty implant secured in an anchored configuration may include advancing each fastener having a unidirectional clutch along a respective one of the guide lines.

Actuating the guide members to embed a plurality of tissue anchors in the tissue at least proximate respective ones of the respective locations about the periphery of the orifice in the tissue may include extending a respective inner tube of each of the guide members from a lumen of a respective outer tube of each of the guide members, the inner tube advancing a respective one of the tissue anchors into the tissue.

The method of operating a medical device system to constrict an orifice in tissue may further include withdrawing the inner tube of each of the guide members away from a respective one of the tissue anchors embedded in the tissue to expose at least one barb of the tissue anchor to the tissue.

The method of operating a medical device system to constrict an orifice in tissue may further include retracting the inner tube of each of the guide members into the lumen of the outer tube of the respective one of the guide members while at least maintaining a position of the guide wire extending from a respective one of the tissue anchors with respect to the tissue.

An annuloplasty implant may be summarized as including at least three arcuate segments coupled to one another by respective ones of a number of articulation joints to form an articulated structure, each of the arcuate segments arcuate about a respective axis, the articulated structure having a first end and a second end, a first guide line receiver proximate the first end, a second guide line receiver proximate the second end, and at least a third guide line receiver between the first and the second guide line receivers, the first, the second and at least the third guide line receivers each sized to receive a respective guide line to a respective tissue anchor, the articulated structure configurable between an anchored configuration in which the arcuate segments are arranged with respect to one another in an arcuate shape structure which is arcuate about an axis that is parallel to the respective axes of the arcuate segments, the arcuate shape structure having an anchored maximum longitudinal dimension and an anchored maximum lateral dimension, and an unanchored configuration in which the arcuate segments are arranged with respect to one another in an elongated scallop shape structure that has an unanchored maximum longitudinal dimension and an unanchored maximum lateral dimension, the unanchored maximum longitudinal dimension greater than the anchored maximum longitudinal dimension and the anchored maximum lateral dimension greater than the unanchored maximum lateral dimension.

The articulation joints may be hinges that pivotally couple successively neighboring ones of the arcuate segments together in at least the unanchored configuration. The arcuate segments may each include a stop that interacts with a complimentary stop on an adjacent one of the arcuate segments. A pin of each hinge may be offset from a longitudinal centerline of at least one of the arcuate segments coupled by the hinge. The articulation joints may be flexure joints that pivotally couple successively neighboring ones of the arcuate segments together in at least the unanchored configuration. At least one respective recess between each pair of adjacent ones of the arcuate segments may define each of the respective flexure joints.

The arcuate segments may be configured to be mounted directly to tissue comprising a mitral valve via a plurality of tissue anchors and guide lines that apply force to at least some of the arcuate segments as the annuloplasty implant transitions from the unanchored configuration to the anchored configuration, the articulated structure sufficiently rigid when in the anchored configuration to affect a shape of the mitral valve.

The annuloplasty implant may further include at least three fasteners, the fasteners each having an aperture sized to receive a respective guide line, and the fasteners sized to not be received through the guide line receivers of the arcuate segments.

The arcuate segments may include at least one of a textured surface, a tissue scaffold or a therapeutic eluting layer. The articulated structure may be configured to be coupled directly to a plurality of tissue anchors embedded in tissue comprising an orifice, and wherein the articulated structure may include at least three tissue anchor receivers, each of the at least three tissue anchor receivers configured to physically couple with a respective one of the tissue anchors, and wherein a circumference defined by a circle passing through at least three locations of the at least three tissue anchor receivers on the articulated structure in the anchored configuration is smaller than a circumference defined by a circle passing through at least three locations of the embedded tissue anchors in the tissue prior to a physical coupling between the articulated structure and the embedded tissue anchors.

Various systems and methods may include combinations and subsets of those summarized above.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

FIG. 22A is an isometric view of a fastener that fastens a guide line to a tissue anchor, according to another illustrated embodiment FIG. 22B is a cross-sectional view of the fastener, guide line and tissue anchor of FIG. 22A.

FIG. 22C is an isometric view of an implant member that has single piece, unitary part fasteners that fastens a guide line to a tissue anchor, according to another illustrated embodiment

DETAILED DESCRIPTION

In the following description, certain specific details are set forth in order to provide a thorough understanding of various embodiments of the invention. However, one skilled in the art will understand that the invention may be practiced without these details. In other instances, well-known structures have not been shown or described in detail to avoid unnecessarily obscuring descriptions of the embodiments of the invention.

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings provided herein are for convenience only and do not interpret the scope or meaning of the claimed invention.

Overview of Device and Orifice Constriction Methods

Various embodiments of medical apparatus which are percutaneously or intravascularly deployed and may be used for constricting a bodily orifice are described herein.

Figure 1:
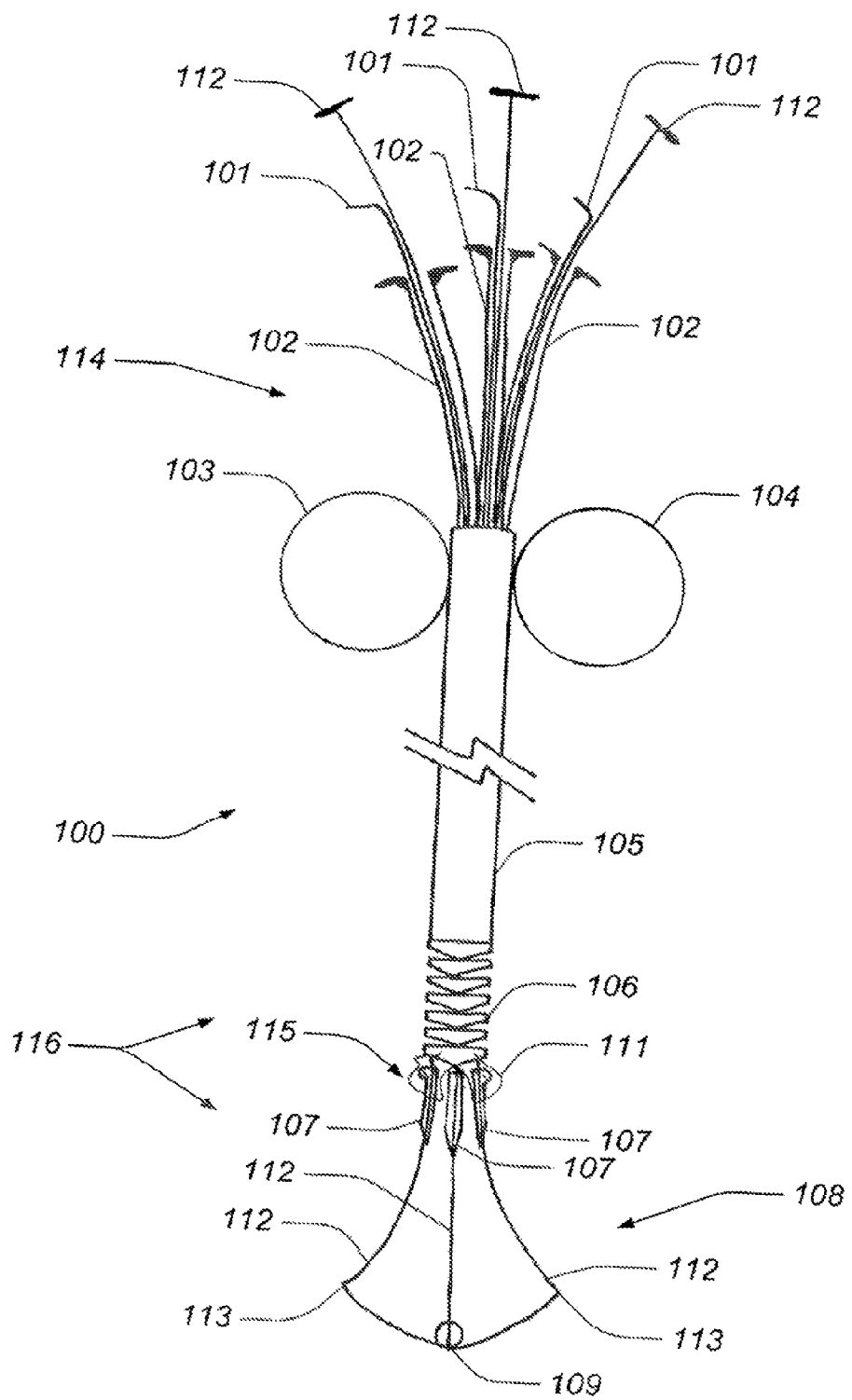
FIG. 1 is a schematic diagram of a medical device system according to one illustrated embodiment, including an implantable device and a tool with a control handle, tissue anchors, and anchor guide mechanism that is operable to implant the implantable device.

FIG. 1 shows a medical device system 100 including an implantable device 115 and tool 116 to implant the implantable device 115, according to one illustrated embodiment.

The tool 116 of the medical device system 100 may be used to deploy the implantable device 115 having tissue anchors 107 and a flexible cable 111. The tissue anchors 107 may be secured to the annulus of an orifice and the flexible cable 111 may be used to constrict the orifice by pulling the anchors 107 inward. The tool 116 of the medical device system 100 comprises a flexible anchor guide frame 108 that may be used to guide tissue anchors 107 of the implantable device to target positions on the orifice annulus. The anchor guide frame 108 may be made of a material such as Nitinol. The anchor guide frame 108 shown in FIG. 1 is comprised of three guide members, for instance guide wires 112,—one guide member for each of the tissue anchors 107 shown. The guide frame 108 may include a different number of guide members or arms (e.g., guide wires or guide rails) if more tissue anchors are desired. The guide members 112 shown preferably have hinges 113 and may be connected with small loops 109. The hinges 113 and loops 109 enable the guide frame 108 to fold up to fit inside a catheter and to expand to extend across an orifice. Both the hinges 113 and loops 109 may be replaced by other mechanisms or structures that enable bending or compression. The tool 116 of the medical device system 100 typically has an articulation mechanism 106 (e.g., a plurality of articulation joints) that enables correctly orienting the anchor guide frame 108 during deployment of tissue anchors 107. The articulation mechanism 106 is preferably able to bend in any direction. The tool 116 of the medical device system 100 may include control knobs 103 and 104 which may be used to control the bending of the articulation mechanism 106 via cables that are carried in long flexible tube 105.

Long flexible tube 105 extends from the articulation mechanism 106 to a medical device control mechanism 114 located at a proximal end of the catheter. Control mechanism 114 may include control knobs 103 and 104, elongated release members (e.g., rods or wires) 101, push tubes 102, and guide wires 112. Additional controls may be included in other embodiments. The flexible tube 105 may have multiple lumens. Multi-lumen push tubes 102, guide members (e.g., guide wires) 112, release members 101, cable 111, and other mechanisms may be carried in flexible tube 105. In the illustrated embodiment, each push tube 102 has two lumens. A guide wire 112 is carried in a first lumen and a release member 101 is carried in a second lumen. Anchors 107 are attached at distal tips of release members 101. The tissue anchor 107 may be inserted into the annulus of an orifice by advancing the push tube 102 along the guide member 112 and advancing or rotating the release member 101 carried in the push tube 102 at the same rate. The tissue anchor 107 may advance past the hinge 113 and embed into the annulus of the orifice to be constricted while in an unretracted configuration. Once the tissue anchor 107 is embedded, the release member 101 attached to the anchor may be retracted while the push tube 102 is held in place in a retracted configuration. Retraction of the release member 101 causes the tissue anchor 107 to detach from the distal tip of the release member 101 and remain embedded in the tissue at least proximate a desired location. Other embodiments may use different methods and/or structures to release the tissue anchors 107.

Figure 2:
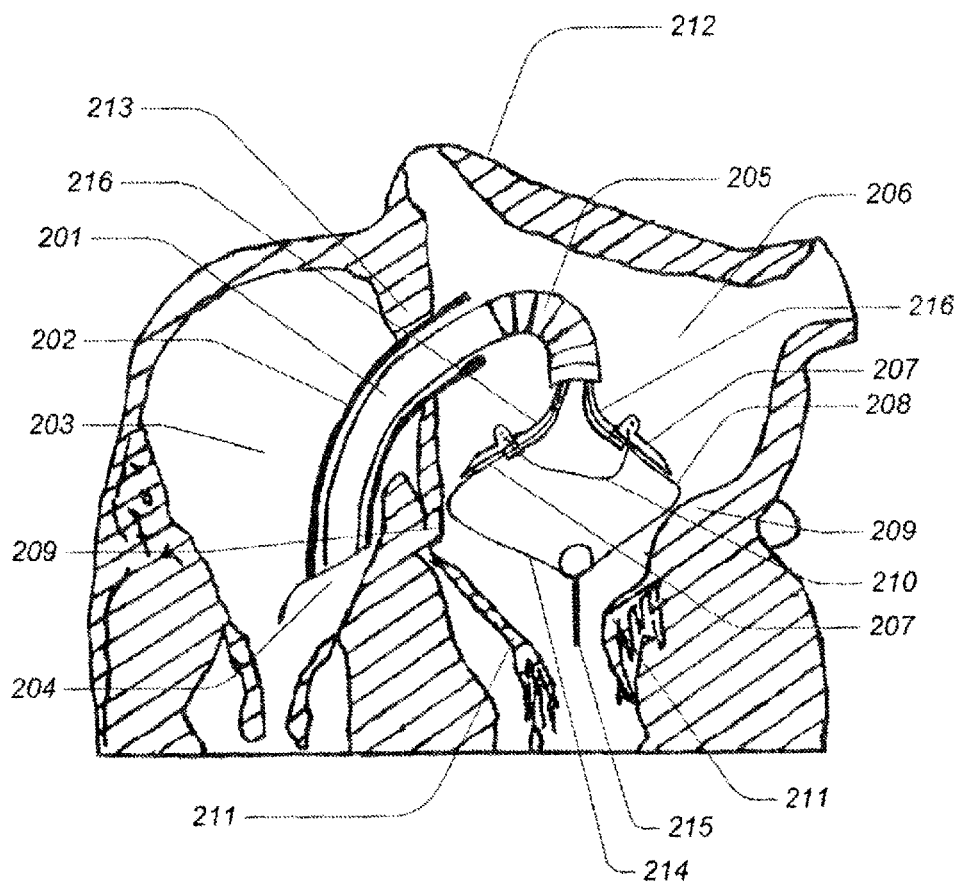
FIG. 2 is a cutaway diagram of a heart showing an implantable medical device implanted in tissue therein according to one illustrated embodiment, the implantable device percutaneously placed in a left atrium of the heart.

FIG. 2 shows an implantable device 207, 210 implanted in a portion of a heart to constrict a bodily orifice, for example a mitral valve of the heart, according to one illustrated embodiment.

A portion of the medical device system 100 may be percutaneously and/or intravascularly inserted into a portion of a heart 212, for example in a left atrium 206 of the heart 212. In this example embodiment, a flexible anchor guide frame 214 and implantable device are delivered via a catheter 202 inserted via the inferior vena cava 204 and penetrating the transatrial septum 213 from a right atrium 203. The catheter 202 is preferably less than 8 mm in diameter.

The flexible anchor guide frame 214 expands after being delivered via the catheter 202 into a shape that preferably enables the tissue anchors 207 of the implantable device to be delivered to the desired respective positions on the mitral annulus 209. The flexible anchor guide frame 214 may be moved into the correct orientation by adjusting a shape of an articulation mechanism 205, advancing or retracting flexible tube 201, or rotating flexible tube 201. The flexible anchor guide frame 214 preferably has an overall shape that enables the frame to take on a desired orientation within a cavity by conforming to the shape or being affected by the movement of anatomical features. Such a property is known as "self-locating". Minimal insertion force and operator guidance is typically needed to properly position the anchor guide mechanism. The flexible anchor guide frame 214 may also have specific features which cause the flexible anchor guide frame 214 to orient correctly based on the position of an anatomical feature, such as the mitral valve cusps or leaflets 211. An example of such a feature is alignment fin 215. Alignment fin 215 is attached rigidly to flexible anchor guide frame 214 and shaped so that it may be deflected to a particular orientation by an anatomical feature, such as mitral valve leaflets 211. As the flexible anchor guide frame 214 is advanced toward an anatomical feature, such as the mitral valve annulus 209, the shape or motion of an anatomical feature, such as the mitral valve leaflets 211, may cause alignment fin 215, and thus attached flexible anchor guide frame 214, to rotate or translate to a desired orientation or location.

The tissue anchors 207 may be inserted into the annulus 209 by advancing the push tubes 216 along the guide members (e.g., guide wires or rails) 112. The tissue anchors 207 may advance past the bend 208 and embed into the annulus 209. The embedded tissue anchors 207 may then be released from the push tubes 216. The flexible cable 210 connecting the tissue anchors 207 may then be tightened and secured to constrict the mitral annulus 209.

Figure 3:
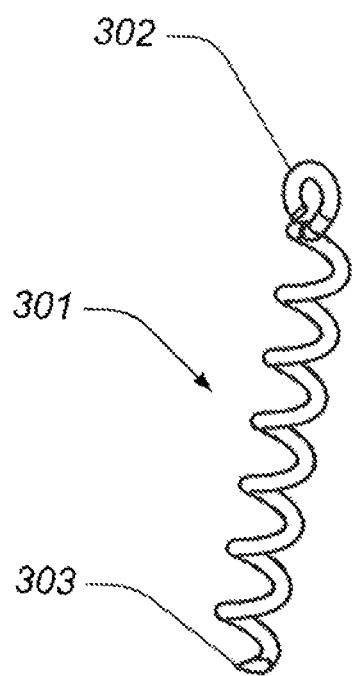
FIG. 3 is a diagram showing an example of a helical tissue anchor according to one illustrated embodiment.

FIG. 3 shows an example of a tissue anchor according to one illustrated embodiment.

The tissue anchor 301 has a helical structure with sharp tip 303, and hence is denominated as a helical tissue anchor 301. Loop 302 may be used to connect to a structure to hold the tissue anchor 301 to a release rod. Loop 302 may also be used to attach tissue anchor 301 to a cable used for cinching the annulus of a bodily orifice.

Figures 4A, 4B:
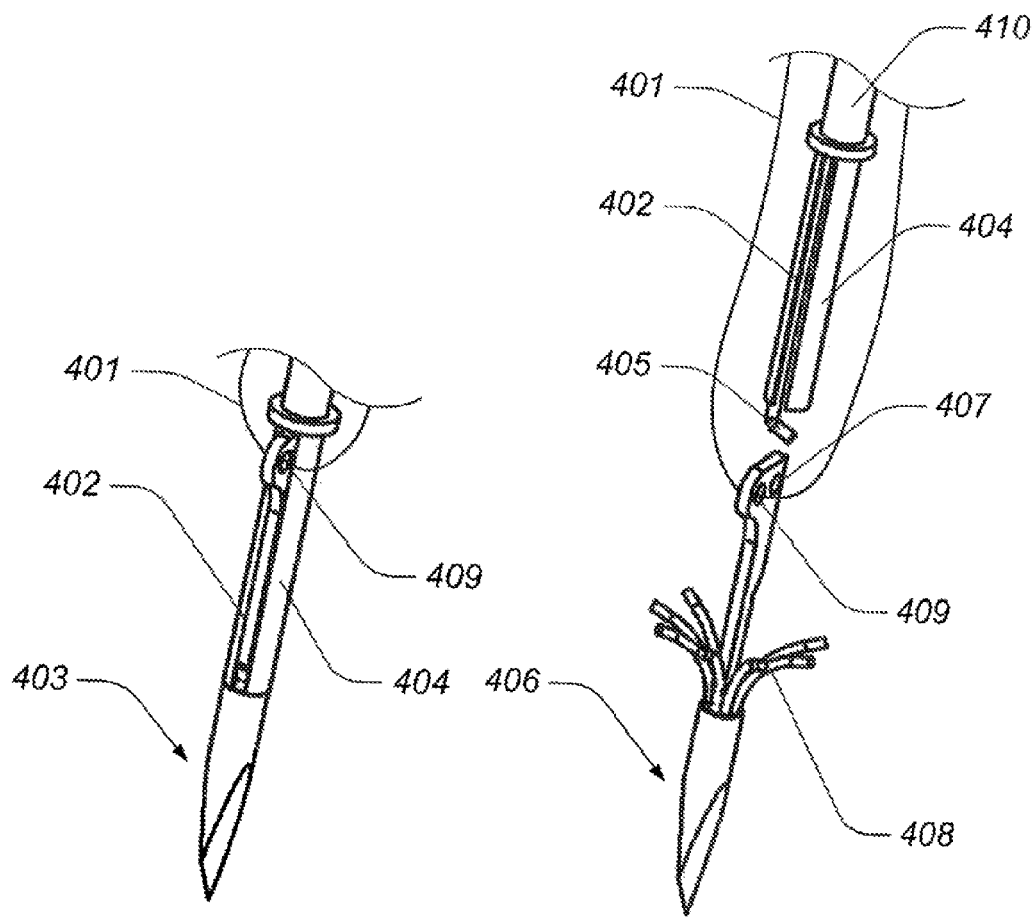
FIG. 4A is an isometric partial view showing an example of a multi-barbed tissue anchor with resilient barbs retained by a constriction tube according to one illustrated embodiment.
FIG. 4B is an isometric partial view showing an example of a multi-barbed anchor with the resilient barbs free of the constriction tube and exposed.

FIGS. 4A and 4B show an example of a tissue anchor according to one illustrated embodiment.

In particular, FIG. 4A shows the tissue anchor 403 in a compressed configuration, while FIG. 4B shows the tissue anchor 406 in an expanded configuration. The tissue anchors 403, 406 comprise multiple barbs 408 (not shown in FIG. 4A), which may be resilient. The multiple barbs 408 may be compressed into constriction tube 404 as shown for tissue anchor 403. Compression of barbs 408 into constriction tube 404 enables the anchor to move more readily through a catheter and also to be inserted more readily into tissue without causing damage to the tissue.

Tissue anchor 403 may include a hole 409 that may be used to attach the anchor to a cable 401 used for cinching the annulus of a bodily orifice. Constriction tube 404 may include a slot 402 to allow anchor 403 to be ejected from constriction tube 404 in the case where hole 409 is mounted on a protruding flange.

Tissue anchor 406 may include a hole 407 that may be used to connect said anchor to release rod 405. Release rod 405 may be carried in a lumen of push tube 410. If constriction tube 404 is extended over hole 407 as shown for anchor 403, release rod 405 is held captive in hole 407 by the wall of tube 404. If constriction tube 404 is retracted so as to not cover hole 407, as shown for tissue anchor 406, release rod 405 is not held captive in hole 407 and said tissue anchor may become disconnected from constriction tube 404 and release rod 405.

Tissue anchor 406 may be disconnected from release rod 405 and barbs 408 may be uncompressed by retracting constriction tube 404 relative to the release rod 405 and tissue anchor 406. Retracting constriction tube 404 past the tips of barbs 408 causes said barbs to be released and resiliently expand. Retracting constriction tube 404 past hole 407 may release tissue anchor 406.

FIGS. 5A-5E show examples of five types of tissue anchors embedded in tissue.

Figures 5A, 5B:
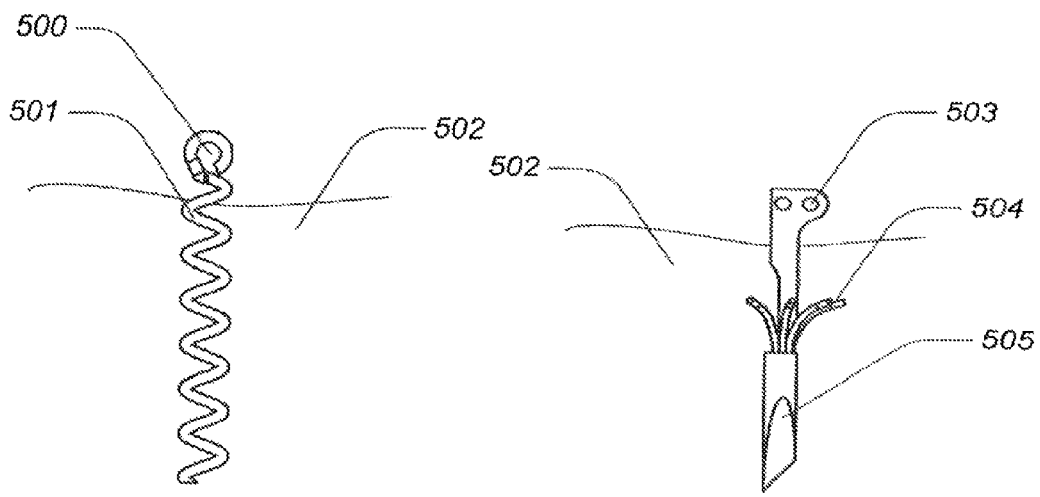
FIG. 5A is front elevational view showing a helical tissue anchor embedded in tissue according to one illustrated embodiment.
FIG. 5B is front elevational view showing a barbed tissue anchor embedded in tissue according to one illustrated embodiment.
Figure 5C:
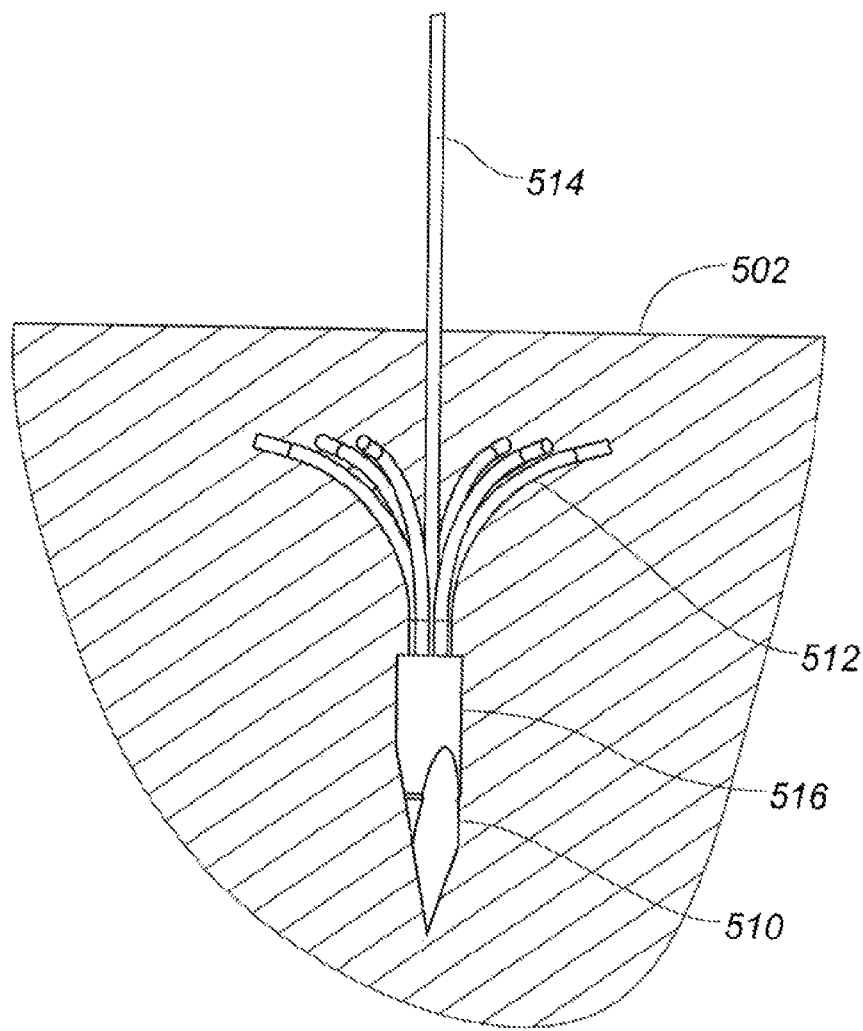
FIG. 5C is front elevational view showing a barbed tissue anchor with an integral guide line such as a guide wire according to another illustrated embodiment, the tissue anchor embedded in tissue.
Figure 5D:
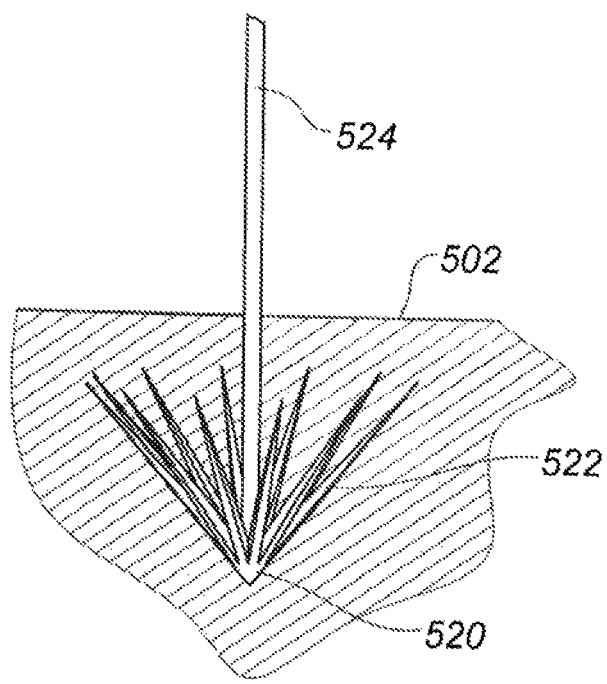
FIG. 5D is front elevational view showing a barbed tissue anchor with a unitary guide line such as a guide wire according to a further illustrated embodiment, the tissue anchor embedded in tissue.

In particular, FIG. 5A shows a helical anchor 501 embedded in tissue 502. The helical tissue anchor 501 is embedded in tissue 502 by rotating the helical tissue anchor 501 about is longitudinal axis. FIG. 5B shows a multi-barbed anchor 505 embedded in tissue 502. The multi-barbed tissue anchor 505 is embedded in tissue 502 by pushing the anchor into the tissue. Barbs 504 provide resistance to restrict the tissue anchor 505 from being extracted. FIG. 5C shows a tissue anchor 510 with multiple barbs 512 (only one called out in FIG. 5C) and an integral guide line or guide wire 514 embedded in tissue 502. The barbs 512 and guide line 514 may be secured in a shell 516 of the tissue anchor 510. For example, the barbs 512 and guide line or guide wire 514 may be secured via swaging. The guide line 514 may take a variety of forms, for example a metal wire such as Nitinol. FIG. 5D shows a tissue anchor 520 with multiple barbs 522 (only one called out in FIG. 5D) and a unitary guide line or guide wire 524 embedded in tissue 502. In contrast to the embodiment of FIG. 5C, the embodiment of FIG. 5D forms the tissue anchor 520 and guide line or guide wire 524 from a single piece of material, for instance a thin flexible metal wire, which is selected from metals that are biocompatible (e.g., stainless steel, Nitinol).

Figure 5E:
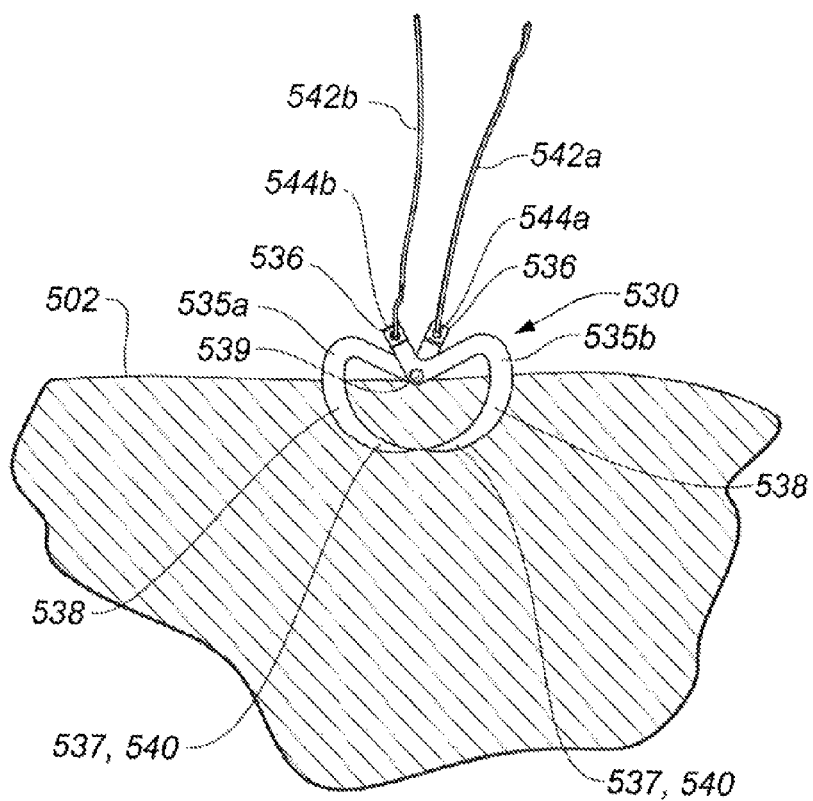
FIG. 5E is front elevational view showing a grapple tissue anchor embedded in tissue according to one illustrated embodiment.

FIG. 5E shows a grapple tissue anchor 530 implanted into tissue 502. Grapple tissue anchor 530 includes a plurality of elongated members 535. At least two of the elongated members (i.e., first elongated member 535*a* and second elongated member 535b in this example embodiment) are pivotably coupled together by pivot member 539. Each of the elongated members 535 includes a first end 536, a second end 537, an intermediate portion 538 and a respective length along the elongated member 535 extending between the first end 536 and the second end 537. Each second end 537 includes a tip 540 shaped to penetrate tissue 502. In some example embodiments, each second end 537 includes a barb. In this example embodiment, each of the elongated members 535 is an arcuate elongated member. In this example embodiment, each of the elongated members 535 forms a prong. Pivot member 539 allows the elongated members 535 to pivot with respect to one another to space tips 540 apart from one another into a configuration advantageous for penetrating tissue 502. Upon further deployment of grapple tissue anchor 530 into tissue 502, the elongated members 535 are pivoted to draw tips 540 towards each other which causes tips 540 to travel along a path through tissue 502 such that tips 540 are positioned closer to one another than during their initial deployment into tissue 502. This allows grapple tissue anchor 530 to firmly anchor itself into tissue 502. In this example embodiment, the plurality of elongated members 530 is physically coupled to a plurality of flexible lines 542a and 542b (collectively 542). Specifically, flexible line 542a is coupled to elongated member 535a and flexible line 542b is physically coupled to elongated member 535b. In this example embodiment, elongated member 535a includes an opening 544a sized to receive flexible line 542a and elongated member 535b includes an opening 544b sized to receive flexible line 542b. In some example embodiments, a single flexible line 542 is received in an opening provided in each of the elongate members 535. In this example embodiment, the flexible lines 542 are guide lines. In some example embodiments, the flexible lines 542 and respective ones of the elongate members 535 are provided as a unitary structure.

Figures 6A, 6B:
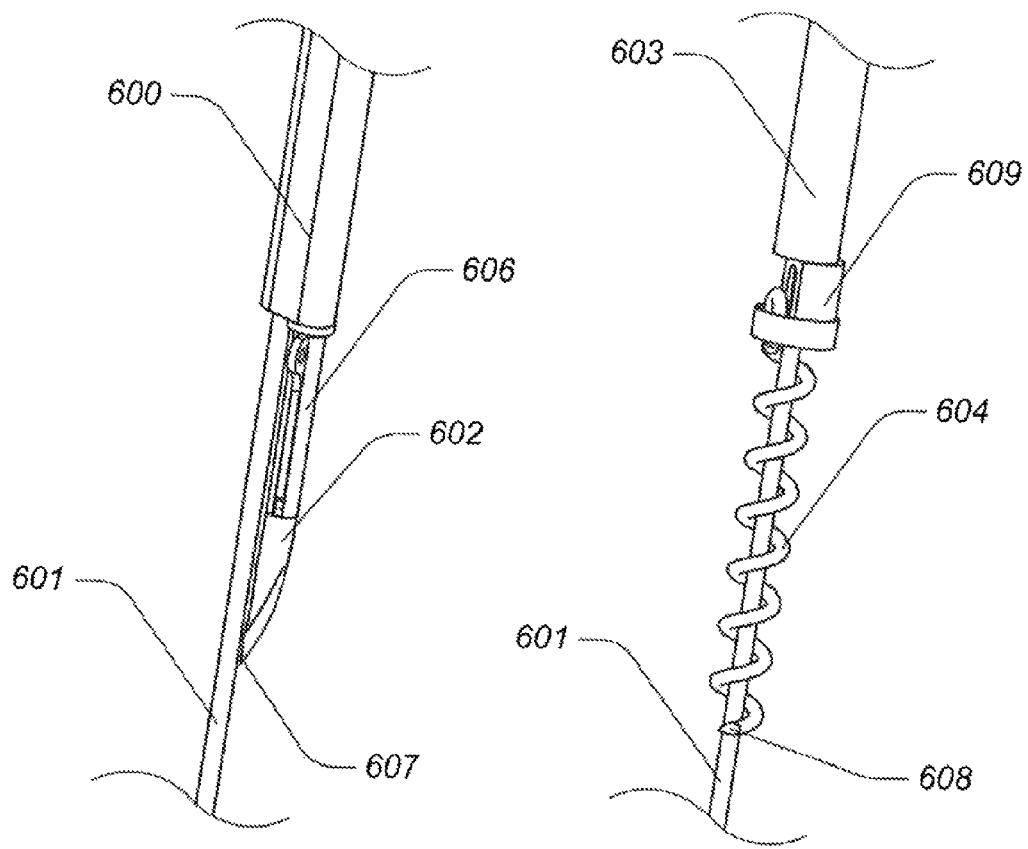
FIG. 6A is an elevational view showing a tissue anchor movably received on a guided member according to one illustrated embodiment.
FIG. 6B is an elevational view showing a tissue anchor movably received on a guided rail according to another illustrated embodiment.

FIGS. 6A and 6B show examples of tissue anchors guided by a guide member in the form of a guide rail.

In particular, FIG. 6A shows a multi-lumen push tube 600 that may slide over a guide rail 601. Tissue anchor 602 may be temporarily attached to multi-lumen push tube 600 by constriction tube 606 and a release rod (not shown). Sliding push tube 600 along guide rail 601 enables tissue anchor 602 to be controllably delivered to a location proximate to guide rail 601. Tissue anchor 602 may be constructed or oriented in such a way that tissue anchor tip 607 slides along or very near to guide rail 601. Such orientation or construction enables the tip to be protected from obstructions in the catheter or body that may dull the tip. Also, such orientation or construction protects areas of tissue proximate the guide rail from inadvertent, damaging contact with the sharp tip 607 of tissue anchor 602.

FIG. 6B shows a single-lumen push tube 603 that may slide over guide rail 601. Helical tissue anchor 604 also may slide over guide rail 601 and may be temporarily attached to single-lumen push tube 603 by latch mechanism 609. Latch mechanism 609 may be fastened to tissue anchor 604 by a friction fitting that is released under sufficient axial force. This assembly enables tissue anchor 604 to be controllably delivered to a location proximate to guide rail 601. Tissue anchor 604 may be constructed or oriented in such a way that tissue anchor tip 608 slides along or very near to guide rail 601. Such orientation or construction enables the tip of the tissue anchor 604 to be protected from obstructions in the catheter or body that may dull the tip. Also, such orientation or construction protects areas of tissue proximate the guide rail 601 from inadvertent, damaging contact with the sharp tip of tissue anchor 608.

While FIGS. 6A and 6B show examples of two particular types of tissue anchors being guided by a rail, it will be apparent to those skilled in the art that many other types of tissue anchors could also be deployed with the aid of a guide rail as well.

Figures 7A, 7B, 7C:
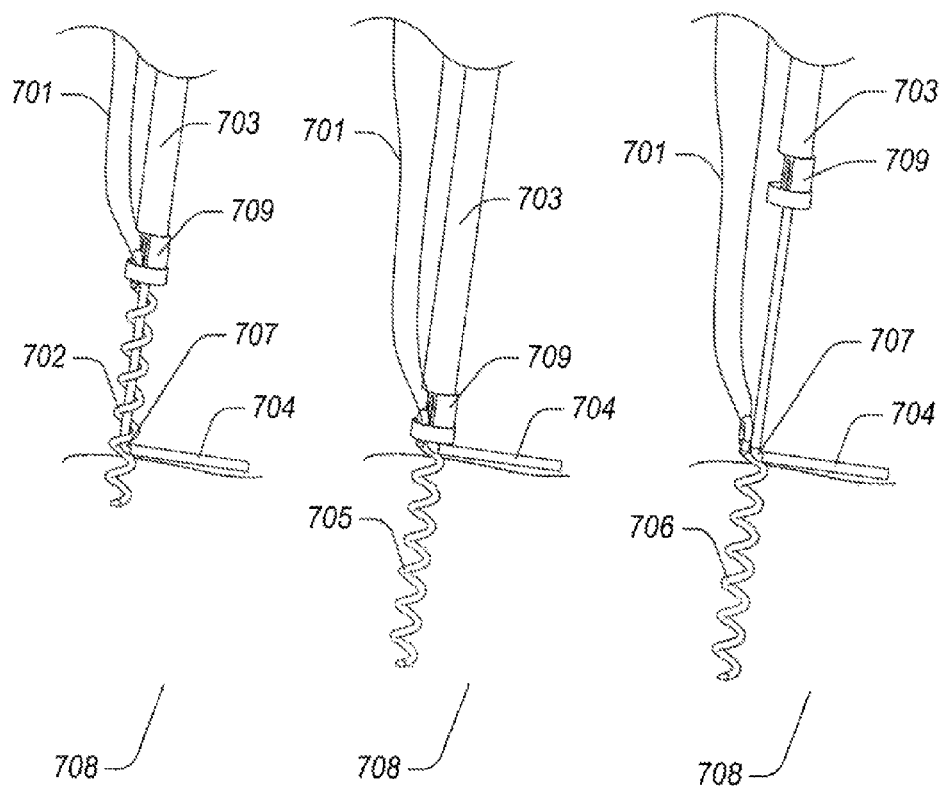
FIGS. 7A-7C are sequential elevational views showing a helical tissue anchor movably received on a guided member penetrating tissue at three successive intervals of time according to one illustrated embodiment.

FIGS. 7A-7C illustrates deployment of helical tissue anchors implanted or embedded in tissue according to one illustrated embodiment.

In particular, FIG. 7A shows a helical tissue anchor 702 partially deployed into tissue 708. The location that tissue anchor 702 enters the tissue may be determined by the position of a guide member, for instance guide rail 704. Bend 707 in guide rail 704 may be positioned at the approximate location where the tissue anchor 702 is to be deployed into the tissue. Bend 707 in guide rail 704 may comprise a hinge, a flexure, or one of many other joints. Tissue anchor 702 is deployed by rotating push tube 703. The rotation of tissue anchor 702 at the position of the bend 707 causes tissue anchor 702 to spiral off guide rail 704 and into tissue 708.

FIG. 7B shows a helical tissue anchor 705 fully deployed into tissue 708, but still connected to latch mechanism 709. In the fully deployed position, helical tissue anchor 705 may no longer wrap around guide rail 704. When still connected to latch mechanism 709, the helical tissue anchor 705 may be readily retracted by counter-rotating push tube 703.

FIG. 7C shows a helical tissue anchor 706 fully deployed into tissue 708 and disconnected from to latch mechanism 709. Latch mechanism 709 may become disconnected from tissue anchor 706 by retracting push tube 703 or releasing latch mechanism 709 with the addition of another cable to trigger a release mechanism.

Figure 8A:
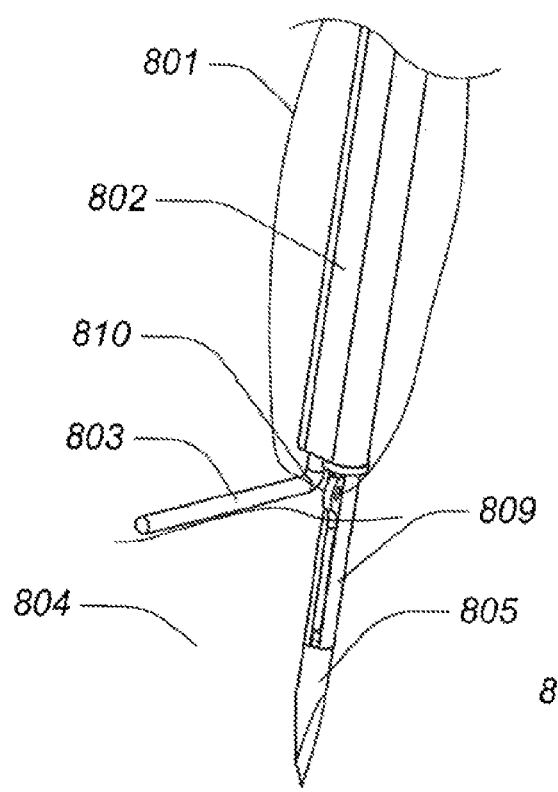
FIGS. 8A and 8B are sequential elevational views showing a multi-barbed tissue anchor movably received on a guided member penetrating tissue at two successive intervals of time according to one illustrated embodiment.
Figure 8B:
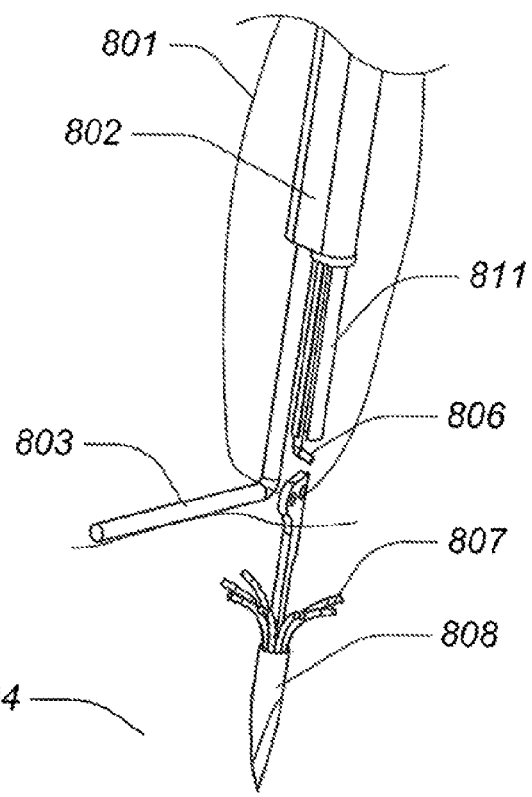

FIGS. 8A and 8B show deployment of multi-barbed tissue anchors in tissue according to one illustrated embodiment.

In particular, FIG. 8A shows a multi-barbed tissue anchor 805 fully inserted into tissue 804, but still encapsulated or retained by constriction tube 809. The location that the multi-barbed tissue anchor 805 enters the tissue may be determined by the position of a guide member, for instance guide rail 803. A bend 810 in guide rail 803 may be positioned at the approximate location where the multi-barbed tissue anchor 805 is to be deployed into the tissue 804. The bend 810 in guide rail 803 may be constructed using a hinge, a flexure, or one of many other methods. The multi-barbed tissue anchor 805 is deployed by advancing push tube 802 over guide rail 803. If encapsulated or retained by constriction tube 809, multi-barbed tissue anchor 805 may be readily retracted by retracting push tube 802.

FIG. 8B shows a multi-barbed tissue anchor 808 fully inserted into tissue 804, but disconnected from constriction tube 811 and release member 806. The multi-barbed tissue anchor 808 is preferably retracted slightly before release member 806 is disconnected in order to cause barbs 807 to expand. The multi-barbed tissue anchor 808 may be disconnected from release member 806 and barbs 807 may be expanded by retracting constriction tube 809 relative to the release member 806 and multi-barbed tissue anchor 808. Retracting constriction tube 811 past the tips of barbs 807 causes the resilient barbs to be released and expand.

FIGS. 8C through 8F show a tissue anchor 820 movably guided to tissue 824 and penetrating the tissue 824 at four successive intervals of time, according to one illustrated embodiment.

Figure 8C:
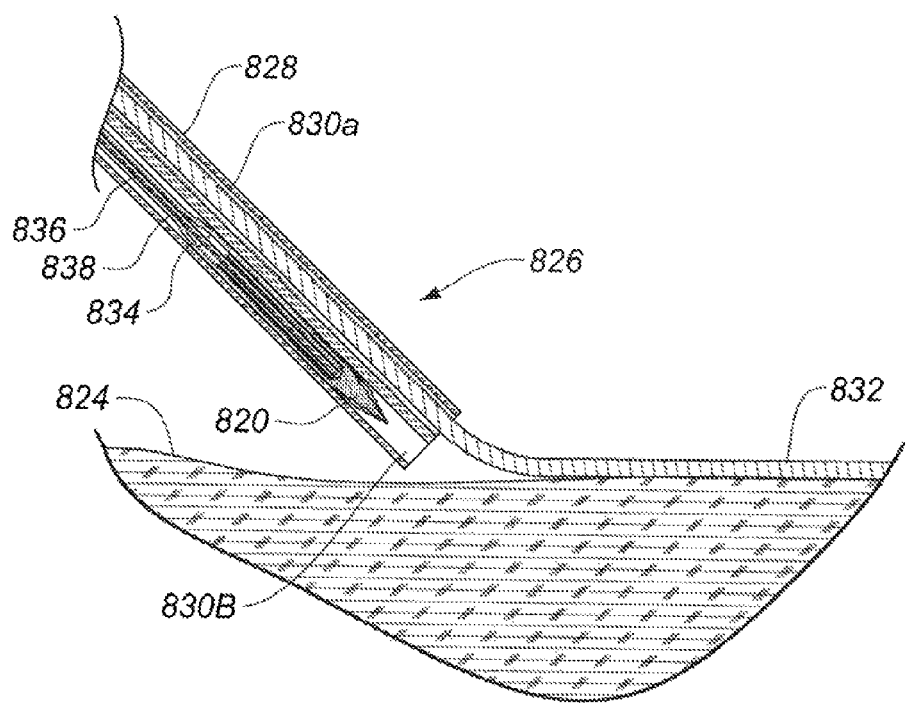
FIGS. 8C through 8F are sequential elevational views showing a multi-barbed tissue anchor movably guided via a guided member penetrating tissue at four successive intervals of time according to one illustrated embodiment.

In particular, FIG. 8C shows a guide member portion of an anchor guide frame 826 of a tool initially contacting the tissue 824.

The guide member portion of the anchor guide frame 826 includes an outer tube 828 having two lumens 830a, 830b.

The guide member portion includes an engagement or locating member 832. The engagement or locating member 832 is used to physically engage the tissue 824 such that the anchor guide frame 826 is at a desired location and orientation in a bodily organ. The engagement or locating member 832 is movingly carried in one lumen 830a of the outer tube 828. The anchor guide frame 826 includes an inner or guide tube 834 movingly received in the other lumen 830b of the outer tube 828. The guide tube 834 functions to guide the tissue anchor 820 to a desired location on the tissue 824. A lumen 836 of the guide tube 834 carries a guide wire 838. The guide wire 838 is a thin flexible wire, for example a thin Nitinol wire. The guide wire 838 may include a lubricous coating or layer, such as polytetrafluoroethylene. The guide tube 834 provides lateral support for the guide wire 838 and retains barbs 840 if the tissue anchor 820 is in a protected, contracted configuration. A butt end of the guide tube 834 may physically engage or bear against an end or lip of the tissue anchor 820. Thus, when the guide tube 834 and guide wire are pushed, the motion is effectively delivered to the tissue anchor 820, which will advance out of the outer tube 828 along with the inner or guide tube 834. The guide tube 834 may optionally be reinforced with one or more wires, for instance Nitinol wires. The guide wire 838 is attached to the tissue anchor 820 and functions as a guide line for an implant member (not shown in FIGS. 8C-F), as described in detail further below.

Figure 8D:
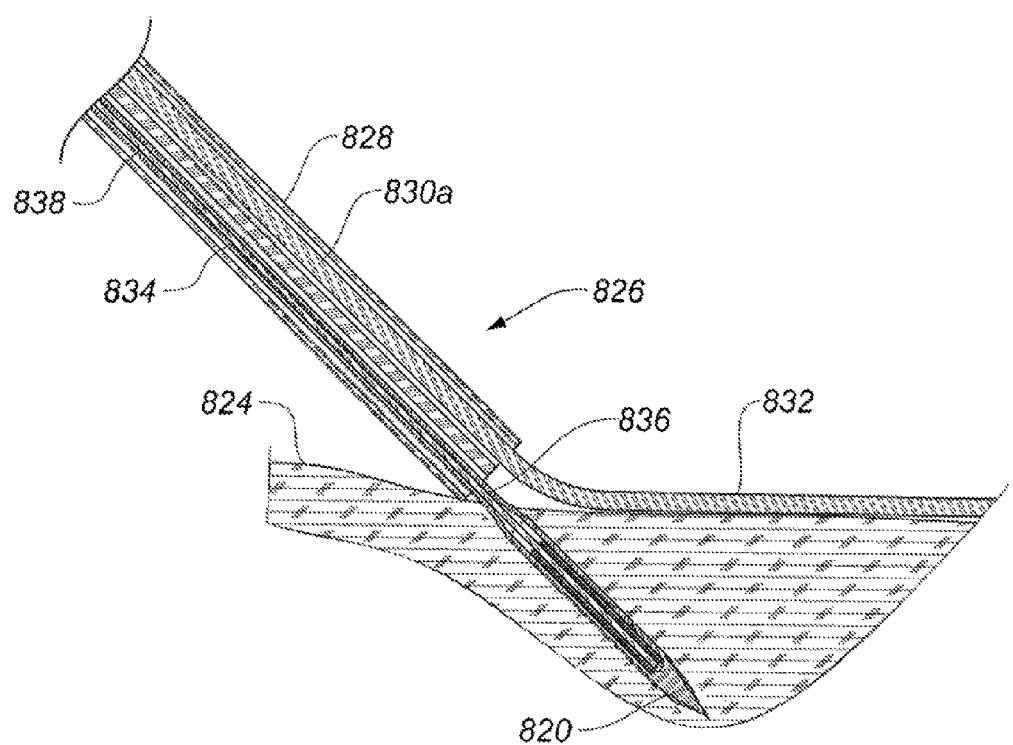
Figure 8E:
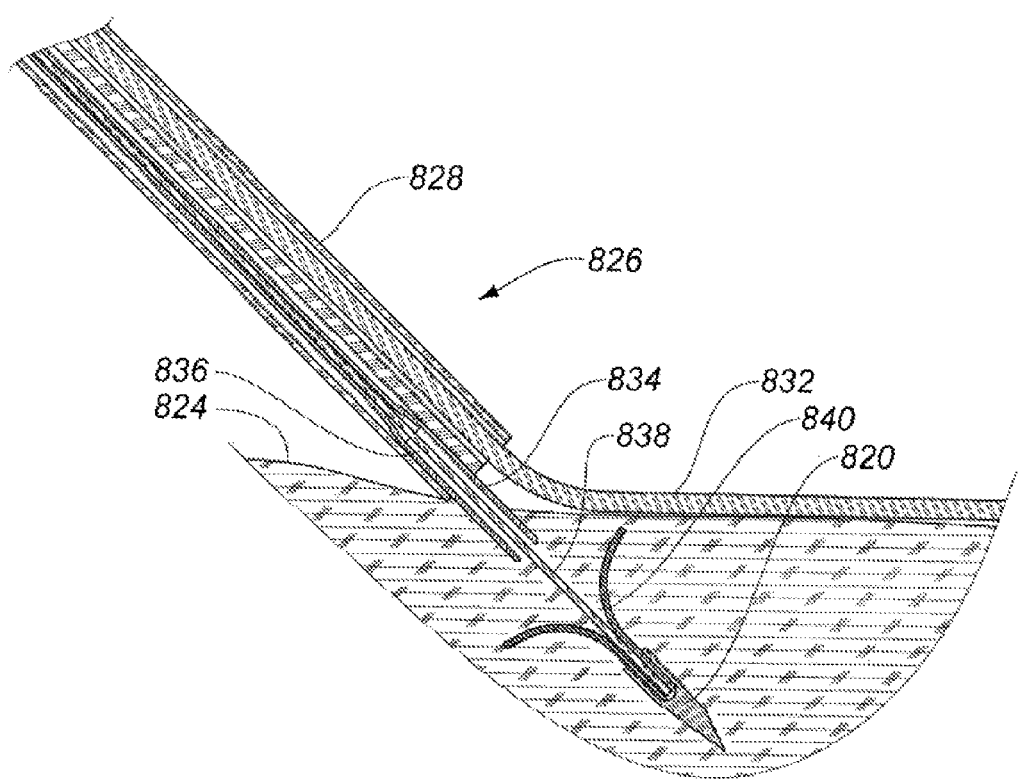

In particular, FIG. 8D shows the tissue anchor 820 being embedded in the tissue 824, along with a portion of the guide tube 834 and guide wire 838. FIG. 8E shows the guide tube 834 partially withdrawn from around the tissue anchor 820, exposing the barbs 840 of the tissue anchor 820. In going from FIG. 8D to FIG. 8E, the guide wire 838 is pushed relatively toward the tissue 824 while the guide tube 834 is pulled or drawn away from the tissue 824. Pushing the guide wire 838 supplies enough force to retain the tissue anchor 820 in the tissue 824 against any force exerted by way of withdrawal of the guide tube 834. As the guide tube 834 clears the barbs 840, the barbs 840 expand due to the resiliency of the material from which the barbs 840 are fashioned. The tissue anchor 820 is thus secured within the tissue 824.

Figure 8F:
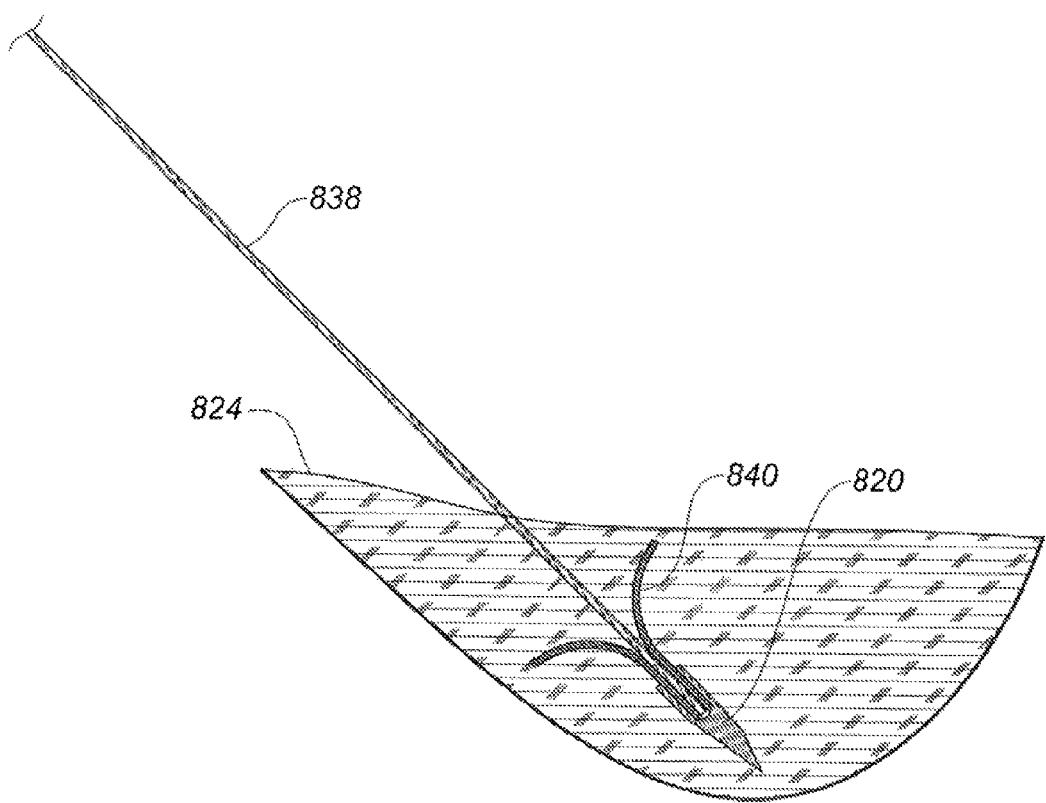

FIG. 8F shows the tissue anchor 820 and guide wire 838 which remain after the portion of the anchor guide frame 826 is withdrawn. The guide tube 834 may be fully retracted into the lumen 830b of the outer tube or catheter 828 prior to withdrawal of the anchor guide frame 826 from the bodily organ. As explained in detail below, the guide wire 838 may be used to guide an implant member (e.g., annuloplasty ring) to the tissue 824, and/or to secure the implant member to the tissue 824 at a desired position and orientation.

While illustrated with two tubes per anchoring location, some embodiments may employ three tubes per anchoring location or more. Using only two tubes per anchoring location advantageously increases the flexibility of the catheter(s) relative to embodiments employing more than two tubes per anchor location. Such eases the movement of the catheter through the bodily lumen (e.g., artery). Such may also allow the use of catheters with smaller diameters than would otherwise be necessary to accommodate one or more additional tubes per anchoring location.

Figure 9:
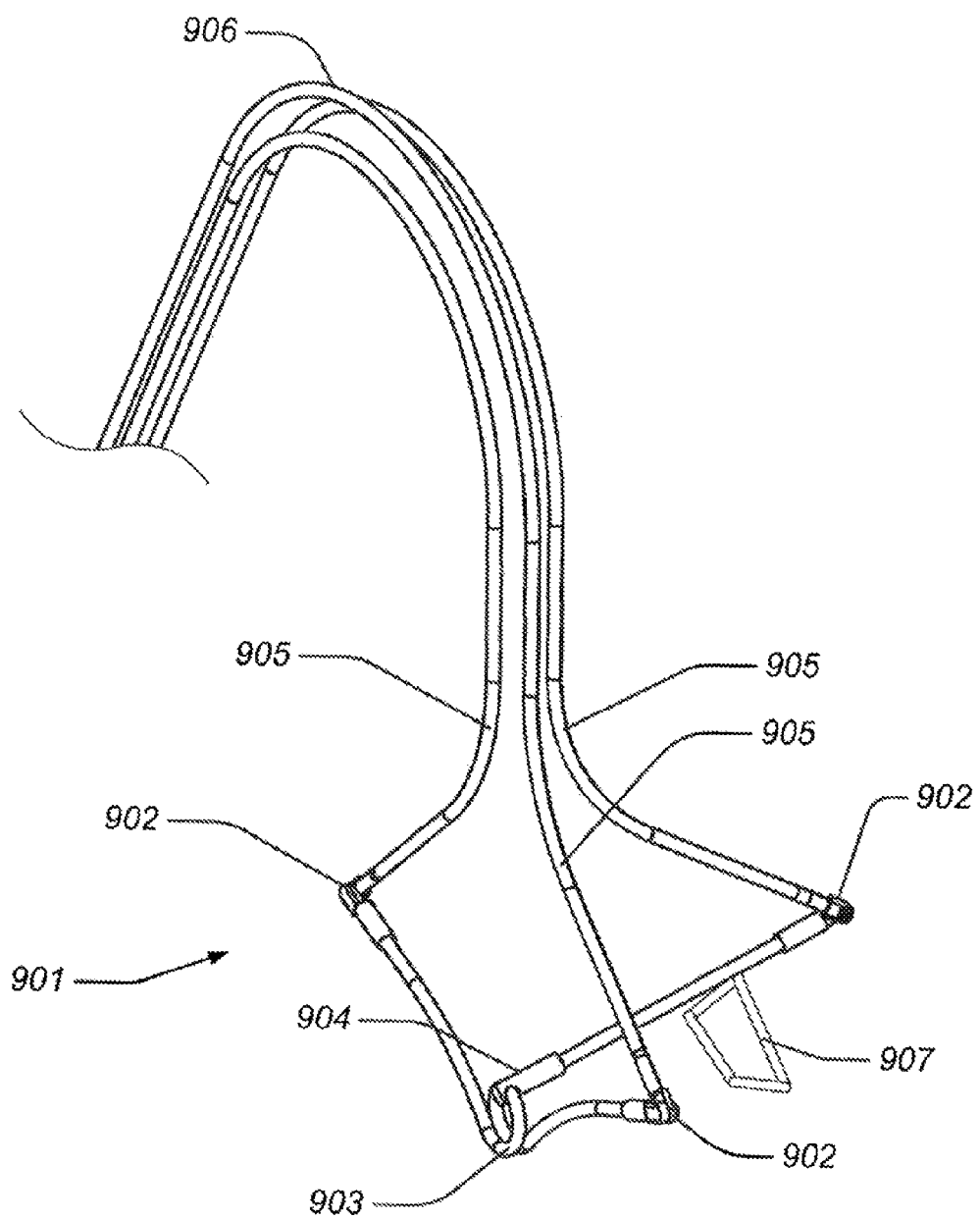
FIG. 9 is an isometric view of an anchor guide frame according to one illustrated embodiment.

FIG. 9 shows an example of an anchor guide frame of a tool according to one illustrated embodiment.

An anchor guide frame 901 is used to guide tissue anchors of the implant device to correct insertion or anchor points or locations. The anchor guide frame 901 shown comprises three guide members, for instance rails 905, but said guide frame may comprise more or fewer guide members. The anchor guide frame 901 embodiment illustrated shows all guide rails 905 connected at the bottom of the guide frame 901. An anchor guide frame is not required to have all guide members connected together, although it is often preferable to do so to create a guide frame that enables tissue anchors to be positioned relative to each other and to anatomical features. Thus, an anchor guide frame may have multiple disconnected groups of connected guide wires.

The anchor guide frame 901 preferably is capable of folding to enable delivery via a catheter. Guide members (e.g., guide wires or rails) 905 may be hinged at bends 902 and guide connection point 904 to enable folding. Loop 903 facilitates folding and also acts as a spring to enable unfolding of the anchor guide frame 901.

Guide members 905 may be formed to have respective bends 906 when no external forces are being applied. When guide members 905 are carried in a catheter with an articulation mechanism shaped into a curve as shown in FIG. 2, the forces exerted on the guide member by the catheter and articulation mechanism will cause bend 906 to align with the curve in the articulation mechanism. Such alignment causes anchor guide frame 901 to rotate to a desired position relative to the catheter orientation. Bend 906 may also be formed to assist in curving the articulation mechanism in a particular way.

An anchor guide frame may also contain additional features which use anatomical features or movement to assist in orientation of said anchor guide mechanism or guide frame 901. An example of such a feature is an alignment fin 907. Alignment fin 907 is attached rigidly to flexible anchor guide frame 901 and shaped so that the alignment fin 907 may be deflected by an anatomical feature, such as mitral valve leaflets, to a particular orientation. As the flexible anchor guide frame 901 is advanced toward an anatomical feature, such as the mitral valve annulus, the shape or motion of an anatomical feature, such as the mitral valve leaflets, may cause alignment fin 907, and thus flexible anchor guide frame 901, to rotate to a desired orientation.

Figure 10:
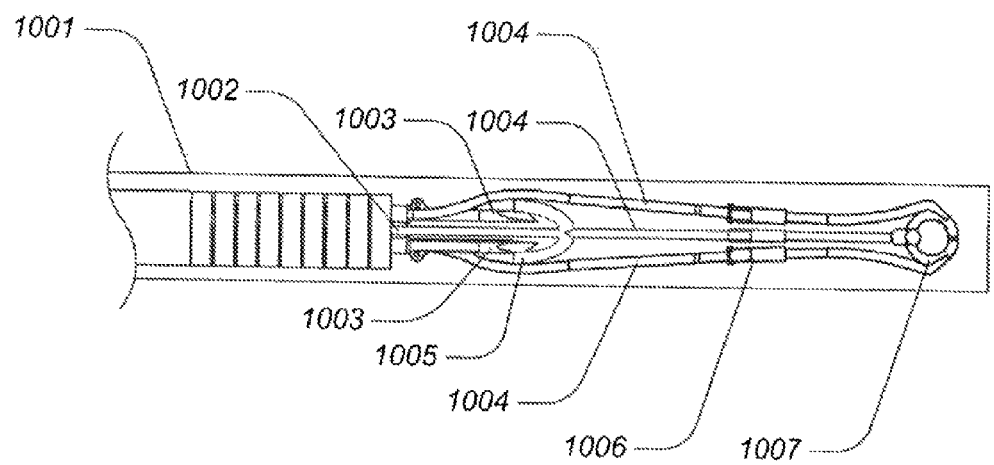
FIG. 10 is a side elevational view of an anchor guide frame compressed into a sheath according to one illustrated embodiment.

FIG. 10 shows an anchor guide frame folded for delivery inside a catheter according to one illustrated embodiment.

An anchor guide frame including guide members (e.g., guide wires or rails) 1004 may be folded inside a catheter sheath 1001. Hinges 1006 and loop 1007 enhance folding of the anchor guide mechanism. In the embodiment illustrated, tissue anchors 1003 fit between the guide members 1004 in the folded configuration. Protective anchor cap 1005 holds and covers the sharp tips of tissue anchors 1003 and may ensure that the tips do not catch or embed on the sides of catheter sheath 1001. Protective anchor cap 1005 may be held in place by control wire 1002

Figure 11:
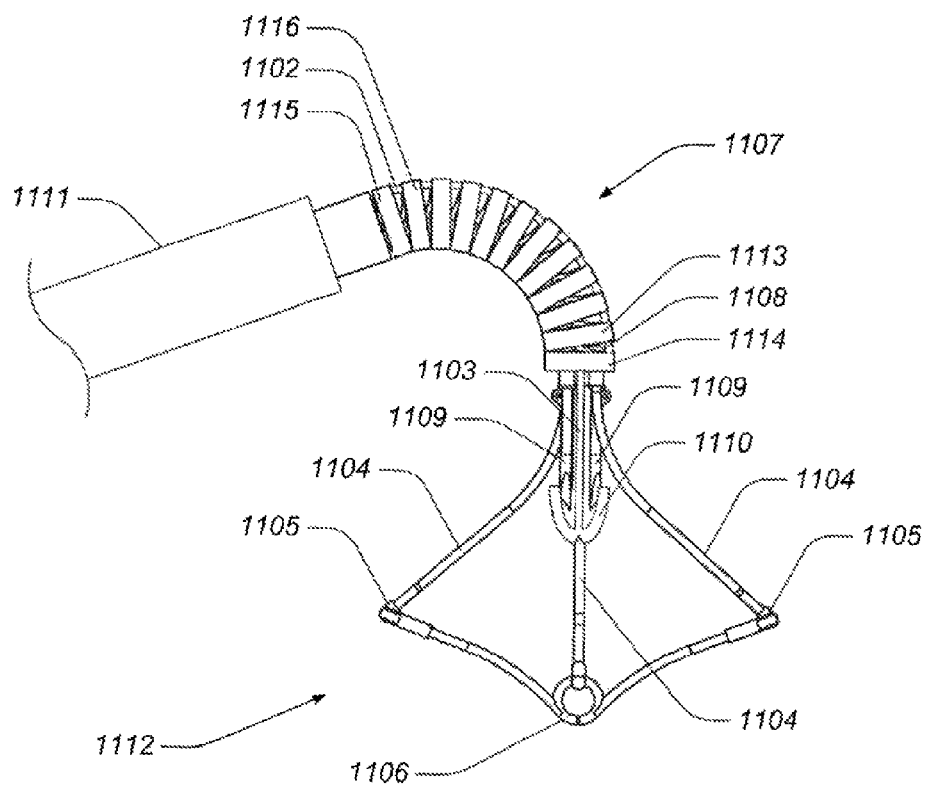
FIG. 11 is an isometric view of an expanded anchor guide frame according to one illustrated embodiment.

FIG. 11 shows an anchor guide frame in an expanded configuration according to one illustrated embodiment.

An anchor guide frame 1112 may self expand after exiting catheter sheath 1111. In particular, the anchor guide frame 1112 may be formed of a resilient material or a shape memory material such as Nitinol. Loop 1106 may be formed to cause the anchor guide frame 1112 to expand. Hinges 1105 facilitate separation of guide members 1104 by about 20 mm to 45 mm. In the illustrated embodiment, tissue anchors 1109 are held within the volume encompassed by anchor guide frame 1112 which ensures the tissue anchors 1109 do not accidentally impinge tissue. Also, the tips of the tissue anchors are held captive within protective anchor cap 1110. The tips of the tissue anchors may be released by advancing control wire 1103 and thereby also advancing anchor cap 1110. The tips of the tissue anchors are no longer held captive if anchor cap 1110 is advanced sufficiently to a point past the tips of the tissue anchors. As guide members 1104 curve away from anchor cap 1110, advancing tissue anchors 1109 causes the tips of the tissue anchors to move away from and avoid anchor cap 1110.

Articulation mechanism 1107 (e.g., articulation joints) of the tool is shown in a curved configuration or state. Articulation mechanism 1107 may be curved using wires (not shown) that are carried on opposing sides relative to a longitudinal axis of the articulation mechanism and fixed to the distal end of the articulation mechanism 1107. Tensioning one wire causes the articulation mechanism 1107 to arc in the direction of the side of the articulation mechanism on which the tensioned wire is carried in. For some situations, it is desirable to cause gaps between articulation links or articulation joints to open at different rates. For example, when inserting articulation mechanism 1107 into the left atrium, it may be preferable to cause the distal links, such as articulation link or joint 1113 and articulation link or joint 1114, to separate or bend prior to or more than the proximal articulation links or joints, such as articulation link or joint 1115 and articulation link or joint 1116. One embodiment to enable such an attribute is to insert springs, as indicated by 1108 and 1102, with varying spring constant k between the links or articulation joints. To cause the distal end of articulation mechanism 1107 to bend first, the distal links should be forced apart by springs with a higher spring constant than the springs between the proximal links. Another embodiment for enabling unequal separation of articulation links or joints is to control the shape of the guide members 1104 that are routed through the articulation mechanism 1107. The guide members should have a preformed bend with a decreasing radius of curvature in the area from proximal articulation link or joint 1115 to distal articulation link or joint 1114.

Figure 12:
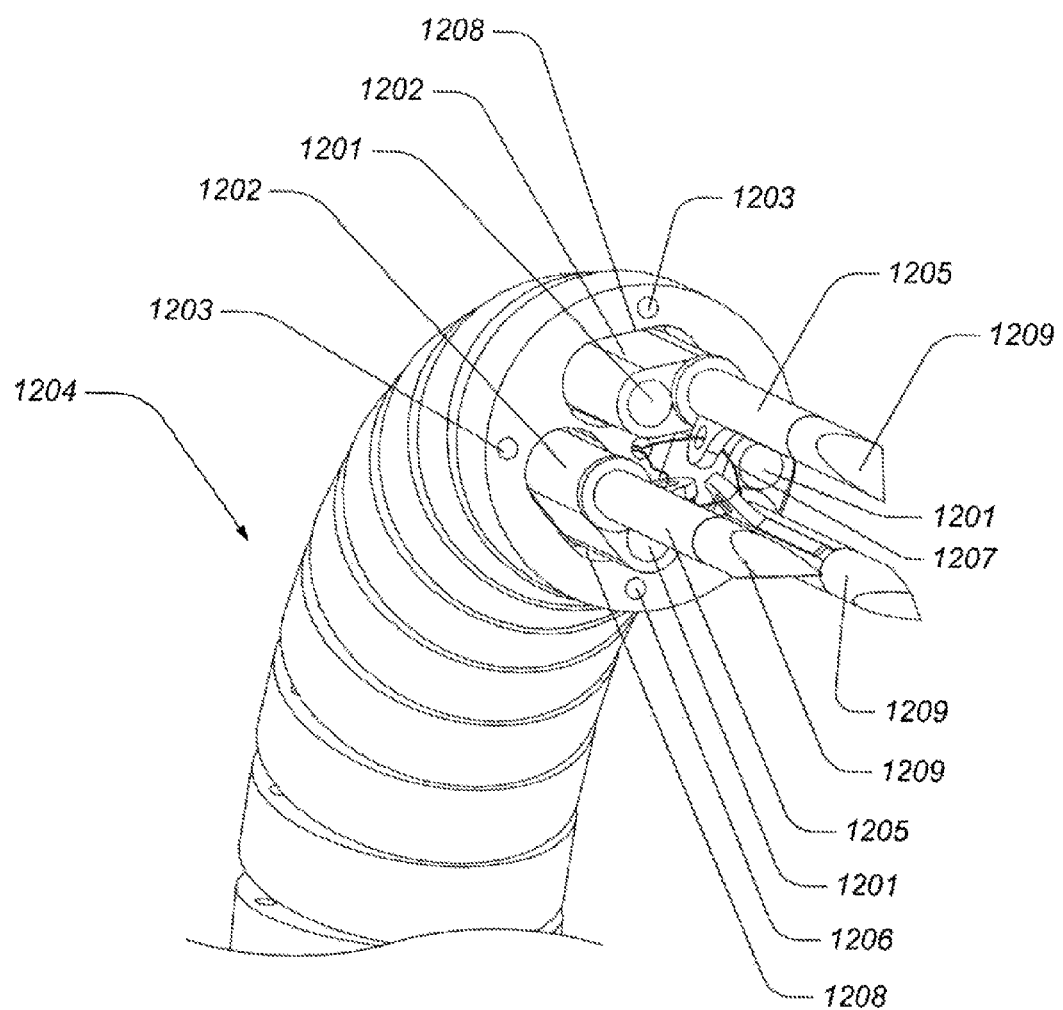
FIG. 12 is an isometric view showing a distal end of a medical device system according to one illustrated embodiment

FIG. 12 shows a configuration of tissue anchors and push tubes at a distal tip of a medical device system according to one illustrated embodiment. For clarity, FIG. 12 omits guide members and anchor guide frame that would typically be located at the distal tip of the medical device system.

An articulation mechanism 1204 may include multiple lumens 1208 through which push tubes 1202 are carried. In this particular embodiment, three lumens 1208 are employed, but other embodiments may comprise more or less. Push tubes 1202 may also include multiple lumens. In this particular embodiment, each push tube 1202 has a lumen 1201 in which a guide member (e.g., guide wire or rail) (not shown) may be carried and a second lumen that carries a release member (e.g., rod or wire) (not shown) which is connected to the tissue anchors 1209. Constriction tubes 1205 may be mated into or onto the distal end of the second lumen. All tissue anchors may be connected by a flexible cable 1207. The flexible cable 1207 may also be carried within a separate lumen within the articulation mechanism 1204. Lumens 1203 are used to carry cables that control the curvature of the articulation mechanism 1204.

Figure 13:
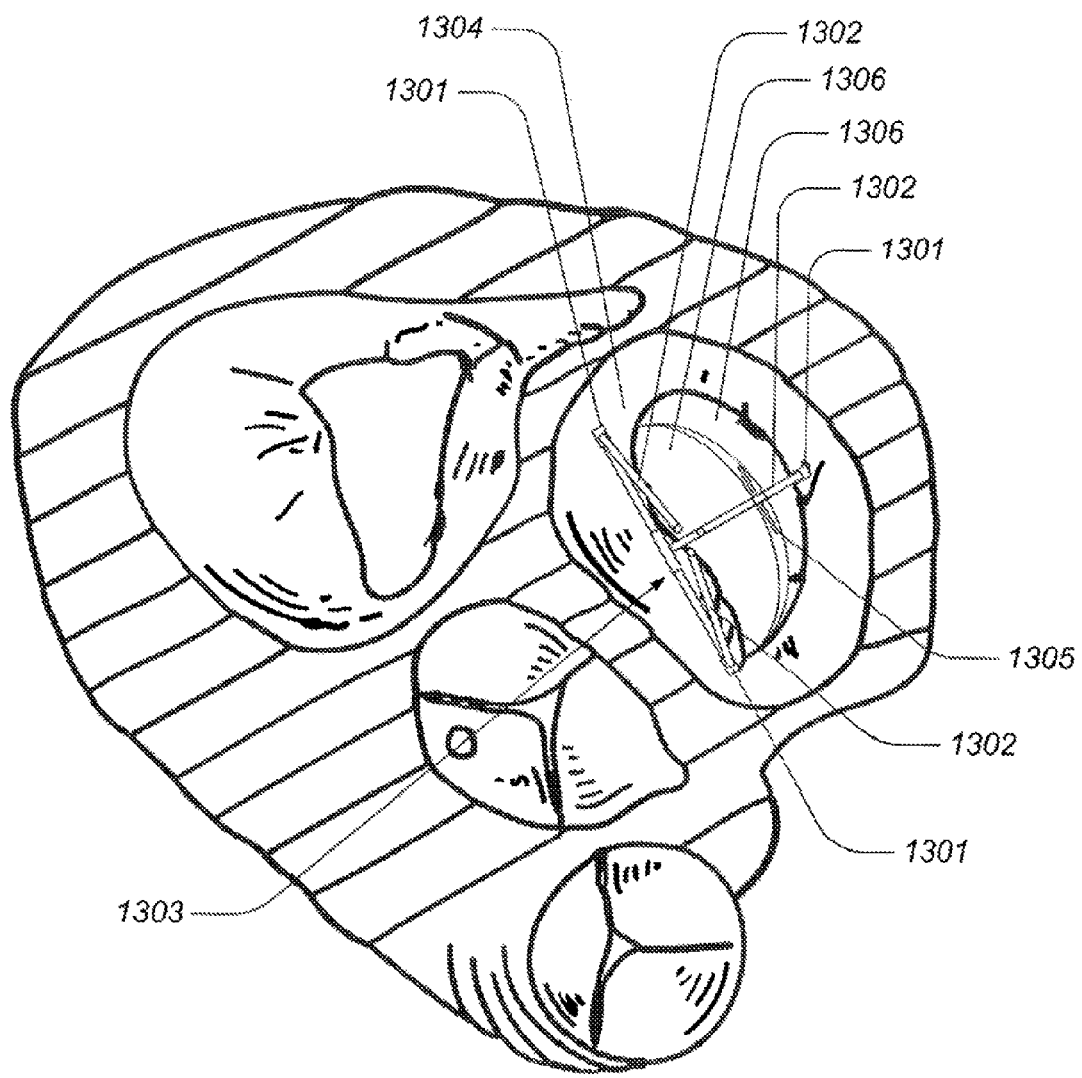
FIG. 13 is a cutaway diagram of a heart showing an example of tissue anchors secured in a mitral valve annulus according to one illustrated embodiment.

FIG. 13 shows a cross section of a heart with an anchor guide frame according to one illustrated embodiment positioned within a left atrium of the heart.

An anchor guide frame 1303 is shown self-located on a mitral annulus 1304 within the left atrium. The tissue anchor deployment sites 1301 are preferably located on the mitral annulus and coincident with bends in the guide members (e.g., guide wires or rails) 1302. While FIG. 13 shows three guide members 1302 and tissue deployment sites 1301 for simplicity; in many cases more deployment sites and guide members are desirable. In such cases, it is a simple matter to add additional guide members and anchor deployment sites to the illustrated embodiment.

Figure 14:
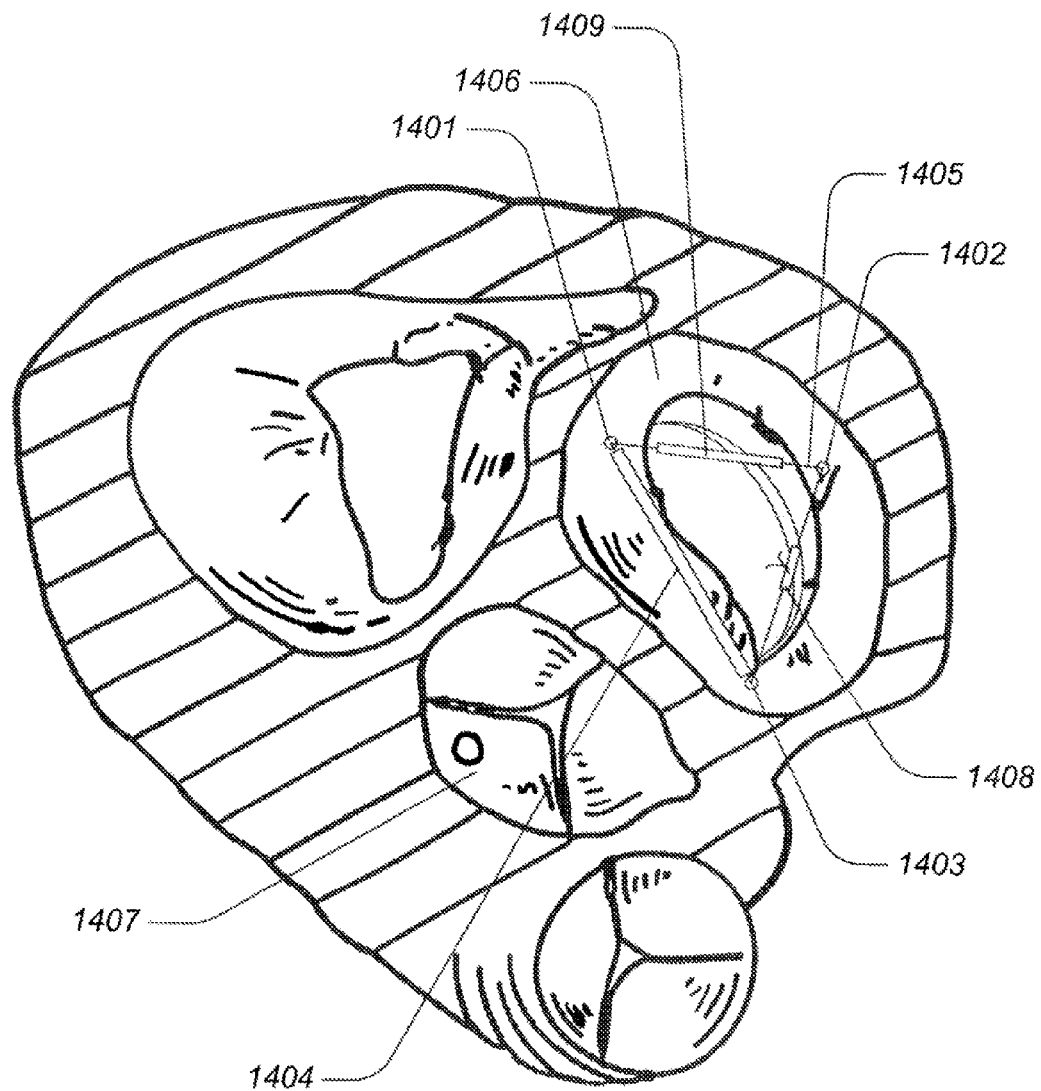
FIG. 14 is a cutaway diagram of a heart showing an example of tissue anchors and a cable used to constrict a mitral valve annulus according to one illustrated embodiment.

An alignment fin 1305 may fit between mitral valve leaflets 1306. The movement and anatomical structure of the mitral valve leaflets 1306 exert force on alignment fin 1305 and assist in orienting the anchor guide frame 1303 correctly FIG. 14 shows a cross section of a heart with an installed assembly capable of constricting a mitral valve annulus according to one illustrated embodiment.

Tissue anchors 1401, 1402, and 1403 are shown fully deployed on the mitral annulus 1406. Tissue anchors 1401-1403 may be connected by a flexible cable 1405. Other mechanisms for connecting tissue anchors 1401, 1402, 1403 are possible. For example, rigid members, preferably with adjustable length (e.g., turn-buckles), may be used to connect the tissue anchors 1401-1403. Flexible cable 1405 may slide through holes on the tissue anchors 1401, 1402, 1403.

Flexible cable 1405 may pass through a hollow spreader bar 1404. Hollow spreader bar 1404 provides support to keep tissue anchors 1401 and 1403 from moving closer together when flexible cable 1405 is shortened. Such support reduces undesired forces being applied to an aortic valve 1407 of the heart.

Reducing a distance between pairs of the tissue anchors 1401, 1402 and 1402, 1403 causes an anterior-posterior (A-P) annular dimension of the mitral valve to reduce and improves leaflet coaptation. Several methods may be used to reduce the distance between two or more pairs of tissue anchors 1401, 1402 and 1402, 1403. A first method is to shorten the cable during the installation procedure by routing the flexible cable 1405 through fastener 1408, pulling the cable manually to be as tight as desired and crimping fastener 1408. Fastener 1408 may also be constructed using a one way clutch so that the flexible cable 1405 can only be pulled through in one direction, in which case crimping is not required. A second method of reducing tissue anchor separation (i.e., distance between two successive tissue anchors) is to include shortening actuator 1409 between two tissue anchors. In the case where shortening actuator 1409 is included, flexible cable 1405 is split and attached to either end of the shortening actuator. One embodiment of shortening actuator 1409 contains an element that is capable of changing length as a response to a stimulus such as changes in an external magnetic field or heating induced by a changing magnetic field. The element capable of changing lengths may be made of a highly magnetostrictive alloy such as Terfenol-D or from a Shape Memory Alloy (SMA) such as specially treated Nitinol. Embodiments of such actuators are described in U.S. Ser. No. 11/902,199. The element capable of changing lengths may be made of a spring under tension (e.g., in an extended configuration) encapsulated in a retainer material that changes state in response to a stimulus (e.g., melts under low heat and solidifies at body temperature—such as a thermoplastic polymer). Current induced in a loop by an external magnetic field may be channeled through the spring. The current may heat the spring which will cause the polymer to soften and the spring length to contract to an unextended configuration. The contraction of the spring can be used to reduce the separation of the tissue anchors. Embodiments of such actuators are described in U.S. Ser. No. 11/905,771.

A closed, electrically conducting loop is required if shortening actuator 1409 is to be responsive to heating or energy induced by a changing magnetic field. Such a loop may be achieved by using an electrically conductive material for flexible cable 1405 and ensuring an electrical contact between both ends of flexible cable 1405 that are connected to shortening actuator 1409.

Figure 15A:
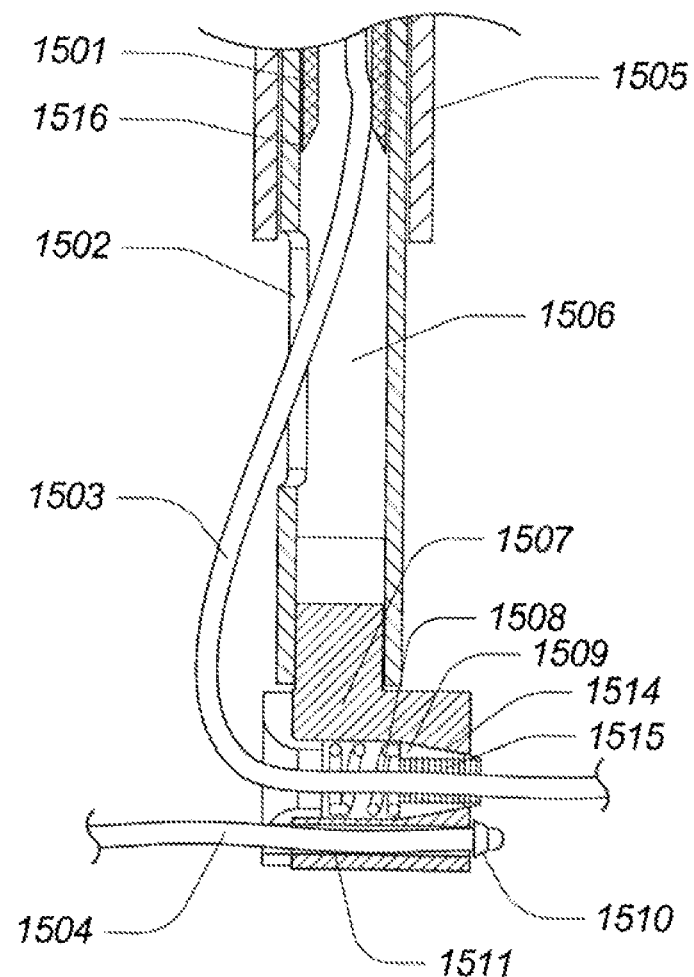
FIGS. 15A and 15B are cross-sectional views of a tool to secure a cable of an implantable device that constricts a bodily orifice at two successive intervals of time illustrating a time prior to cutting the cable and a time when the cable is being cut according to one illustrated embodiment.
Figure 15B:
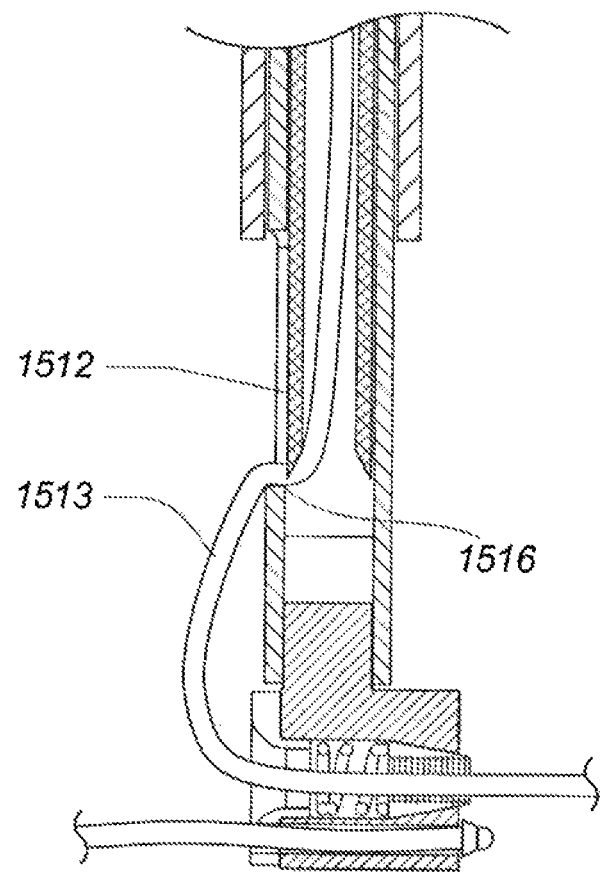

FIGS. 15A and 15B show a tool and fastener used to tighten and secure a cable according to one illustrated embodiment.

Fastener 1507 may be used to tighten or secure cables being used to constrict a bodily orifice. Typically prior to attachment of fastener 1507, tissue anchors have been implanted or placed in the tissue, and a flexible cable has been connected to the tissue anchors. Cable end 1504 and cable end 1503 are typically carried in catheter sheath 1505 and routed outside the body. Cable end 1504 and cable end 1503 may be the two ends of one flexible cable. The portion of the cable not shown loops around the orifice to be constricted and is attached to the implanted tissue anchors used to secure the cable to the orifice.

Cable end 1504 may be fed into hole 1511 and locked by ferrule 1510 while fastener 1507 is still outside the body. Cable end 1503 may be routed through taper lock 1509 while fastener 1507 is still outside the body.

Fastener 1507 may be attached to fastener positioning tube 1506. Cable end 1503 may be inserted through slot 1502 and into fastener positioning tube 1506. Fastener 1507 and fastener positioning tube 1506 may be inserted into catheter sheath 1505 and advanced until fastener 1507 is proximate an annulus of the orifice to be constricted. Cable end 1503 may be pulled in a direction away from fastener 1507, causing the cable to pull through taper lock 1509 and constrict the orifice. While the cable is being tightened and secured, fastener 1507 may be held by fastener positioning tube 1506. Taper lock 1509 restricts cable end 1503 from being pulled out the right side (as illustrated in FIGS. 15A, 15B) of fastener 1507. Taper lock 1509 may have teeth 1515 to grip cable end 1503. Taper lock 1509 may have a longitudinal slot to enable compression of taper lock 1509 and constriction around cable end 1503. Spring 1508 may force taper lock 1509 into a conical hole 1514, causing the force taper lock 1509 to tighten around cable end 1503.

When the orifice has been sufficiently constricted, cable end 1503 may be severed using cable cutting tube 1501. Cable cutting tube 1501 includes a sharpened end 1516. In particular, FIG. 15A shows cable cutting tube 1501 in a retracted position. The cable cutting tube may slide inside of fastener positioning tube 1506. FIG. 15B shows cable cutting tube 1512 in the cable cutting position, physically engaging the cable 1513. Cable cutting tube 1512 may sever cable end 1513 by forcing cable end 1513 against the end of slot 1516. The cable end may be severed in other ways, including using a hot tip to melt through the cable.

Figure 16A:
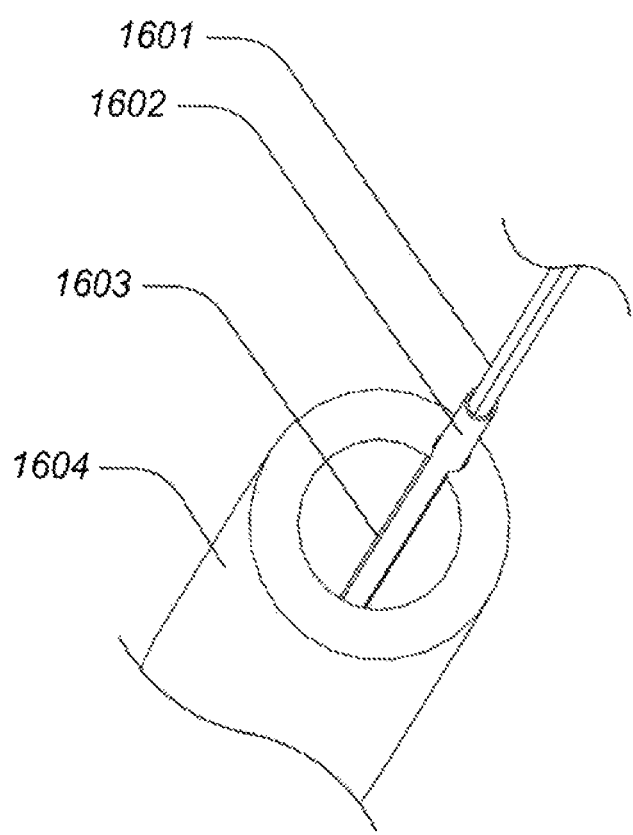
FIGS. 16A and 16B are sequential isometric views showing a portion of a catheter with side slots according to one illustrated embodiment
Figure 16B:
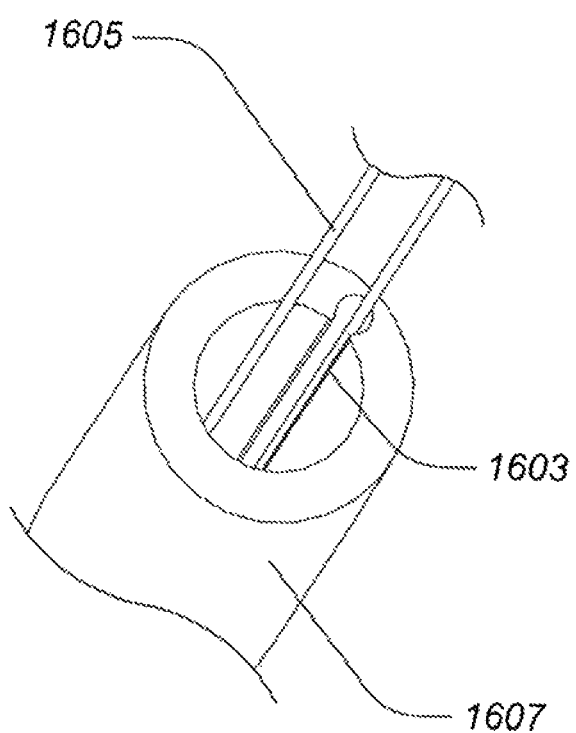

FIGS. 16A and 16B show a catheter with grooves, or side slots, and a mechanism for securing cables or wires in said side slots according to one illustrated embodiment.

In particular, FIG. 16A shows catheter 1604 with cables 1601 held within longitudinal groove 1603 on the inner surface of the tube wall by tube 1602. The longitudinal groove 1603 has a cross sectional shape that enables tube 1602 to be held captive. FIG. 16A shows a circular groove (i.e., arcuate cross-section), but other shapes may be used. Tube 1602 carries cables 1601. Tube 1602 could also carry wires or tubes. When tube 1602 is removed by pulling it out the end, as shown in FIG. 16B by catheter 1607, cables 1605 are free to move into the central area of the tube. Tube 1602 can be reinserted over cables 1605 to again constrain them in groove 1603.

Although FIGS. 16A and 16B show catheter 1604 and catheter 1607 with only one groove 1603, it is possible to have many such grooves in a catheter and to secure a plurality of wires and tubes in said grooves. One of the reasons for securing cables or wires in grooves, or side slots, is to eliminate tangling of cables or wires during medical procedures.

Figure 17:
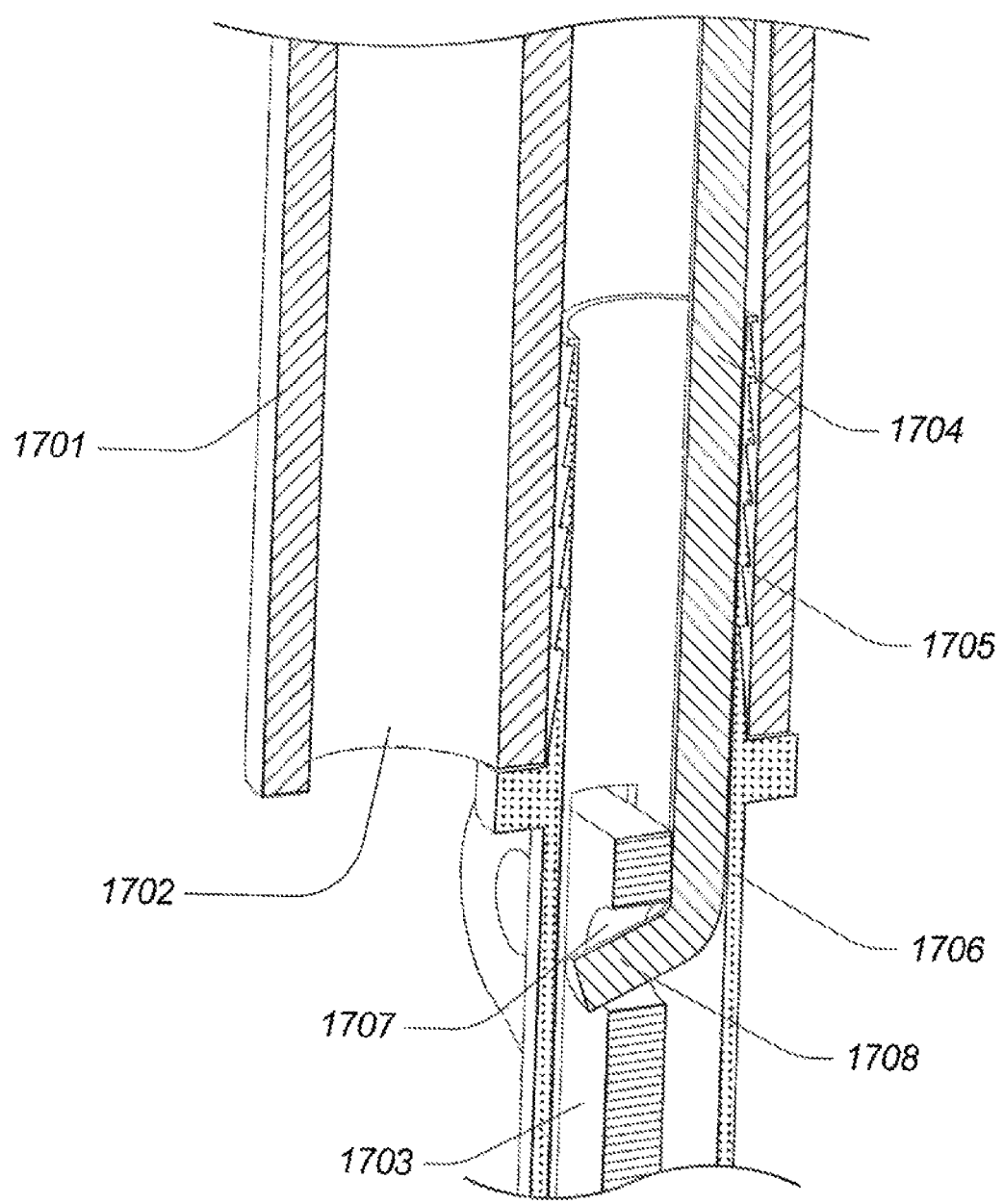
FIG. 17 is a cross-sectional partial view of a mechanism according to one illustrated embodiment for holding a tissue anchor captive.

FIG. 17 shows a mechanism for holding a tissue anchor captive according to one illustrated embodiment Tissue anchor 1703 may be held captive in constriction tube 1706 of the tool by release member 1704. Constriction tube 1706 may be inserted and secured to a distal end of one lumen of push tube 1701. Constriction tube 1706 may be held captive in the lumen by one or more ribs 1705.

Tissue anchor 1703 may be released from constriction tube 1706 by retracting push tube 1701 and constriction tube 1706 relative to release member 1704. As the distal end of constriction tube 1706 clears hole 1707, tip of release member 1708 will pop out of hole 1707 and tissue anchor 1703 will no longer be held captive.

Lumen 1702 of push tube 1701 may be used to slide over a guide member.

Figure 18A:
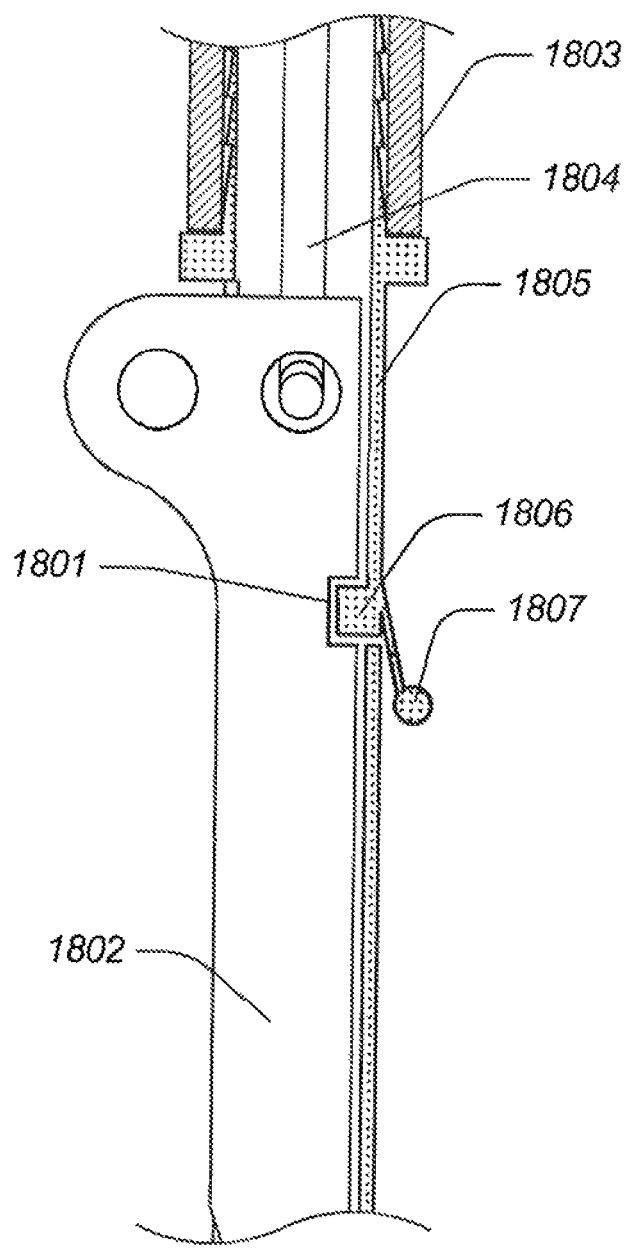
FIGS. 18A and 18B are successive side elevational views of a mechanism according to one illustrated embodiment for restricting a tissue anchor from release until the tissue anchor is fully embedded in tissue.
Figure 18B:
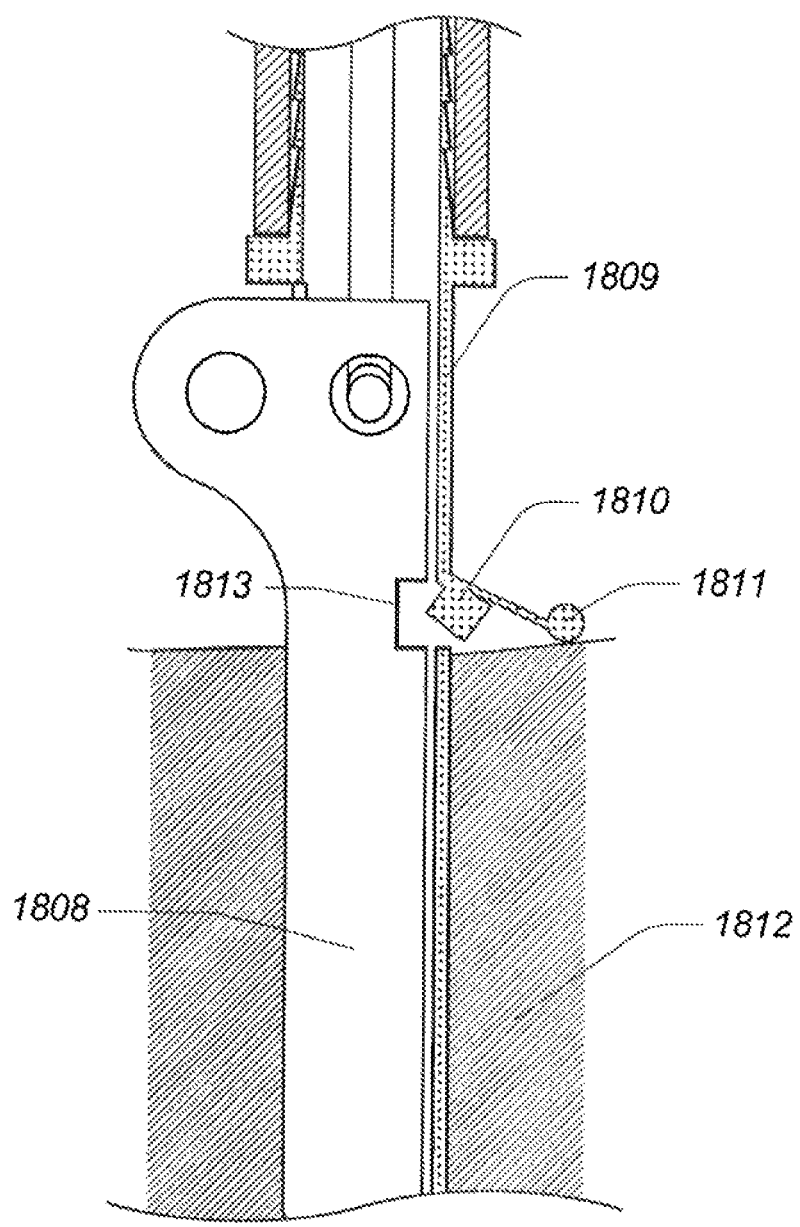

FIGS. 18A and 18B show mechanisms for restricting a tissue anchor from release until anchor is fully embedded in tissue according to one illustrated embodiment An additional benefit is provided if the tool to implant the implantable device for constricting a bodily orifice does not release tissue anchors of the implantable device until the tissue anchors are fully embedded in the tissue. It is possible to achieve this benefit by adding an additional latch 1806, 1810 to the tool.

In particular, FIG. 18A shows a tissue anchor 1802 prior to deployment. The tissue anchor 1802 may not be released from constriction tube 1805 by retracting push tube 1803 and constriction tube 1805 relative to release member 1804 because latch 1806 in an engaged or locked position extends into a notch 1801. Latch 1806 is coupled to lever 1807 in this illustrated embodiment.

FIG. 18B shows the tissue anchor 1808 fully deployed into tissue 1812. As tissue anchor 1808 was deployed into tissue 1812, the surface of tissue 1812 causes lever 1811 to bend. When lever 1811 is bent, latch 1810 clears notch 1813. Once latch 1810 clears notch 1813, tissue anchor 1808 may be released from constriction tube 1809.

Figure 19A:
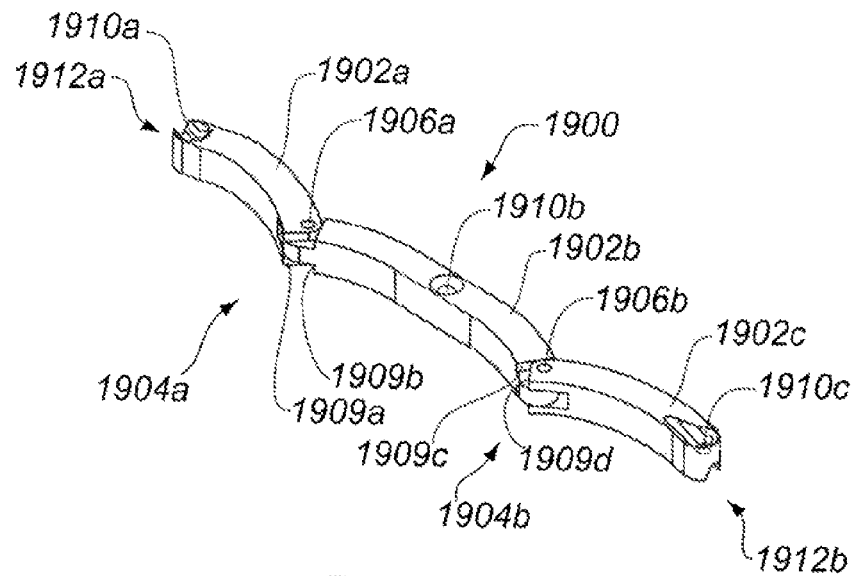
FIG. 19A is an isometric view of an implant member according to one illustrated embodiment, the implant member shown in a delivery configuration.
Figure 19B:
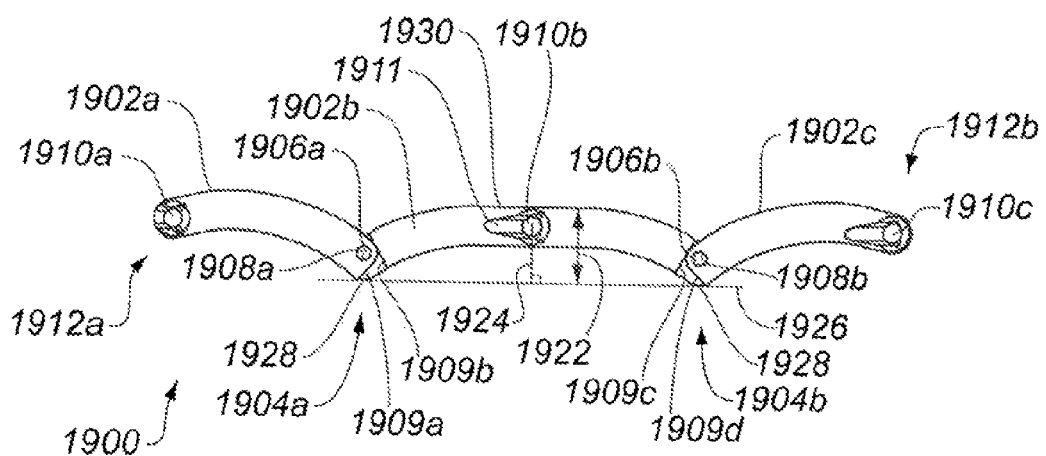
FIG. 19B is a top plan view of the implant member of FIG. 19A shown in the delivery configuration.
Figure 19C:
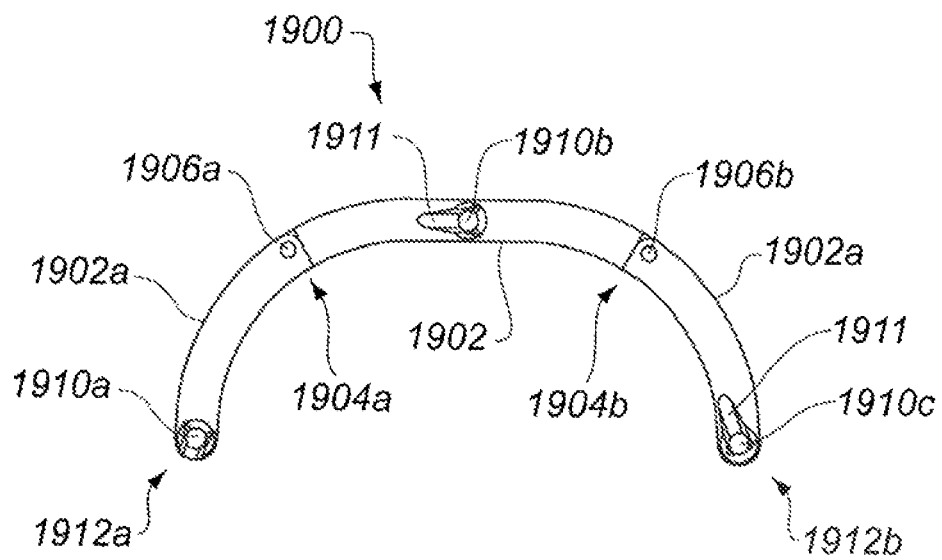
FIG. 19C is an isometric view of the implant member of FIGS. 19A and 19B, the implant member shown in an implantable configuration.
Figure 19D:
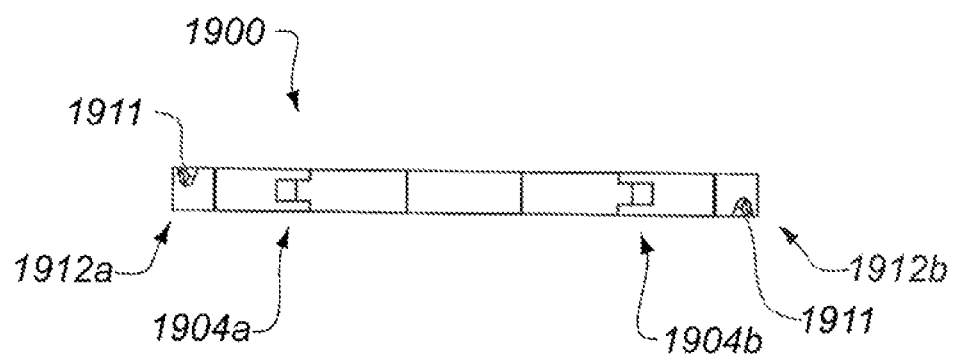
FIG. 19D is a front elevational view of the implant member of FIGS. 19A-19C, shown in the implantable configuration.

FIGS. 19A-19D show an implant member 1900, according to one illustrated embodiment. In particular, FIGS. 19A and 19B show the implant member in a first configuration that is representative of one of a delivery configuration, an unanchored configuration or an untensioned configuration, while FIGS. 19C and 19D show the implant member in second configuration that is representative of one of an implantable configuration, a deployed configuration, an anchored configuration or a tensioned configuration. This implant member 1900 may be particularly suitable for use with the tissue anchors, anchoring guiding frame and techniques of FIGS. 5C, 5D, and FIGS. 8C-8F.

The implant member 1900 may be used to reshape, reconfigure and/or reinforce an orifice in bodily tissue. For example, the implant member 1900 may be used to reshape, reconfigure and/or reinforce a valve, for instance a natural valve or an artificial valve. The valve may, for example take the form of a mitral, tricuspid, pulmonary and/or aortic valve of the heart. Alternatively, the valve may take the form of another valve in another organ of the body.

The implant member 1900 has a plurality of arcuate segments 1902a-1902c (collectively 1902). While three segments 1902 are illustrated, the implant member 1900 may include additional segments. The total number of segments 1902 may be based on the size of the valve that the implant member 1900 will be used with. The total number of segments 1902 may additionally or alternatively be based on a largest lateral dimension that may be accommodated by a given or desired catheter (i.e., diameter of catheter lumen). For instance, employing a greater number of segments 1902 means that each segment may have a smaller height 1922, while still achieving a desired lateral dimension or height of the overall implant member 1900 when in the implanted configuration.

The segments 1902 are physically coupled to one another, and in at least some configurations are articulated for movement with respect to one another, for example pivotal movement. The implant member 1900 includes a number of hinges 1904a, 1904b (collectively 1904 pivotally coupling neighboring ones of the segments 1902. Each hinge 1904 may include a hinge pin 1906a, 1906b (collectively 1906) received via throughholes 1908a, 1908b (collectively 1908) in the segments 1902. The hinge pin 1906 should be fixedly received in the throughhole 1908 to ensure that the hinge pin 1906 does not become dislodged after implantation. The hinge pin 1906 may be swaged in the throughhole 1908, and may additionally or alternatively be fixed using other mechanisms. The locations of the hinge pins 1906 of the hinges 1904 may be offset from a longitudinal centerline (i.e., the arc that passes longitudinally through the geometric center between the longitudinal arcuate edges) of the respective one of the arcuate segments 1902. Such may avoid having to remove material on an outside edge to allow the segments 1902 to pivot. Alternatively, the hinge pins 1906 may lie along the longitudinal centerline.

The segments 1902 include stops 1909a-1909d (collectively 1909) proximate the hinges 1904. The stops 1909 on neighboring ones of the segments 1902 cooperatively interact by engaging one another to prevent the segments 1902 from being pivoted past a defined angle with respect to one another. The stops thus serve to lock the segments 1902 from further articulation in one direction, from the delivery configuration to the implanted configuration. While illustrated as simple complimentary engagement surfaces, the stops may take other forms. For example, stops may take the form a detent or other lock structure. Stops 1909 may lock the segments 1902 from movement in two, opposed directions. Stops 1909 may also provide torsional stiffness to the hinges 1904.

In some example embodiments, a portion of an implant member having a variable bending stiffness in at least one dimensional plane is employed. In this illustrated embodiment, implant member 1900 is configured to be bendable between a first configuration in which implant member 1900 has an elongated shape and a second configuration in which implant member 1900 has an arcuate shape. Stops 1909 allow portions of the implant member 1900 coupled by hinges 1904 to have a variable bending stiffness in at least one dimensional plane. Hinges 1904 allow implant member 1900 to bend via the articulation of segments 1902 in a plane when implant member 1900 is in its first configuration. Stops 1909 restrain further articulation between segments 1902 when implant member 1900 is in the second configuration and any further bending is dependent on any additional flexing of segments 1902. In this regard, the implant member 1900 has a reduced bending stiffness in the at least one dimensional plane when the implant member 1900 is in the first configuration and an increased bending stiffness in the one dimensional plane when the implant member 1900 is in the second configuration. Variable bending stiffness characteristics can be achieved in other ways by other example embodiments. The implant member 1900 includes a number of guide line receivers 1910a-1910c (collectively 1910). The guide line receivers 1910 may be formed as holes or apertures and are sized to receive a guide line such as a guide wire (not shown in FIGS. 19A-19D) to allow the implant member 1900 to ride on or otherwise be guided or advanced along the guide line. The guide line may, for example, take the form of the guide wire of FIGS. 5C, 5D and FIGS. 8C-8F. In various embodiments, the guide line receivers 1910 allow implant member 1900 to ride on, or otherwise be guided or advanced along a guide line that is received or coupled to a tissue anchor that is embedded into tissue. The guide line receivers 1910a, 1910c are located proximate a first end 1912a, a second end 1912b, respectively. The guide line receiver 1910b is between the first and second ends 1912a, 1912b. In particular, each of the segments 1902 may have one of the guide line receivers 1910. While illustrated as being approximately midway between the first and second ends 1912a, 1912b, the guide line receiver 1910b between the first and second ends 1912a, 1912b may be offset to one side or the other of a center line (perpendicular bisector 1924) of the implant member 1900, along a longitudinal axis thereof. The implant member 1900 may include additional guide line receivers (not shown). For instance, all or some of one or more additional segments (not shown) may have guide line receivers. Additionally, or alternatively, one segment 1902 may have more than one guide line receiver 1910. One or more of the segments 1902 may include relief 1911 (only one called out in FIG. 19B) proximate the guide line receiver 1910. The relief 1911 may accommodate a guide line such as a wire or suture.

As illustrated in FIGS. 19A and 19B, the segments 1902 of the implant member 1900 may be moved with respect to one another, into a first configuration, which in this illustrated embodiment is representative of a delivery configuration or unanchored configuration. In the delivery or unanchored configuration, the implant member 1900 is sized and dimensioned to be deliverable via a catheter. In the delivery configuration, the implant member 1900 may have an elongated, scallop or serpentine profile, as best illustrated in FIG. 19B. A maximum longitudinal dimension in the delivery or unanchored configuration is relatively long as compared to the maximum longitudinal dimension in the implanted or anchored configuration. Thus, a maximum lateral dimension of the implant member 1900 (i.e., maximum dimension measured perpendicularly to a longitudinal axis extending between the first and second ends 1912a, 1912b), is minimized. The maximum lateral dimension in the delivery or unanchored configurations is relatively short or small as compared to the maximum lateral dimension in a second configuration, which in this illustrated embodiment is representative of an implantable or deployed or anchored configuration. As illustrated in FIG. 19B, the maximum lateral dimension may, for example, be approximately equal to a height 1922 of the arch formed by the one of the arcuate segments 1902 (i.e., 1902b in this illustrated embodiment), as measured by a perpendicular bisector 1924 that extends from a chord line 1926 passing tangent to portions of an inner surface 1928 (called out twice in FIG. 19B) of one or more of the arcuate segments 1902, to where the perpendicular bisector 1924 intersects an outer surface 1930 of the arcuate segment 1902 when the plurality of arcuate segments are positioned in the delivery or unanchored configuration. Thus, the implant member 1900 may be accommodated by a catheter. Catheters are typically long, but which have relatively narrow diameters. Thus, catheters have relatively unlimited longitudinal capacity as compared to lateral or radial capacity.

As illustrated in FIGS. 19C and 19D, the segments 1902 of the implant member 1900 may be moved with respect to one another into the second configuration representative of an implantable or deployed or anchored configuration. In the second configuration, the implant member 1902 has an arcuate or annular shape or profile. The arcuate or annular shape is sized and dimensioned to encompass at least part of an orifice. For example, the arcuate or annular shape may be sized and dimensioned to overlie part of an annulus of a mitral valve of a heart. In the second configuration, the dimensions of the implant member 1902 are too large to be accommodated by a typical catheter. In particular, a lateral dimension or height of the implant member is too large to be received by a lumen of the catheter.

As described in detail below, forces or tension may be applied to the implant member 1900 at the guide line receivers 1910, for instance via embedded tissue anchors and/or wires and/or sutures. Such may tension the implant member 1900 into the second configuration (FIGS. 19C and 19D), while the stops 1909 prevent the segments 1902 of implant member 1900 from articulating past the implanted configuration. Such results in the implant member 1900 having a rigid structure in the second configuration.

Figure 20A:
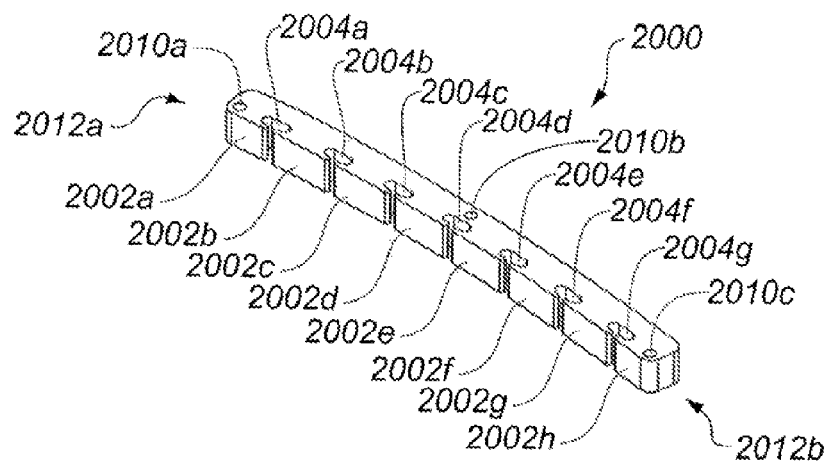
FIG. 20A is an isometric view of an implant member according to another illustrated embodiment, the implant member shown in a delivery configuration.
Figure 20B:
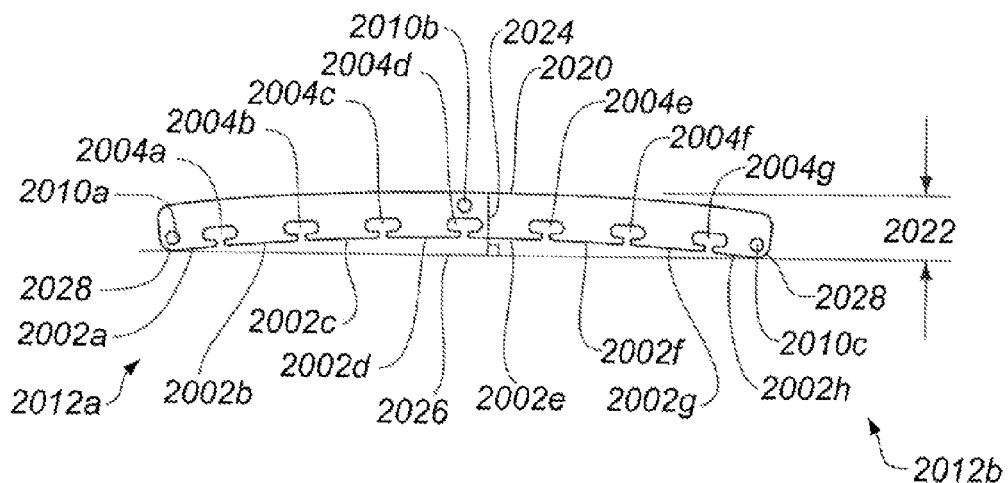
FIG. 20B is a top plan view of the implant member of FIG. 20A shown in the delivery configuration.
Figure 20C:
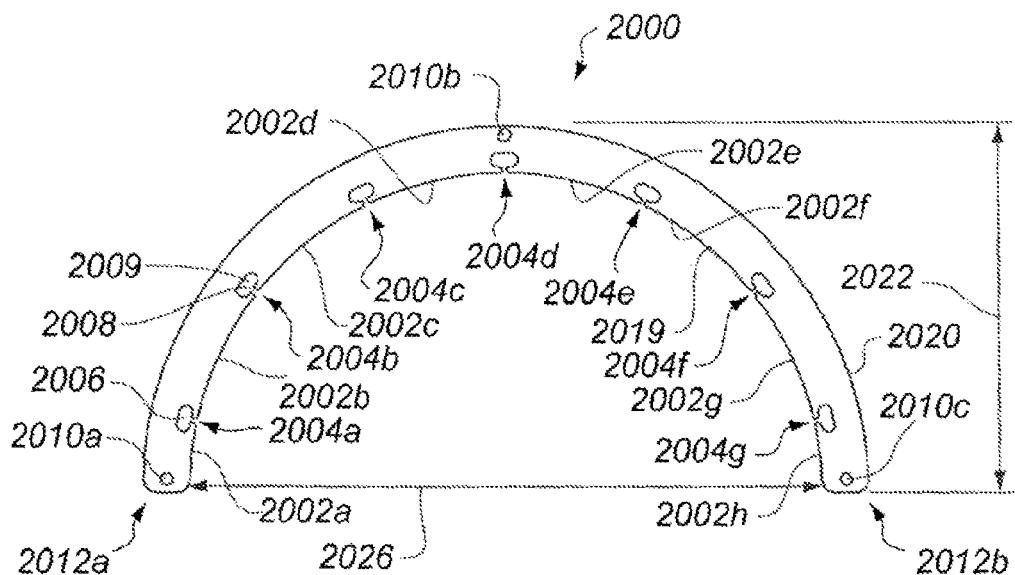
FIG. 20C is an isometric view of the implant member of FIGS. 20A and 20B, the implant member shown in an implantable configuration.
Figure 20D:
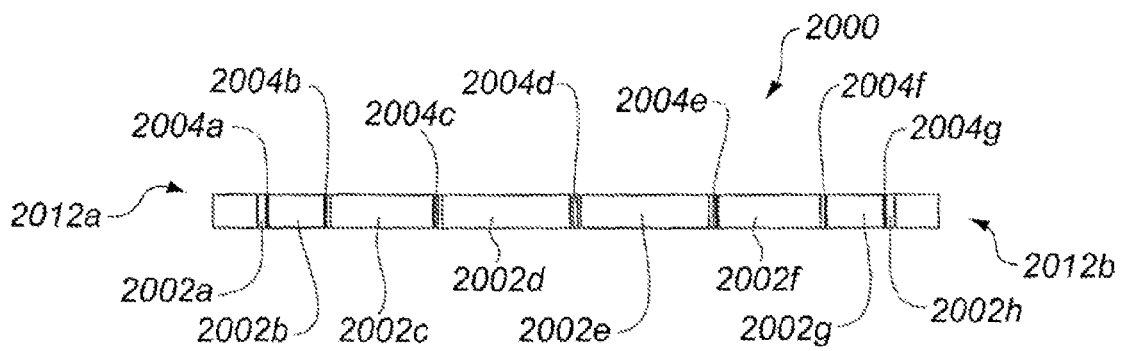
FIG. 20D is a front elevational view of the implant member of FIGS. 20A-209C, shown in the implantable configuration.

FIG. 20A-20D show an implant member 2000, according to one illustrated embodiment. In particular, FIGS. 20A and 20B show the implant member 2000 in a first configuration representative of a delivery configuration or an unanchored configuration, while FIGS. 20C and 20D show the implant member 2000 in a second configuration representative of a deployed configuration or an implantable configuration or an anchored configuration. This implant member 2000 may be particularly suitable for use with the tissue anchors, anchoring guiding frame and techniques of FIGS. 5C, 5D, and FIGS. 8C-8F, by way of non-limiting example.

The implant member 2000 may be used to reshape, reconfigure and/or reinforce an orifice in bodily tissue. For example, the implant member 2000 may be used to reshape, reconfigure and/or reinforce a valve, for instance a natural valve or an artificial valve. The valve may, for example take the form of a mitral, tricuspid, pulmonary and/or aortic valve of the heart. Alternatively, the valve may take the form of another valve in another organ of the body.

The implant member 2000 has a plurality of arcuate segments 2002a-2002h (collectively 2002). While eight segments 2002 are illustrated, the implant member 2000 may include fewer or greater number of segments. The total number of segments 2002 may be based on the size of the valve that the implant member 2000 will be used with. The total number of segments 2002 may additionally or alternatively be based on a largest lateral dimension that may be accommodated by a given or desired catheter (i.e., diameter of catheter lumen). For instance, employing a greater number of segments 2002 means that the implant member 2000 may have a smaller height in the first configuration, while still achieving a desired lateral dimension or height of the overall implant member 2000 when in the second configuration.

The segments 2002 are physically coupled to one another, and in at least some configurations are articulated for movement with respect to one another, for example pivotal movement. The implant member 2000 includes a number of flexure joints 2004a-2004g (collectively 2004) pivotally coupling neighboring ones of the segments 2002. Each flexure joint 2004 may be defined by a recess 2006 (only one called out in FIG. 20C) defined in the implant member 2000. Thus, in contrast to the implant member 1900 (FIGS. 19A-19D), the implant member 2000 may be a unitary structure formed from a single piece of material. The recesses 2006 are illustrated as being on an inner radius, diameter or surface 2019 of the implant member 2000. Alternatively, recesses may be formed on an outer radius, diameter or outer peripheral surface 2020 of the implant member, diametrically opposed to the recesses 2006 illustrated in FIGS. 20A-20D.

The recesses 2006 may be defined or formed via machining operations, for instance drilling, milling, laser cutting, water jetting, etc. In particular the recesses 2006 may have an entrance 2008 (only one called out in FIG. 20C) at an inner peripheral surface 2019 of the implant member 2000, and may have an enlarged portion 2009 (only one called out in FIG. 20C) spaced inwardly of the entrance 2008. The recesses 2006 may have rounded corners which may alleviate stress and/or possible crack formation. Such may also prevent snagging or tearing of bodily tissue.

The implant member 2000 may employ the resiliency of the material from which the implant member 2000 is formed to limit the bending or travel of the segments 2002. Alternatively, the implant member 2000 may include stops proximate the flexure joints 2004. The stops on neighboring ones of the segment 2002 would cooperatively interact by engaging one another to prevent the segments 2002 from being pivoted past a defined angle with respect to one another. Accordingly, in various example embodiments, a portion of implant member 2000 has a variable stiffness in at least one dimensional plane. In a manner similar to other described embodiments, the use of stops can allow implant member 2000 to have a reduced bending stiffness when implant member 2000 is in its first configuration and an increased bending stiffness when implant member 2000 is in its second configuration. In this example embodiment, a portion of implant member 2000 has a substantially equal bending stiffness in each of a plurality of directions in at least one dimensional plane when implant member 2000 is in its first configuration while the portion of implant member 2000 has a substantially unequal bending stiffness in each of the plurality of directions in the at least one dimensional plane when implant member 2000 is in its second configuration. In this example embodiment, the stops provide the unequal bending stiffness in each of the plurality of directions in the at least one dimensional plane when implant member 2000 is in its second configuration.

The implant member 2000 includes a number of guide line receivers 2010a-2000c (collectively 2010). The guide line receivers 2010 are formed as holes or apertures and are sized to receive a guide line or wire (not shown in FIGS. 20A-20D) to allow the implant member 2000 to ride on or otherwise be guided or advanced along the guide line. The guide line receivers 2010 are located proximate a first end 2012a, a second end 2012b and between 2012c the first and second ends 2012a, 2012b. In particular, only some of the segments 2002 may have one of the guide line receivers 2010. While illustrated as being approximately midway between the first and second ends 2012a, 2012b, the guide line receiver 2010b between the first and second ends 2012a, 2012b may be offset to one side or the other of a center line (perpendicular bisector 2024) of the implant member 2000, along a longitudinal axis thereof. The implant member 2000 may include additional guide line receivers (not shown). For instance, all or some of one or more additional segments (not shown) may have guide line receivers. Additionally, or alternatively, one segment 2002 may have more than one guide receiver 2010. Similar to previously described embodiments, each of one or more of the segments 2002 may include a relief (not shown) proximate the guide receiver 2010. Each of these reliefs may accommodate a guide line such as a guide wire or suture.

As illustrated in FIGS. 20A and 20B, the segments 2002 of the implant member 2000 may be moved with respect to one another, into a first configuration representative of a delivery or unanchored configuration. In the first configuration, the implant member 2000 is sized and dimensioned to be deliverable via a catheter. In the first configuration, the implant member 2000 may have an elongated crenulated profile, as best illustrated in FIG. 20B. A maximum longitudinal dimension in the first configuration is relatively long as compared to the maximum longitudinal dimension in a second configuration that is representative of an implantable, deployed or anchored configuration. Thus, a maximum lateral dimension of the implant member 2000 (i.e., maximum dimension measured perpendicularly to a longitudinal axis extending between the first and second ends 2012a, 2012b), is reduced. The maximum lateral dimension in the first configuration is relatively short or small as compared to the maximum lateral dimension in the second configuration. As illustrated in FIG. 20B, the maximum lateral dimension may, for example, be approximately equal to a height 2022 of the arch formed by the implant member 2000, as measured by a perpendicular bisector 2024 that extends from a chord line 2026 passing tangent to portions 2028 of an inner surface located at the first and second ends 2012a, 2012b, to where the perpendicular bisector 2024 intersects an outer surface 2020 of the implant member 2000. Thus, the implant member 2000 may be accommodated by a catheter, which catheters are typically long but which have relatively narrow diameters.

As illustrated in FIGS. 20C and 20D, the segments 2002 of the implant member 2000 may be moved with respect to one another into a second configuration representative of an implantable, deployed or anchored configuration. In the second configuration, the implant member 2000 has an arcuate, annular or C-shape or profile. The arcuate, annular or C-shape is sized and dimension to encompass at least part of an orifice. In the second configuration, the dimensions of the implant member 2000 are too large to be accommodated by a typical catheter sheath. In particular, a lateral dimension or height of the implant member is too large to be received by a lumen of the catheter.

As described in detail below, forces or tension may be applied to the implant member 2000 at the guide line receivers 2010, for instance via tissue anchors and/or guide lines, guide wires and/or sutures. Such may tension the implant member 2000 into the second configuration (FIGS. 20C and 20D).

Figure 20E:
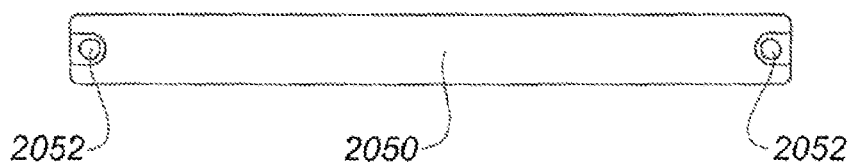
FIG. 20E is a top plan view showing an implant cross member, according to one illustrated embodiment.

FIG. 20E shows an implant cross member 2050, according to one illustrated embodiment. The implant cross member 2050 may have two or more guide line receivers 2052, to receive guide lines such as guide wires (not shown in FIG. 20E). The guide line receivers 2052 may be proximate opposite ends of the implant cross member 2050. Thus, the implant cross member 2050 may ride or otherwise advance along the guide lines or guide wires toward tissue anchors embedded in tissue. The implant cross member 2050 can be anchored across the ends of arms of an implant member such as implant member 1900 (FIGS. 19A-19D), or implant member 2000 (FIGS. 20A-20D) to form a generally D-shape profile with the implant member. The implant cross member 2050 may take the form of an elongated generally rigid structure or an elongated cable or wire, which is generally rigid once anchored. Such may result in a more rigid structure than the structures having generally C-shaped profiles. The implant cross member 2050 may optionally include couplers (not shown) to couple to complimentary couplers on the implant member 1900, 2000.

In contrast to other valve reformation structures, at least some of the implant members described herein such as implant members 1900 (FIGS. 19A-19D), 2000 (FIGS. 20A-20D), do not need to have a cable passing through all of the segments as the sole means of coupling the various segments together. In contrast to other valve reformation structures, implant members such as implant members 1900 (FIGS. 19A-19D), 2000 (FIGS. 20A-20D) do not need to be positioned on tissue surrounding a valve, and then secured to the surrounding tissue and finally cinched together to alter the shape of the valve. Rather, in various embodiments, implant members such as implant members 1900, 2000 are secured to tissue anchors (i.e., FIGS. 3, FIGS. 4A-4B, FIGS. 5A-5D, FIGS. 6A-6B, FIGS. 7A-7C and FIGS. 8A-8D, by way of non-limiting example) that have been previously embedded or previously anchored into the tissue surrounding the orifice proximate at least three locations. It is noted that in some example embodiments, each tissue anchor is individually embedded into tissue, while in other example embodiments, the tissue anchors are embedded into the tissue as a group. In the previously described example embodiments, guide lines that are received or coupled to the embedded tissue are received by guide line receivers 1910, 2010 provided by respective ones of implant members 1900, 2000 to provide a physical path for implant member 1900, 2000 to travel to the embedded tissue anchors. As the implant member 1900, 2000 travels towards the embedded tissue anchors, each of the guidelines is configured to receive a tensile force sufficient to apply force to bend or position implant member 1900, 2000 into its deployed or implantable configuration (i.e., the second configuration). In various example embodiments, at least some of the guide lines impart force to the implant member 1900, 2000 as it moves along the physical path to the embedded tissue anchors.

In various example embodiments, the implant member 1900, 2000 is appropriately sized and dimensioned so that the tensile force applied to each of the guide lines is sufficient to cause a portion of the tissue into which a respective tissue anchor is embedded to move towards the implant member 1900, 2000 as the implant member 1900, 2000 is positioned into its second configuration. In various example embodiments, the segments 1902, 2002 of respective ones of the implant member 1900, 2000 in the second configuration enclose at least partially, an area that is smaller than an area of an annulus of an orifice (e.g., a mitral valve) prior to a physical coupling between the implant member 1900, 2000 and the tissue. In various example embodiments, a circumference defined by a circle passing through at least three locations of the guide line receivers 1910, 2010 on a respective one of the implant member 1900, 2000 in the second configuration is smaller than a circumference of an annulus of the tissue orifice or valve prior to a physical coupling between the implant member 1900, 2000 and the embedded tissue anchors. In various example embodiments, a circumference defined by a circle passing through at least three locations of the guide line receivers 1910, 2010 on a respective one of the implant member 1900, 2000 in the second configuration is smaller than a circumference defined by a circle passing through at least three locations of the embedded tissue anchors prior to a physical coupling between the implant member 1900, 2000 and the embedded tissue anchors.

It is noted that the force applied by the anchoring maintains the implant member 1900, 2000 under tension in the desired implantable configuration when the implant member 1900, 2000 is finally secured to the tissue. Advantageously, implant member 1900, 2000 is positionable between a first configuration in which respective ones of segments 1902, 2002 are articulable with respect to one another such that the implant member 1900, 2000 is manipulable to a size and dimension to be deliverable via a catheter and a second configuration in which the segments 1902, 2002 form a structure sufficiently rigid to affect a shape of a tissue valve or orifice in a desired manner. In this regard, each of the implant member 1900, 2000 has a reduced bending stiffness in at least one dimensional plane in the first configuration to allow it to be deliverable via a catheter and an increased bending stiffness in the at least one dimensional plane sufficient to form a structure sufficiently rigid to affect the shape of a tissue valve or orifice in a desired manner. In various example embodiments, the guide lines and embedded tissue anchors apply tension to the implant member 1900, 2000 in the second configuration that is sufficient to restrain disengagement of a respective one of a coupled segment 1902, 2002 with a stop associated with the coupled segment. In various example embodiments, the guide lines and embedded tissue anchors apply tension to the implant member 1900, 2000 in the second configuration that is sufficient to flex at least one of a respective segment 1902, 2002 while the segment is engages with an associated stop. The applied tension provided to the implanted implant member 1900 in these example embodiments may reduce wear on the components of the associated hinges 1904 as the implanted implant member 1900 is subsequently repeatedly stressed by the recipient's cardiac cycle which can be in the millions of cycles. The applied tension provided to the implanted implant member 2000 in these example embodiments may reduce fatigue effects as the implanted implant member 2000 is subsequently repeatedly stressed by the recipient's cardiac cycle. While some of the described embodiments may employ a cable between end segments of the articulated structure as an implant cross member, adjacent pairs of the segments are coupled together via respective hinges rather than a cable.

The implant member 1900, 2000 may, for example, have a length (e.g., measured from guide receiver 1910a to 1910b) of from approximately 24 mm to approximately 38 mm, inclusive. Implant members 1900, 2000 may be available in a variety of lengths, for instance in 2 mm increments, to accommodate various valve sizes. The implant members 1900, 2000 may have a thickness of approximate 2 mm, although other thickness may be employed. The width of the segments of the implant members 1900, 2000 may, for example, be approximately 2 mm, although other widths may be employed. The implant members 1900, 2000 may, for example, have a height that is between approximately 30% and approximately 50% of the longitudinal length. The implant members 1900, 2000 may, for example, have a height that is between approximately 60% and approximately 65% of the longitudinal length, for example 63% of the longitudinal length. Such ratio may provide sufficient force to approximate the anterior-posterior dimension of a mitral valve.

In some embodiments, the implant member 1900, 2000 may, for example, have an arcuate, annular or C-shape. The implant member 1900, 2000 may be sized and dimension to encompass over a third or over half (i.e., substantially) of the orifice. For example, the arcuate, annular or C-shape may be sized and dimensioned to overlie part of an annulus of a mitral valve of a heart, surrounding approximately half the mitral value. Such may advantageously allow the anterior-posterior dimension of the mitral valve to be modified (e.g., reduced). Implant members such as implant members 1900, 2000 may be formed from or comprise a variety of materials. The materials may include a biocompatible material which does not react in or with the tissue or bodily fluids. For example, the implant members 1900, 2000 and/or implant cross member 2050 may be formed of metals such as Nitinol, stainless steel, platinum, iridium, titanium, or polymers such as polytetrafluoroethylene (PTFE) or silicone. Also for example, the implant members 1900, 2000 and/or implant cross member 2050 may be formed tissue (e.g., allograft, autograft).

The implant members 1900, 2000 and/or implant cross member 2050 may have a textured exterior. Alternatively, implant members 1900, 2000 and/or implant cross member 2050 may take the form of a tissue scaffold, for instance a scaffold constructed using 3-D printing techniques. Such textured surface or scaffold may encourage biological overgrowth. The implant members 1900, 2000 and/or implant cross member 2050 may carry one or more functional coatings or layers. Such may either encourage or inhibit formation of scarring, may deliver (e.g., elute) a therapeutic agent to the organ or blood. Such may include gold, heparin, carbon nano-composite, silicon carbide, titanium-nitride-oxide, phosphorylcholine, etc.

Figures 21A, 21B:
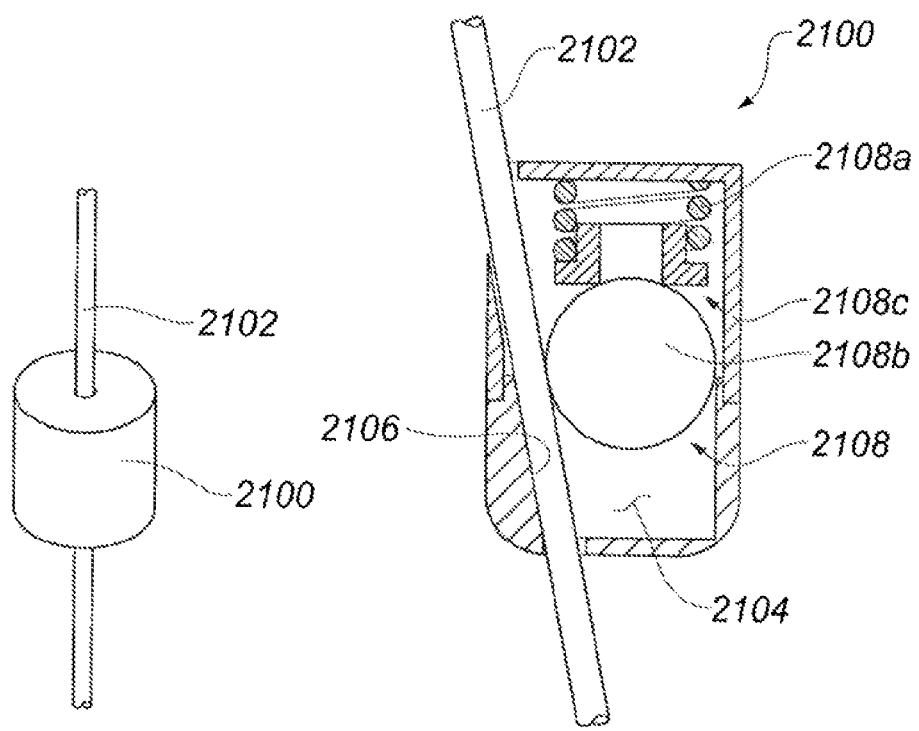
FIG. 21A is an isometric view of a fastener that fastens to a guide line, according to one illustrated embodiment
FIG. 21B is a cross-sectional view of the fastener and guide line of FIG. 21A.

FIGS. 21A and 21B show a fastener 2100 that fastens to a guide line such as a guide wire 2102, according to one illustrated embodiment.

The fastener 2100 has a cavity 2104 which provides a passage through the fastener 2100 for the guide line (e.g., Nitinol wire). The cavity 2104 may include openings in two opposed surfaces of the fastener 2100 to provide a passage for the guide line or guide wire 2102. The cavity 2104 may have a sloped wall 2106. The cavity 2104 may contain one or more cams or clutches 2108, for instance a spring 2108a and ball 2108b. The ball 2108b is biased toward the sloped wall 2106 by the spring 2108a. While illustrated as a coil spring, other types of springs may be employed. The cam or clutch 2108 may include a seat 2108c which has a stem to retain the spring 2108a and an aperture or concavity to retain the ball 2108b. The ball 2108b frictionally engages the guide line or guide wire 2102 against the sloped wall 2106 in response to movement of the fastener 2100 along the guide line 2102 toward an embedded tissue anchor (not shown in FIG. 21A or 21B). The fastener 2100 may be a unidirectional or a one way fastener or clutch, allowing the fastener 2100 to ride or move along the guide line or guide wire 2102 in one direction, but resisting movement in the opposite direction. Such may be employed to secure (e.g., cinch) the fastener 2100 against the implant member (not shown in FIG. 21A or 21B) percutaneously, to secure the implant member to the tissue anchors which are embedded in the tissue. Other cams or clutches may be employed. For instance, an arcuate section pivotally mounted and biased, for example by a leaf spring, to engage the guide line or guide wire, may be used. The fastener 2100 may be comprised of a biocompatible material, for example a metal that does not react with bodily tissues or fluids. The fastener 2100 may include a tubular housing, which may be cylindrical. An end cap may be secured to the housing, for example via spot welding. The fastener 2100 may, for example, have a total volume of 8 cubic millimeters. The ball 2108b may, for example, have a diameter of approximately 0.5 mm.

FIGS. 22A and 22B show a fastener 2200 that fastens a guide line 2202 to a tissue anchor 2204, according to another illustrated embodiment.

The fastener 2200 physically interacts with a fastening portion 2206 of the tissue anchor 2204. In particular, the fastener 2200 has a sloped outer surface or swaging surface 2208 that is received in a cavity 2210 of the fastening portion 2206 of the tissue anchor 2204. Engagement of the inner wall forming the cavity 2210 plastically deforms the fastener 2200, increasing the frictional force applied to the guide line 2202. Such can secure the fastener to the tissue anchor 2204, secure the guide line 2202 to the fastener 2200. The fastener 2200 is a bidirectional fastener, resisting movement of the guide line 2202 in either direction once swaged. Such may be employed to secure (e.g., cinch) the fastener against the implant member in its second configuration (not shown in FIG. 22A or 22B) to secure the implant member to the tissue anchors embedded in the tissue. While illustrated with the fastener 2200 having a sloped surface 2208, in some embodiments, the inside wall forming the cavity 2210 may be sloped to achieve a similar result. The fastener 2200 may include a peripheral flange 2212 to form a head. The size of the peripheral flange 2212 may be larger than the openings of the implant member that receive the guide lines 2202. The fastener 2200 may be comprised of a biocompatible material, for example a metal that does not react with bodily tissues or fluids.

Fasteners other than fasteners 2100, 2200 generally described above may be employed in various example embodiments. While illustrated as separate from the implant member, the fasteners may be incorporated into the implant member. For example, the fasteners 2100, 2200 may be secured to the implant member. For instance, the fasteners 2100, 2200 may be secured in apertures or recesses of the implant member, for example via press fit, swaging, and/or adhesives, to become an integral part of the implant member. Alternatively, the fasteners 2100, 2200 may be formed as a unitary, single piece portion of the implant member. For instance, as illustrated in FIG. 22C, a fastener may take the form of a resilient member, such as a tab or pawl 2250, that extends into the guide line receiver 2252 of an implant member 2254, and which allows the guide line to easily advance in one direction but which resists retreat of the guide line in the opposite direction. In each of these examples, a passage through the fastener 2100, 2200, 2250 may serve as the guide line receiver.

Figure 24A:
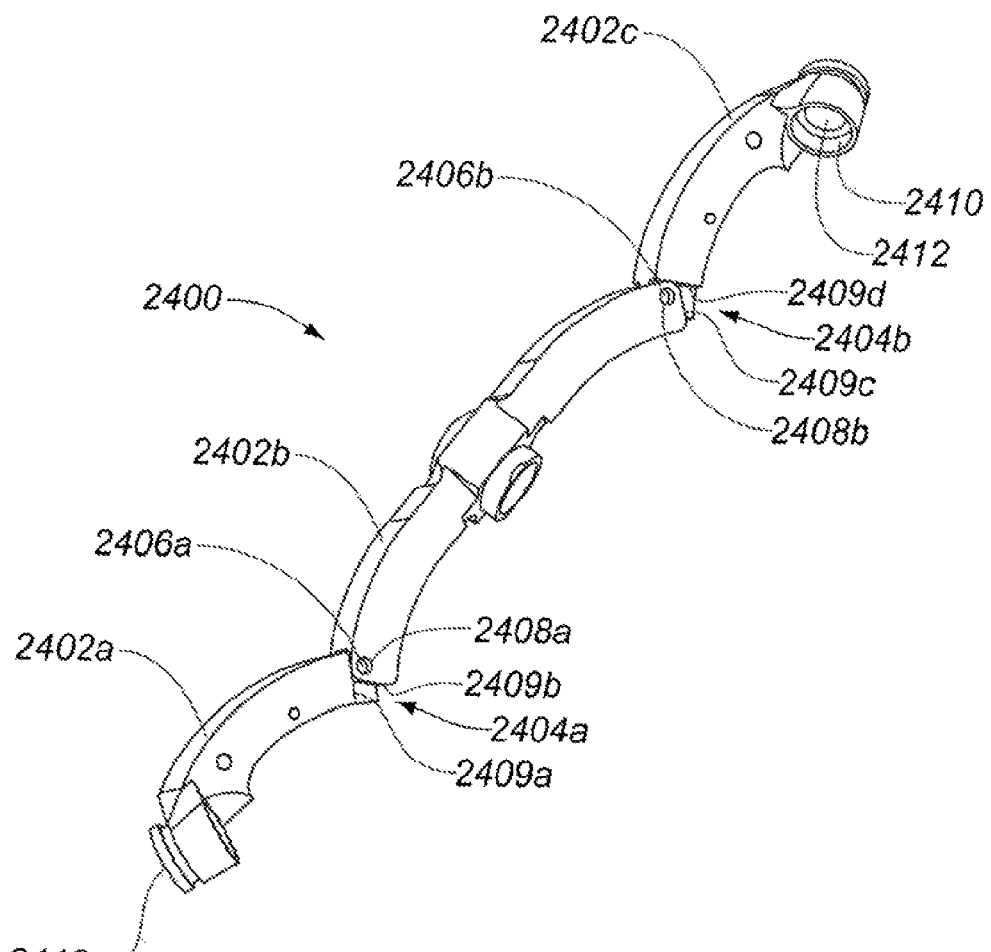
FIG. 24A is an isometric view of an implant member according to another illustrated embodiment, the implant member shown in a delivery configuration.
Figure 24B:
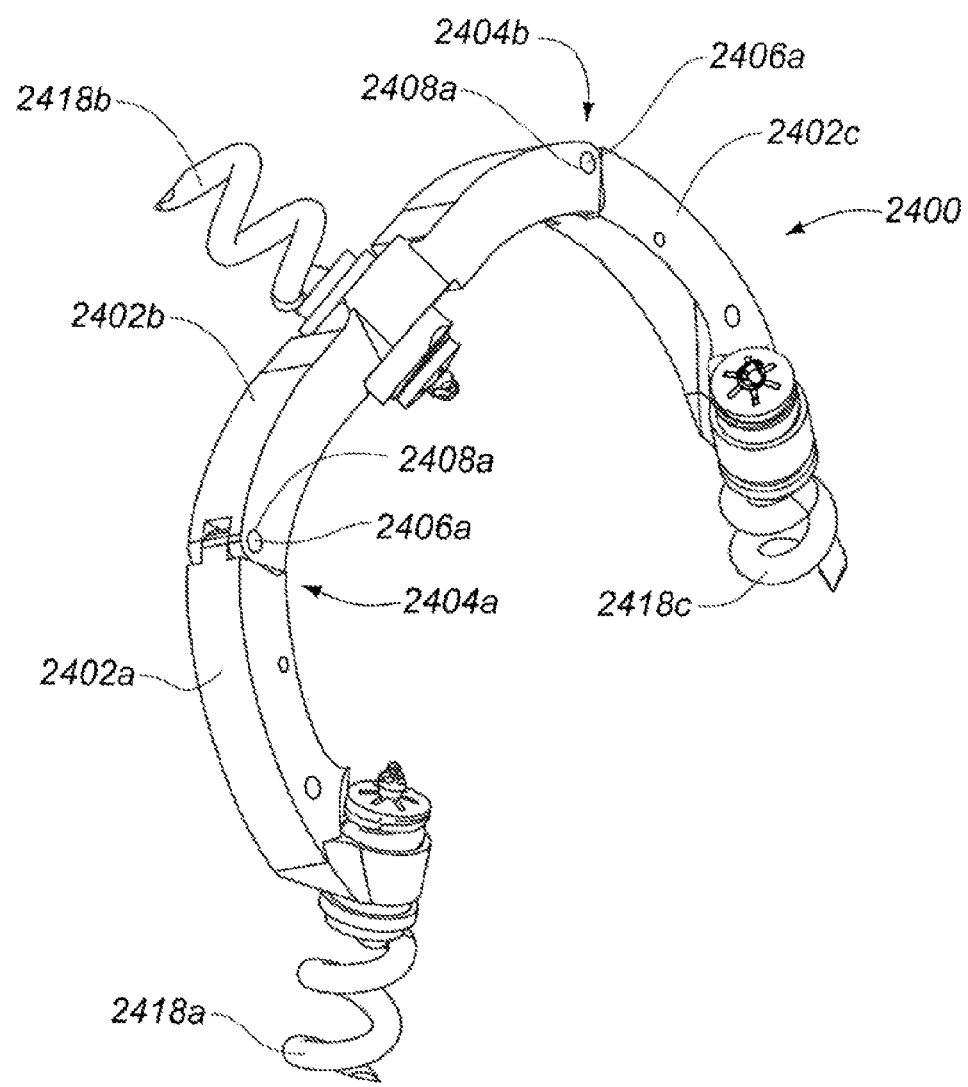
FIG. 24B is an isometric view of the implant member of FIG. 24A shown mated with a plurality of tissue anchors.

FIGS. 24A-24H show an implant member 2400, according to one illustrated embodiment. In particular, FIG. 24A shows the implant member 2400 in a first configuration that is representative of one of a delivery configuration, an unanchored configuration or an untensioned configuration, while FIG. 24B show the implant member 2400 in a second configuration that is representative of one of an implantable configuration, a deployed configuration, an anchored configuration or a tensioned configuration.

The implant member 2400 is similar to previously described implant member 1900 and may be used to reshape, reconfigure and/or reinforce an orifice in bodily tissue. For example, the implant member 2400 may be used to reshape, reconfigure and/or reinforce a valve, for instance a natural valve or an artificial valve. The valve may, for example take the form of a mitral, tricuspid, pulmonary and/or aortic valve of the heart. Alternatively, the valve may take the form of another valve in another organ of the body.

The implant member 2400 has a plurality of arcuate segments 2402a-2402c (collectively 2402). While three segments 2402 are illustrated, the implant member 2400 may include additional segments. The total number of segments 2402 may be based on the size of the valve with which the implant member 2400 will be used. The total number of segments 2402 may additionally or alternatively be based on a largest lateral dimension that may be accommodated by a given or desired catheter (i.e., diameter of catheter lumen). For instance, in manner similar to that described for implant member 1900, employing a greater number of segments 2402 means that each segment may have a smaller height, while still achieving a desired lateral dimension or height of the overall implant member 2400 when in the second configuration.

The segments 2402 are physically coupled to one another, and in at least some configurations are articulated for movement with respect to one another, for example pivotal movement. The implant member 2400 includes a number of hinges 2404a, 2404b (collectively 2404) pivotally coupling neighboring ones of the segments 2402. Each hinge 2404 may include a hinge pin 2406a, 2406b (collectively 2406) received via throughholes 2408a, 2408b (collectively 2408) in the segments 2402. Each hinge pin 2406 should be fixedly received in the throughhole 2408 to ensure that the hinge pin 2406 does not become dislodged after implantation. The hinge pin 2406 may be swaged in the throughhole 2408, and may additionally or alternatively be fixed using other mechanisms. The locations of the hinge pins 2406 of the hinges 2404 may be offset from a longitudinal centerline (i.e., the arc that passes longitudinally through the geometric center between the longitudinal arcuate edges) of the respective one of the arcuate segments 2402. Alternatively, the hinge pins 2406 may lie along the longitudinal centerline.

The segments 2402 include stops 2409a-2409d (collectively 2409) proximate the hinges 2404. The stops 2409 on neighboring ones of the segments 2402 cooperatively interact by engaging one another to prevent the segments 2402 from being pivoted past a defined angle with respect to one another. The stops 2409 thus serve to restrain the segments 2402 from further articulation in one direction. While illustrated as simple complimentary engagement surfaces, the stops may take other forms. For example, stops may take the form of a detent or other lock structure. Stops 2409 may lock the segments 2402 from moving along each of two opposing directions when the implant member is in the second configuration. Stops 2409 may also provide torsional stiffness to the hinges 1904. Stops 2409 may also impart a greater bending stiffness to a portion of the implant member 2400 in its second configuration than it has in its first configuration.

As illustrated in FIGS. 24A and 24B, the segments 2402 of the implant member 2400 may be moved with respect to one another into a first configuration, which in this illustrated embodiment is representative of a delivery configuration or unanchored configuration or untensioned configuration. In the first configuration, the implant member 2400 is sized and dimensioned to be deliverable via a catheter. In the first configuration, the implant member 2400 may have an elongated, scalloped, crenulated or serpentine profile, as best illustrated in FIG. 24A. A maximum longitudinal dimension in the first configuration is relatively long as compared to the maximum longitudinal dimension in the second configuration. As illustrated in FIGS. 24A and 24B, the segments 2402 of the implant member 2400 may be moved with respect to one another into the second configuration representative of an implantable or deployed or anchored or tensioned configuration. In the second configuration, the implant member 2400 has an arcuate shape or profile. The arcuate shape is sized and dimensioned to encompass at least part of an orifice. For example, the arcuate shape may be sized and dimensioned to overlie part of an annulus of a mitral valve of a heart. In the second configuration, the dimensions of the implant member 2400 are too large to be accommodated by a typical catheter sheath. In particular, a lateral dimension or height of the implant member 2400 is too large to be received by a lumen of the catheter sheath. Advantageously, the articulated segments 2402 of implant member 2400 allow implant member 2400 to be delivered percutaneously in a first configuration while assuming a structure in a second configuration that is sufficiently rigid to affect a shape of the tissue orifice in a desired manner. In this example embodiment, implant member 2400 is shown coupled with each helical tissue anchors 2418a, 2418b and 2418c (collectively tissue anchors 2418) which have been previously embedded into tissue (not shown).

In a manner similar to other described embodiments, forces or tension may be applied to the implant member 2400 at the guide line receivers 2410 (one called out in FIG. 24A), for instance via embedded helical tissue anchors and/or wires and/or sutures (not shown in FIGS. 24A and 24B). Such may tension the implant member 2400 into the second configuration (FIG. 24B), while the stops 2409 prevent the segments 2402 of implant member 2400 from articulating past the second configuration. Such results in implant member 2400 having a rigid structure in the second configuration.

In this illustrated embodiment, implant member 2400 has a plurality of tissue anchor receivers 2412 (two called out in FIG. 24A), each of the tissue anchor receivers 2412 configured to receive or mate with a respective one of the embedded helical tissue anchors 2418 when implant member is positioned in the second configuration. In this example embodiment, each of the guide line receivers 2410 is co-axially aligned with a respective one of the tissue anchor receivers, although other alignments may be employed in other example embodiments. As implant member 2400 travels along the guide lines extending from the embedded helical tissue anchors 2418, segments 2402 articulate about respective hinges 2404 to position the implant member in the second configuration. Tensile forces on the guide lines draw portions of the tissue into which the helical tissue anchors 2418 are embedded towards implant member 2400 as implant member 2400 transitions into the second configuration. Tensile forces on the guide lines move portions of the tissue into which respective ones of the helical tissue anchors 2418 are embedded into locations where each of the embedded helical tissue anchors 2418 is coupled with a respective one of the tissue anchor receivers 2412 when the implant member 2400 is in the second configuration. In this illustrated embodiment, various portions of the tissue are moved to desired locations and are maintained in these locations by the coupling of implant member 2400 to the embedded helical tissue anchors 2418 via tissue anchor receivers 2412. In this illustrated embodiment, the coupled embedded helical tissue anchors 2418 may cause portions of some of the segments 2402 to flex against associated stops 2408. In this illustrated embodiment, the coupled embedded helical tissue anchors 2418 tension implant member 2400 in the second configuration. The tension in the coupled implant member 2400 in the second configuration may be sufficient to reduce a pivoting movement of at least some of the segments 2402 about their associated hinges 2404 during the recipients subsequent cardiac cycle.

Figure 24C:
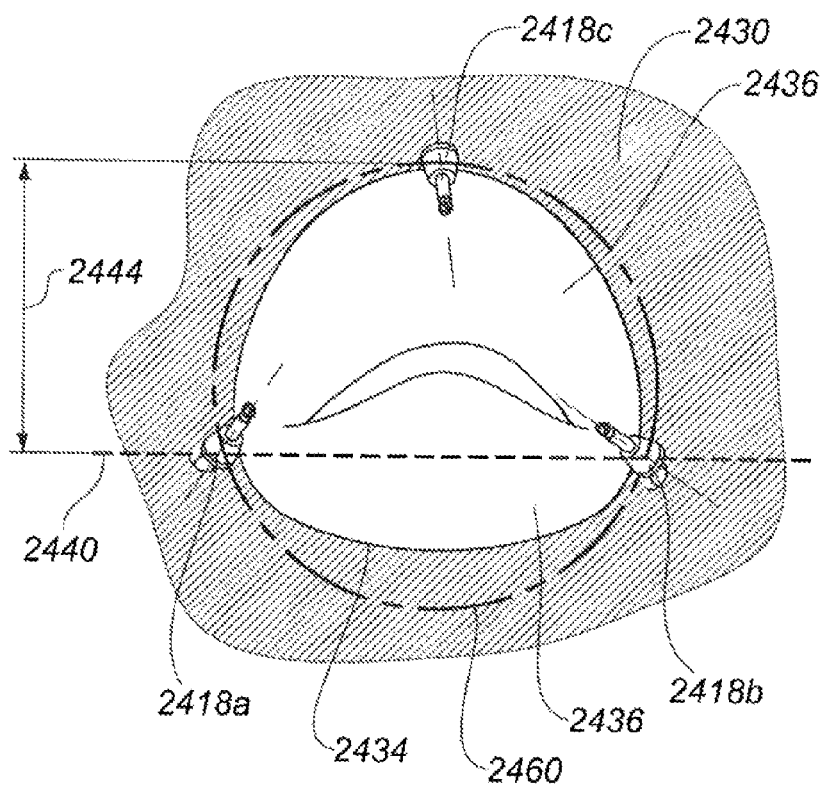
FIG. 24C shows a plurality of tissue anchors embedded in a tissue according to an illustrated embodiment.

The locations of the embedded tissue anchors 2418 and the locations of their respective tissue anchor receivers 2412 can be configured to alter a shape of a tissue valve or orifice in a desired manner. For example, FIG. 24C shows each of a first helical tissue anchor 2418a, a second helical tissue anchor 2418b and a third helical tissue anchor 2418c (collectively helical tissue anchors 2418) embedded into a respective location about a periphery of an orifice in a tissue 2430. In this example embodiment, a location of the embedded third tissue anchor 2418c is laterally offset by a first distance 2244 from a first axis 2440 (i.e., shown in broken lines) that extends between a location of the embedded first helical tissue anchor 2418a and a location of the embedded second helical tissue anchor 2418b. In this example embodiment, helical tissue anchors 2418 are embedded into tissue 2430 prior to a coupling with implant member 2400. In this example embodiment, the helical tissue anchors 2418 are embedded into tissue 2430 that forms part of a heart. Specifically, the helical tissue anchors 2418 are embedded about a mitral annulus 2434 within a left atrium. In this example embodiment, the location of each of the embedded helical tissue anchors 2418 is proximate to mitral annulus 2434. In this example embodiment, the location of each of the embedded helical tissue anchors 2418 is proximate to a longitudinal axis of the helical tissue anchor 2418. It is understood that the locations of the embedded helical tissue anchors 2418 can be specified relative to other datums in other example embodiments. In some example embodiments, each of the helical tissue anchors 2418 is transported sequentially through a catheter to their respective implantation locations while in other example embodiments, two or more of the helical tissue anchors 2418 are transported as a group through a catheter to their respective implantation locations. In some example embodiments, each helical tissue anchor 2418 is implanted sequentially while in other example embodiments, two or more of the helical tissue anchors 2418 are implanted at substantially the same time or concurrently.

Figure 24D:
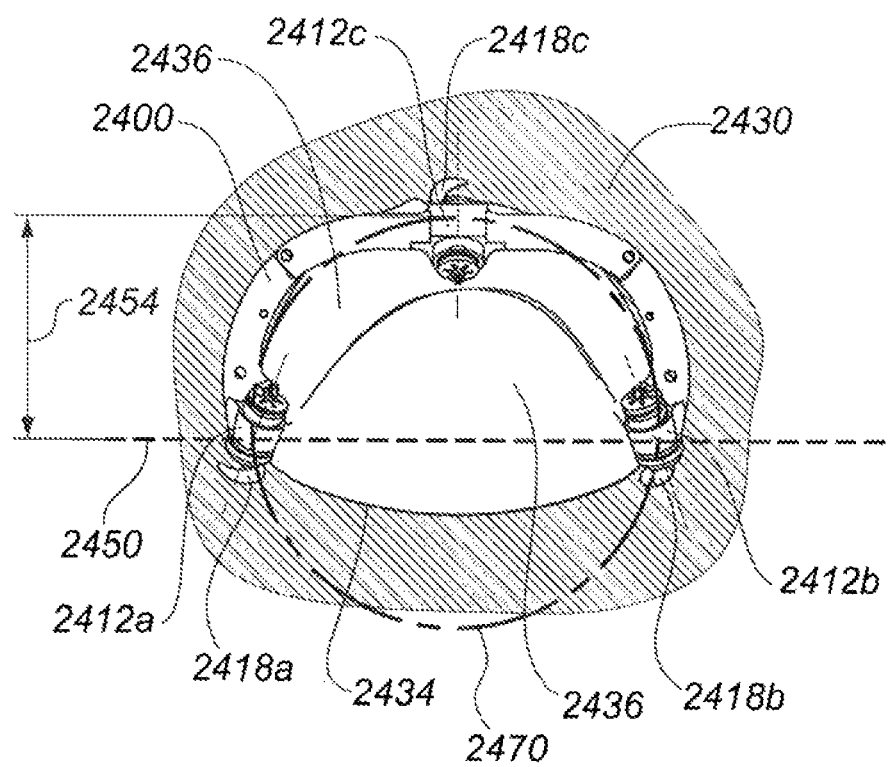
FIG. 24D shows an implant member coupled with the embedded tissue anchors of FIG. 24C.

FIG. 24D shows implant member 2400 coupled with the helical tissue anchors 2418 after they have been embedded into tissue 2430. Implant member 2400 is reconfigurable between the first configuration and the second configuration and is selected to include at least a first tissue anchor receiver 2412a corresponding to the first helical tissue anchor 2418a, a second tissue anchor receiver 2412b corresponding to the second helical tissue anchor 2418b, and a third tissue anchor receiver 2412c corresponding to the third helical tissue anchor 2418c. First tissue anchor receiver 2412a, second tissue anchor receiver 2412b and third tissue anchor receiver 2412c are collectively referred to as tissue anchor receivers 2412. As shown in FIG. 24D, implant member 2400 can be selected such that a location of the third tissue anchor receiver 2412c on the implant member 2400 in the second configuration is laterally offset by a second distance 2454 from a second axis 2450 (i.e., shown in broken lines) that extends between a location of the first tissue anchor receiver 2412a on the implant member 2400 and a location of the second tissue anchor receiver 2412b on the implant member 2400 such that the second distance 2454 is smaller than the first distance 2444. In this example embodiment, the location of each tissue anchor receiver 2412 is proximate to a longitudinal axis of the tissue anchor receiver 2412. It is understood that the locations of the tissue anchor receivers 2412 can be specified relative to other datums in other example embodiments.

As shown in FIG. 24D, a coupling between the tissue anchor receivers 2418 and the embedded helical tissue anchors 2418 will affect a shape of the mitral annulus 2434 which can be used to reposition mitral valve leaflets 2436 relative to one another in a desired way. A coupling between the tissue anchor receivers 2412 and the embedded helical tissue anchors 2418 will cause a portion of the tissue 2430 into which the third helical tissue anchor 2412c is embedded to move relative to another portion of the tissue 2430 in a desired way. Other portions of the tissue 2430 can be moved in a similar fashion based at least on the selection of an appropriately sized and dimensioned implant member 2400.

The relationship between the locations of the embedded helical tissue anchors 2418 and the locations of the tissue anchor receivers 2412 employed to alter a shape of mitral annulus 2434 can be illustrated in other ways. FIG. 24C shows that a circle 2460 (i.e., shown in broken line) can be dimensioned and sized to pass through the locations of the embedded helical tissue anchors 2418. In this example embodiment, a circumference of circle 2460 is greater than a circumference or perimeter of mitral annulus 2434. FIG. 24D shows that a circle 2470 (i.e., shown in broken line) can be dimensioned and sized to pass through the locations of the tissue anchor receivers 2412 when implant member 2440 is coupled with the embedded tissue anchors 2418. In this example embodiment, circle 2460 has a circumference that is greater than a circumference of circle 2470.

Figure 24E:
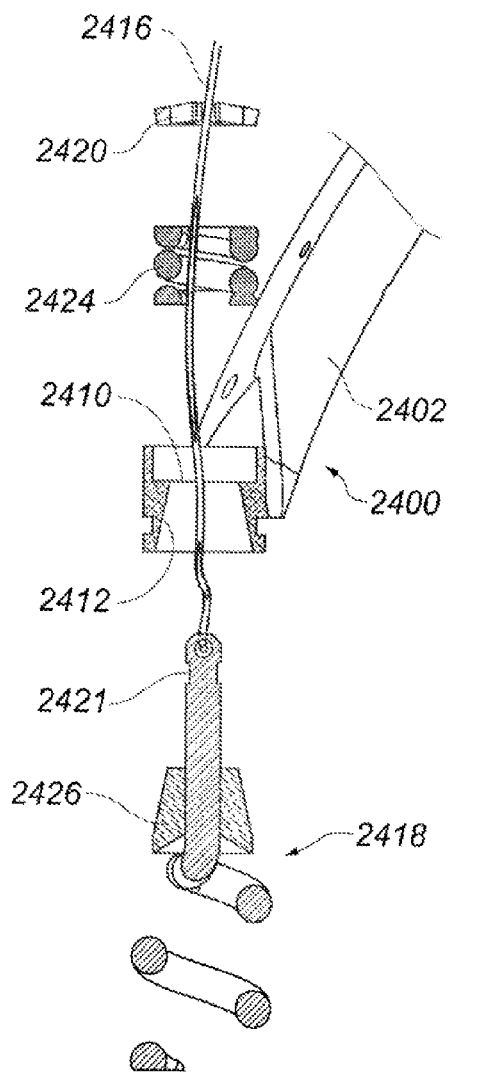
FIG. 24E is a sectional exploded view of a portion of the implant member of FIGS. 24A and 24B prior to a mating with an embedded tissue anchor.
Figure 24F:
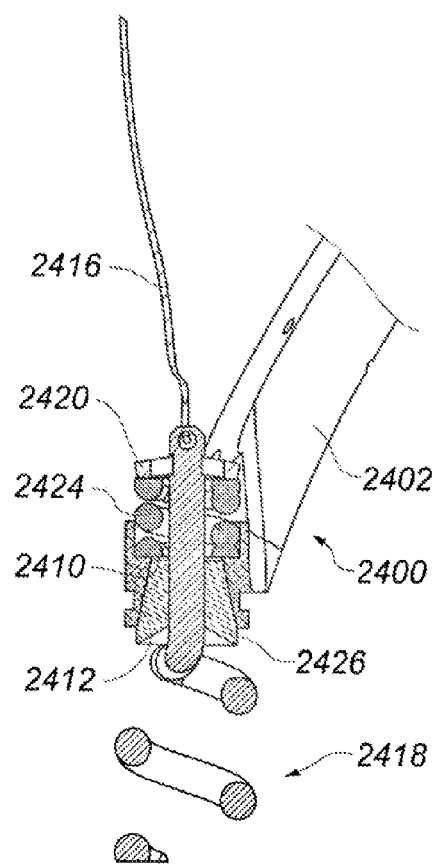
FIG. 24F is a sectional view of a portion of the implant member of FIGS. 24A and 24B mated with an embedded tissue anchor.
Figure 24G:
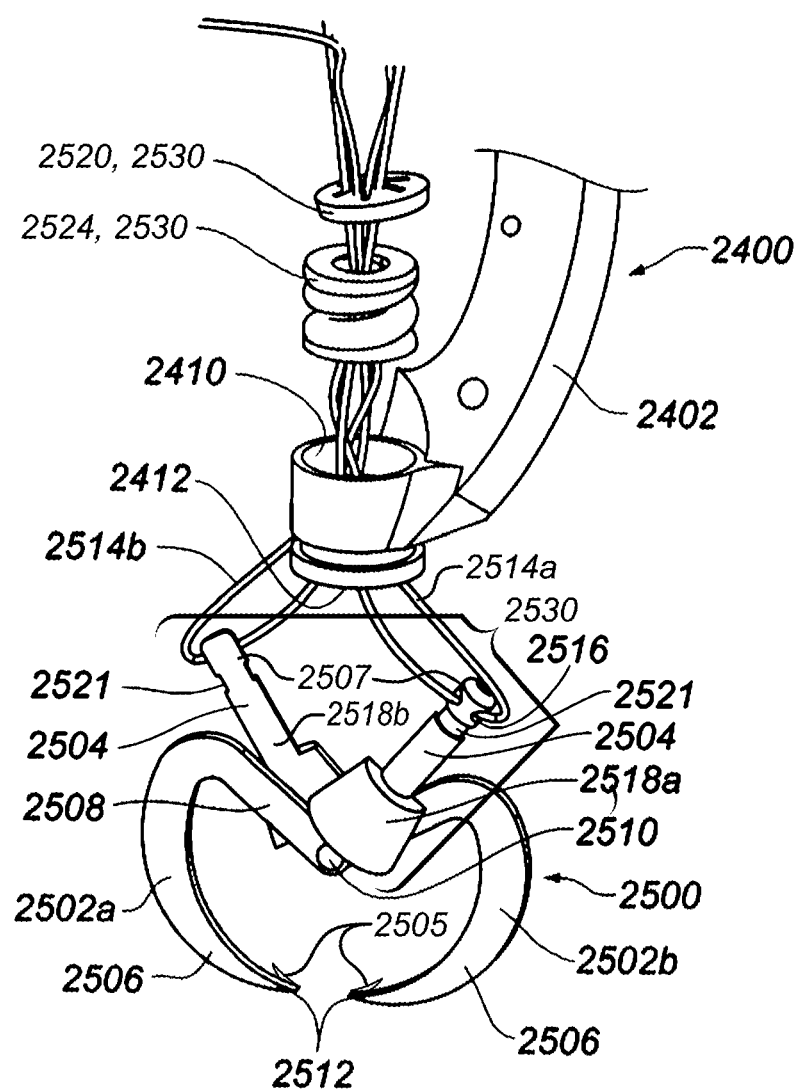
FIG. 24G is an exploded isometric view of a portion of the implant member of FIG. 24A and a grapple tissue anchor.
Figure 24H:
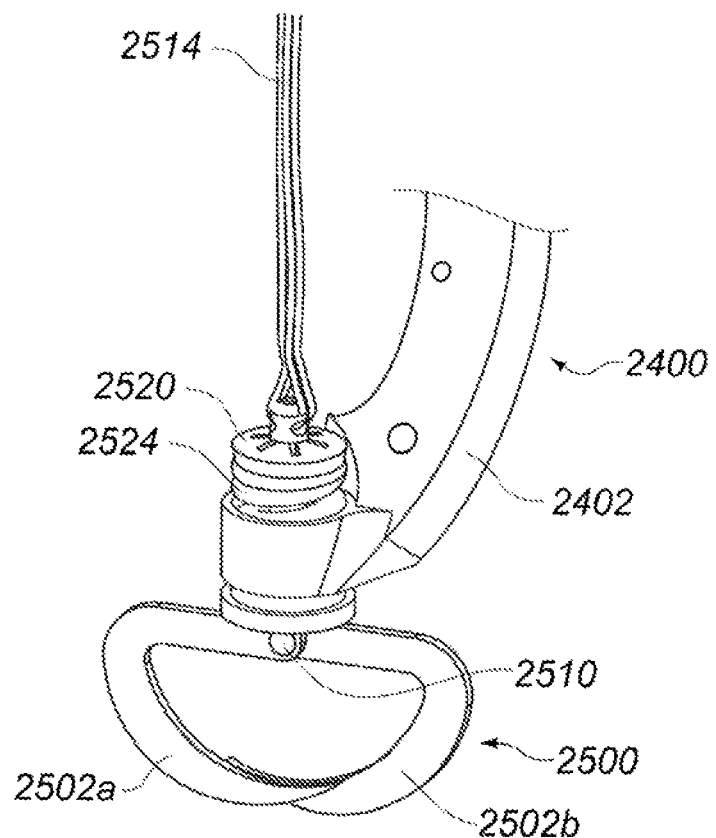
FIG. 24H is an isometric view of a portion of the implant member of FIG. 24A mated with a grapple tissue anchor.

FIGS. 24E and 24F respectively show a portion of a segment 2402 of implant member 2400 before and after a coupling with an embedded helical tissue anchor 2418. Tissue into which helical tissue anchor 2418 is embedded is not shown for clarity. In this illustrated embodiment, a guide line 2416 extends from embedded helical tissue anchor 2418 through the tissue anchor receiver 2412 and guide line receiver 2410 of segment 2402. Helical tissue anchor 2418 includes seat 2426 that is configured to mate or engage with tissue anchor receiver 2412. In this illustrated embodiment, seat 2426 and tissue anchor receiver 2412 include mating tapered surfaces. Seat 2426 and helical tissue anchor may be provided as a unitary structure. Alternatively, seat 2426 may be secured to helical tissue anchor 2418 by variety of methods including, adhesives, crimping, and heat fitting, by way of non-limiting example. In this illustrated embodiment, fastener 2420 is provided via guide line 2416 to secure segment 2402 to embedded helical tissue anchor 2418. Unlike other fasteners employed in other described embodiments that secure an implant member to the tissue by coupling with a guide line (e.g., fasteners 2100, 2200), fastener 2420 couples directly with the embedded helical tissue anchor 2418 itself as shown in FIG. 24F. In this illustrated embodiment, fastener 2420 includes snap-ring features configured to engage with groove 2421 in embedded helical tissue anchor 2418, although other well known securement mechanisms can be employed in other example embodiments. Spring 2424 is also provided via guide line 2416 such that it is captured between fastener 2420 and segment 2402. Spring 2420 can provide various functions which can include by way of non-limiting example: preloading segment 2402 against the embedded helical tissue anchor 2418 to reduce occurrences of the generation of potentially harmful wear particulates, or compensating for component manufacturing or assembly tolerances. Once implant member 2400 is secured to the embedded helical tissue anchor 2418, guide line 2416 can be decoupled from the embedded helical tissue anchor 2418. Decoupling can include cutting guide line 2416 or drawing guide line 2416 from an opening in embedded helical tissue anchor 2418 into which guide line 2416 is looped. It is noted that this aspect is not limited to helical tissue anchors such as helical tissue anchors 2418 and that other forms of tissue anchors may be employed. For example, FIGS. 24G and 24H respectively show a portion of a segment 2402 of implant member 2400 before and after a coupling with a grapple tissue anchor 2500 as per another example embodiment. Specifically, FIG. 24G shows an exploded isometric view of grapple tissue anchor 2500, the portion of segment 2402 and various other components while FIG. 24H shows an assembled isometric view into which grapple tissue anchor 2500 is secured to the portion of segment 2402 of implant member 2400. In this example embodiment, grapple tissue anchor 2500 is secured to implant member 2400 after grapple tissue anchor 2500 has been implanted or embedded into tissue. Tissue into which grapple tissue anchor 2500 is embedded is not shown for clarity.

Grapple tissue anchor 2500 includes at least two elongate members 2502a and 2502b (collectively elongated members 2502). Each of the elongated members 2502 includes a first end 2504, a second end 2506 and intermediate portion 2508 (only one called out in FIG. 24G) positioned along the elongate member 2502 between its first end 2504 and its second end 2506. Each of the second ends 2506 includes a tip 2512 shaped to penetrate the tissue. A barb 2505 may extend from the tip 2512. Each of the intermediate portions 2508 of the elongate members 2502 is pivotably coupled together by a pivot 2510. In this example embodiment, each of the elongated members 2502 includes an arcuate shaped portion. Specifically, in this example embodiment, each of the elongated members 2502 includes a portion between pivot member 2510 and the second end 2506 of the elongate member that extends along an arcuate path. In this example embodiment, each of the elongated members 2502 forms a prong.

Pivot member 2510 allows the elongated members 2502 to pivot with respect to one another to position the tips 2512 spaced relatively apart from one another at locations advantageous for penetrating the tissue. Upon further deployment of grapple tissue anchor 2500 into the tissue, the elongated members 2502 are pivoted relative to each other to cause tips 2502 to travel along a path through the tissue such that tips 2512 are positioned closer to one another than during their initial deployment into the tissue. This allows grapple tissue anchor 2500 to firmly anchor into the tissue. To illustrate this, FIG. 24G shows the elongate members 2502 pivoted to the opposed tips 2512 spaced such that position grapple tissue anchor 2500 would not be fully deployed into the tissue. Whereas FIG. 24H shows the elongate members 2502 pivoted to position the opposed tips 2512 such that grapple tissue anchor 2500 would be fully deployed into tissue. Those skilled in the art will appreciate that other deployment configurations can be employed by other grapple tissue anchors employed by various embodiments. For example, each of the elongated members 2502 can be configured to follow a different path through tissue during the deployment of the grapple tissue anchor 2500 into tissue. In some example embodiments, tips 2512 may, or may not overlap when grapple tissue anchor 2500 is fully deployed into tissue.

In this example embodiment, grapple tissue anchor 2500 is part of a tissue anchor system that includes at least one coupler 2530 that is physically coupled to at least one of the elongated member 2502, the at least one coupler 2530 being additionally configured to be received by implant member 2400 when the grapple tissue anchor 2500 is secured to implant member 2400. In this illustrated embodiment, a guide line 2514 extends from each elongated member 2502. As best shown in FIG. 24G, a guide line 2514a extends from elongate member 2502a and a guide line 2514b extends from elongate member 2502b. In this example embodiment, each guide line 2514 is sized to be received through an opening 2516 (only one called out in FIG. 24G). In this example embodiment, each of the guide lines 2514a and 2514b is looped through an associated one of the openings 2516 (e.g., eyelet). This allows each of the guide lines 2514 to be releasably coupled with an associated one of the elongated members 2502, the coupling being released by simply releasing an end of the guide line 2514 to allow it to be extracted through an associated one of the openings 2516.

In this example embodiment, guide lines 2514 are also each sized to be received through tissue anchor receiver 2412 and guide line receiver 2410 provided in segment 2402. In this example embodiment, guide lines 2514 are received through each of tissue anchor receiver 2412 and guide line receiver 2410 after grapple tissue anchor 2500 is embedded into tissue. In this particular embodiment, the at least one coupler 2530 includes a two component seat 2518 that is configured to mate or engage with tissue anchor receiver 2412 in a similar manner to seat 2426 employed by the embodiment illustrated in FIGS. 24E and 24F. Seat 2518 includes a first seat component 2518a coupled to elongated member 2502a and a second seat component 2518b coupled to elongate member 2502b. Each component of seat 2518 and an associated one of the elongated members 2502 can be provided in a unitary structure. Alternatively, each component of seat 2518 may be secured to an associated one of the elongated members 2502 by variety of methods including, adhesives, crimping, and heat fitting, by way of non-limiting example. When grapple tissue anchor 2500 is deployed into tissue, seat 2518 is configured to mate or engage with tissue anchor receiver 2412 in this illustrated example embodiment. In this illustrated embodiment, the seat components 2518a and 2518b include tapered surfaces configured to mate with a tapered surface provided by tissue anchor receiver 2412 in a manner similar to that employed by the embodiment illustrated in FIGS. 24E and 24F.

In this illustrated embodiment, fastener 2520 is provided via guide lines 2514 to secure segment 2402 to embedded grapple tissue anchor 2500. Unlike other fasteners employed in other described embodiments that secure an implant member to the tissue by coupling with a guide line (e.g., fasteners 2100, 2200), fastener 2520 couples directly with the embedded grapple tissue anchor 2500 itself as shown in FIG. 24H. In this illustrated embodiment, fastener 2520 includes snap-ring features configured to engage with a portion of groove 2521 provided in each of the elongated members 2502, when grapple tissue anchor 2500 is embedded into tissue. Spring 2524 is also provided via guide lines 2514 such that it is captured between fastener 2520 and segment 2402. Spring 2520 can provide various functions which can include by way of non-limiting example: preloading segment 2402 against the embedded grapple tissue anchor 2500 to reduce occurrences of the generation of potentially harmful wear particulates, or compensating for component manufacturing or assembly tolerances. Once implant member 2400 is secured to the embedded grapple tissue anchor 2500, guide lines 2514 can be decoupled from the embedded grapple tissue anchor 2500.

The present embodiments are not limited to securing grapple tissue anchor 2500 to articulated implant members such as implant member 2400. Other example embodiments may employ other members or mechanisms to secure tissue anchors such as grapple tissue anchor 2500 to an implant member employed in an implant procedure. Without limitation, various couplers 2530 can be employed to couple a tissue anchor such as grapple tissue anchor 2500 to an implant member. By way of non limiting example, coupler 2530 can include a clamp configured to clamp a portion of the implant member. Coupler 2530 can include an extension 2507 sized to be received within an opening provided in an implant member. Coupler 2530 can include an expansion member configured to expand and grip one or more surfaces of an implant member. Coupler 2530 can include a contraction member configured to contract and grip one or more surfaces of an implant member. Coupler 2530 can include detent or a snap-action component.

Figure 23A:
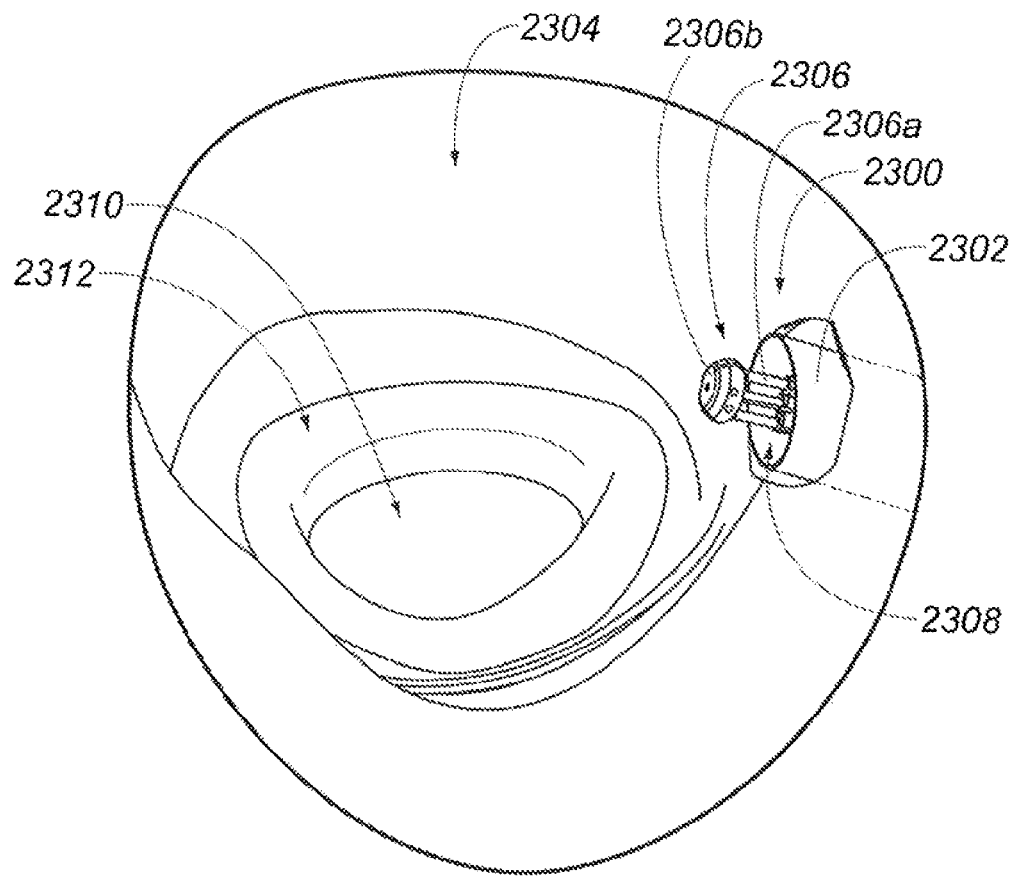
FIGS. 23A-23T are sequential schematic diagrams showing an implant procedure according to one illustrated embodiment, which includes placement of tissue anchors via an anchor guide frame at selected locations in an annulus surrounding a mitral valve of a left atrium of a heart and the securement of an implant member to the annulus via the tissue anchors.
Figure 23B:
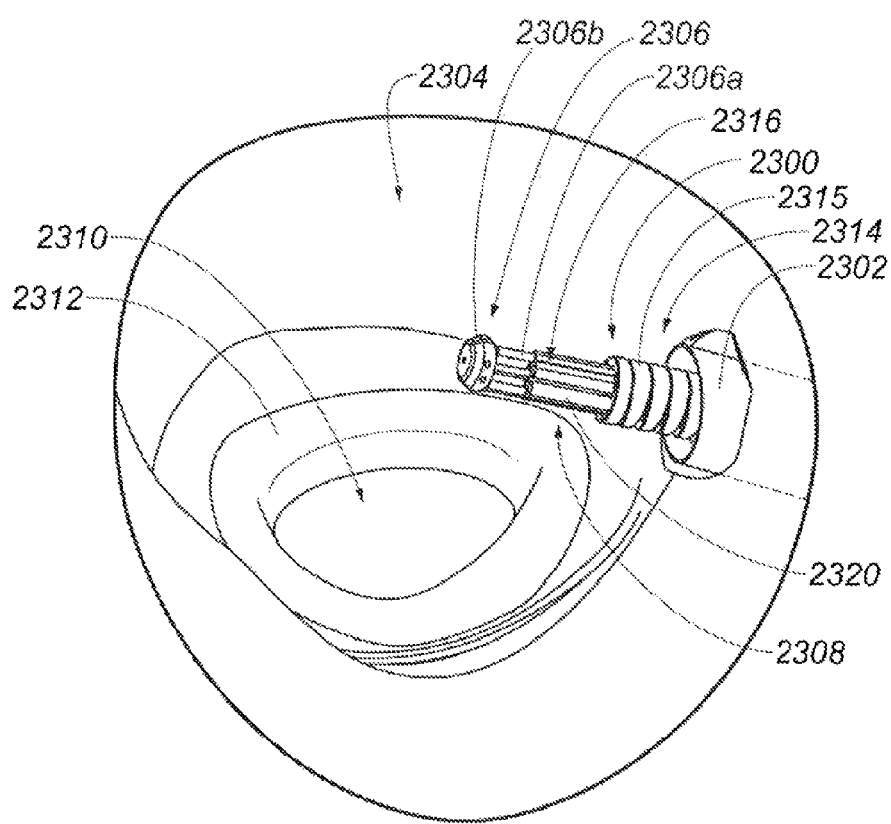
FIG. 23U a schematic diagram showing an implant member in the form of an annuloplasty ring attached to an annulus of a mitral valve via tissue anchors, guide wires and fasteners, according to one illustrated embodiment.
Figure 23C:
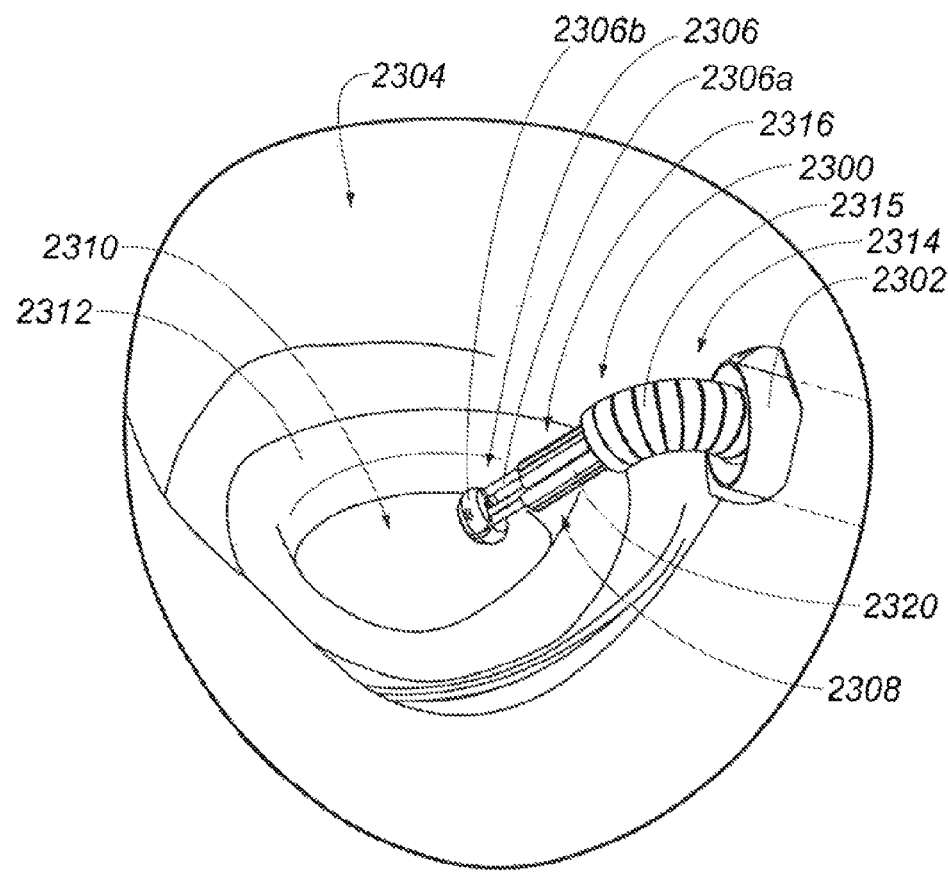
Figure 23D:
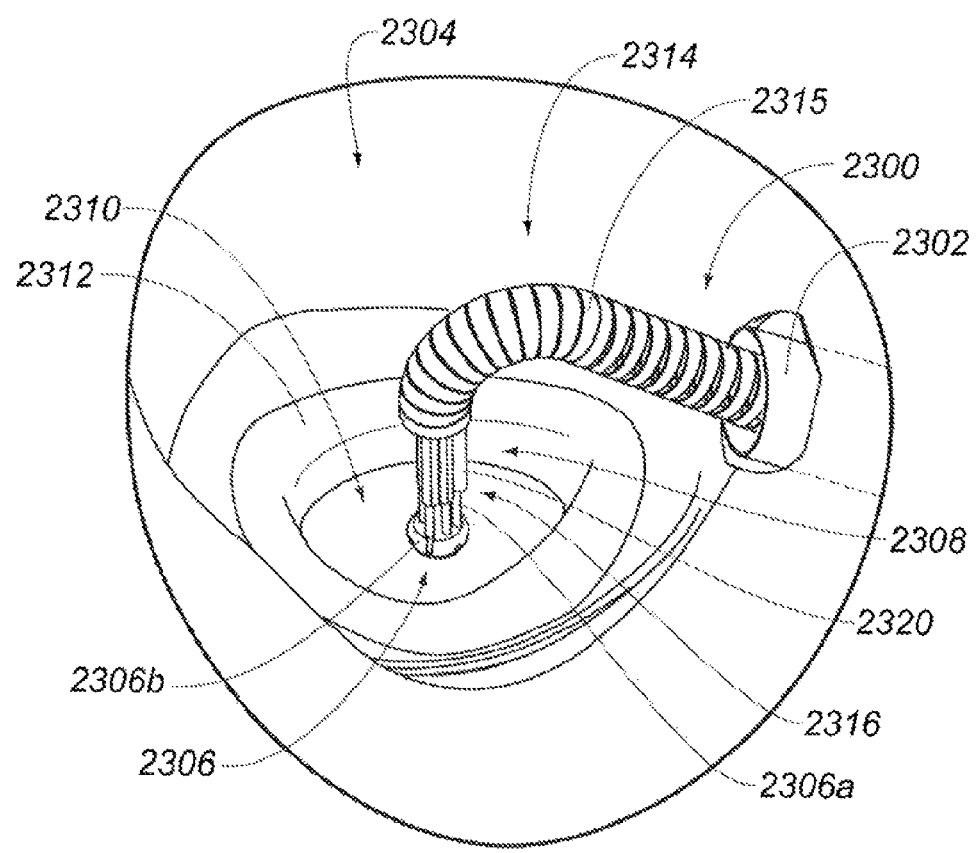
Figure 23E:
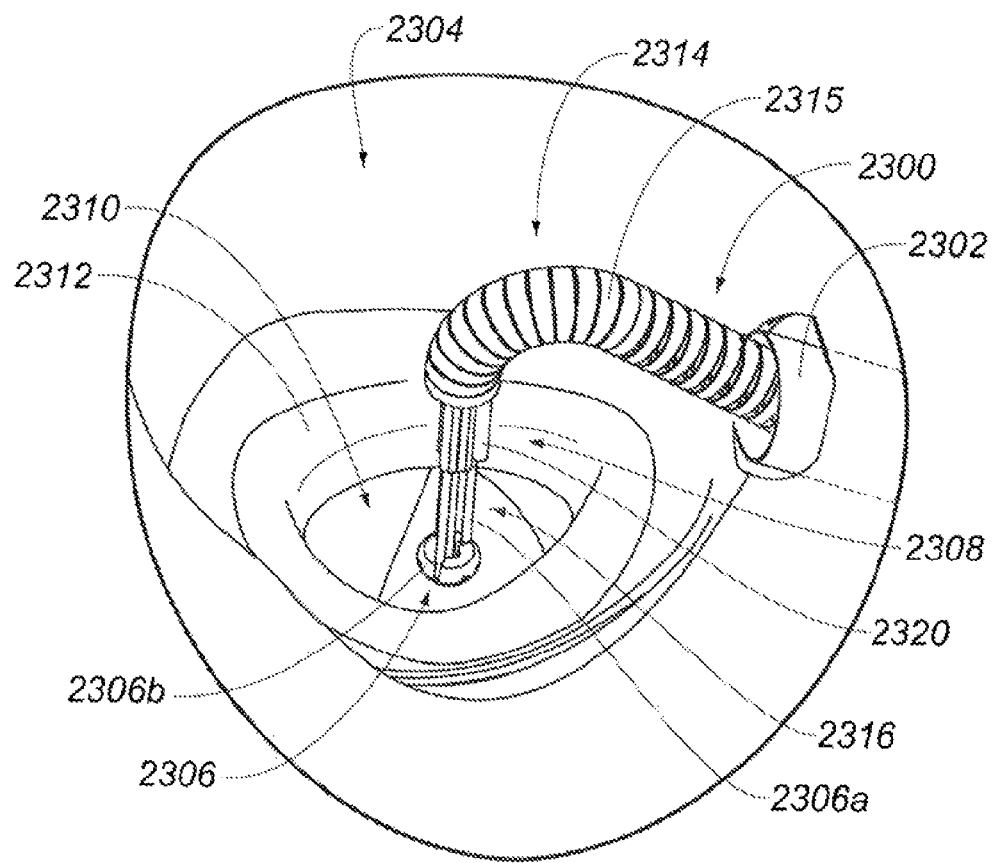
Figure 23F:
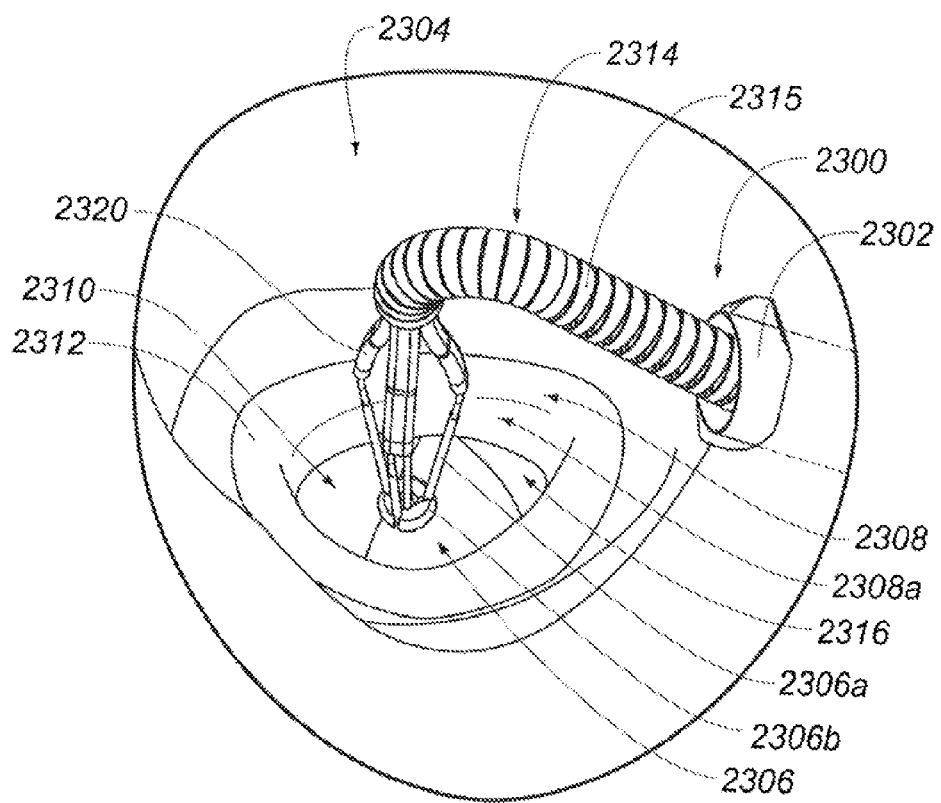
Figure 23G:
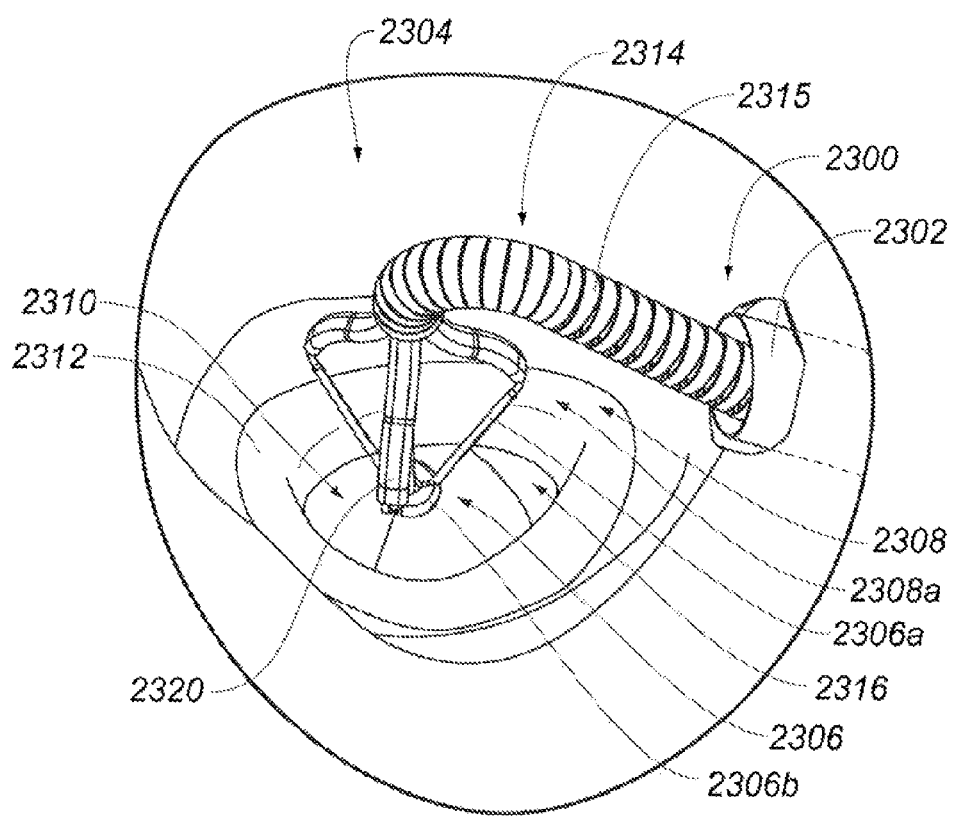
Figure 23H:
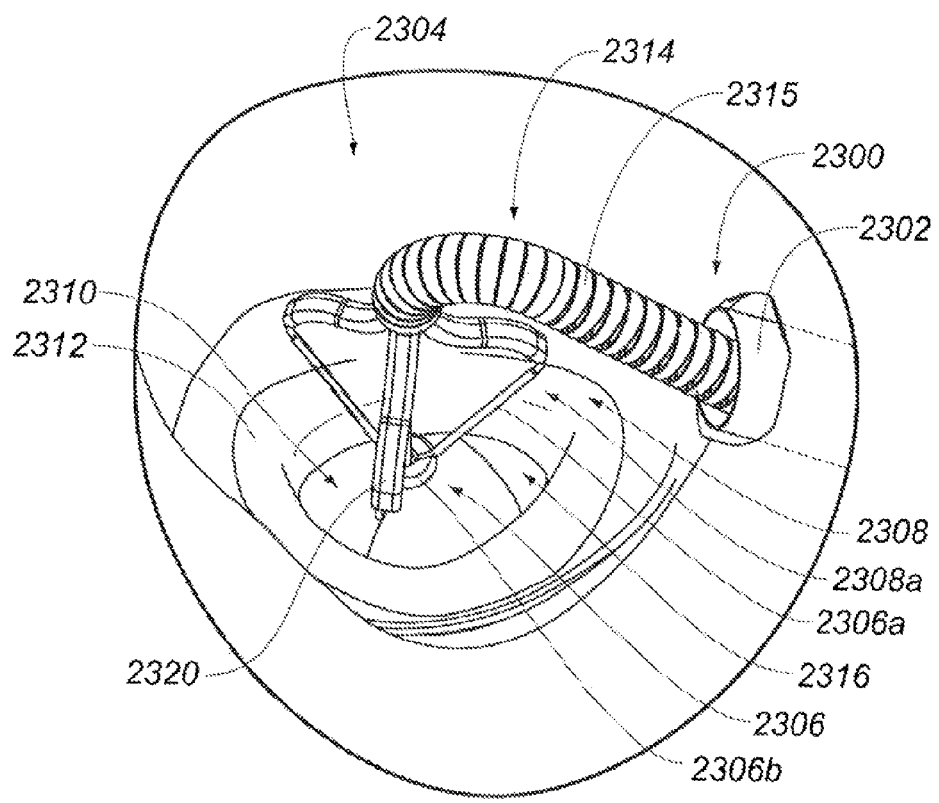
Figure 23I:
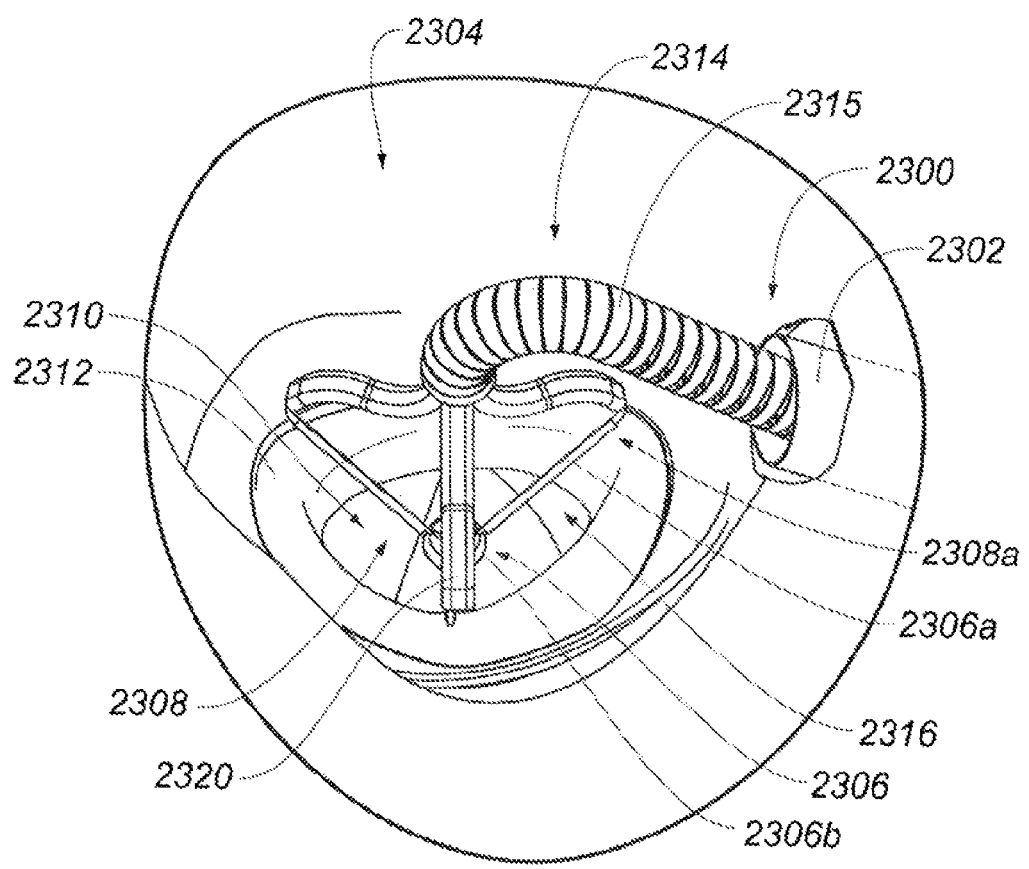
Figure 23J:
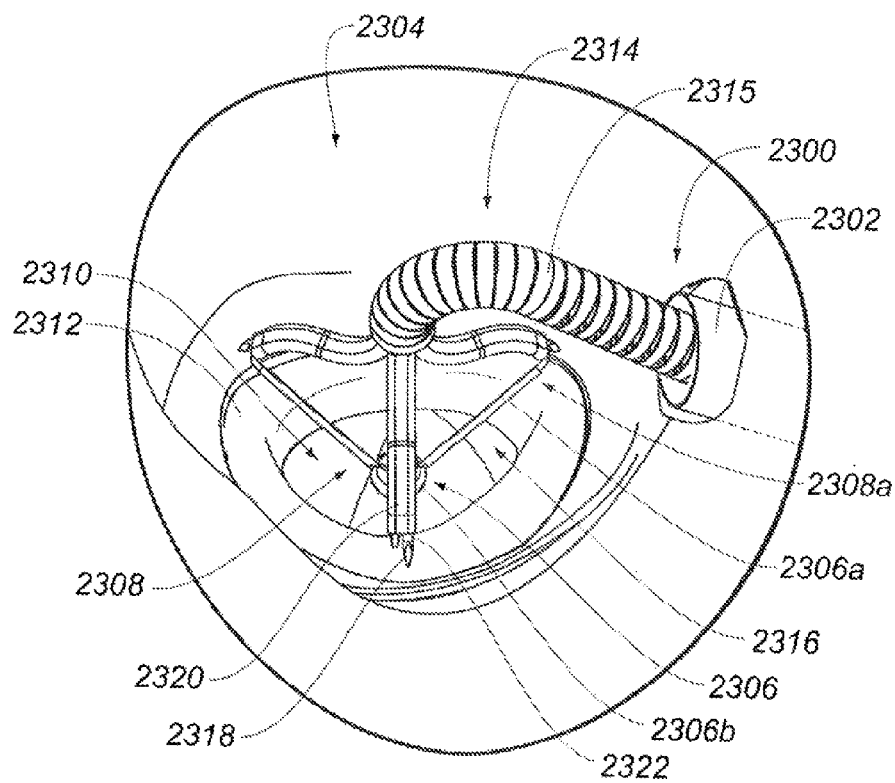
Figure 23K:
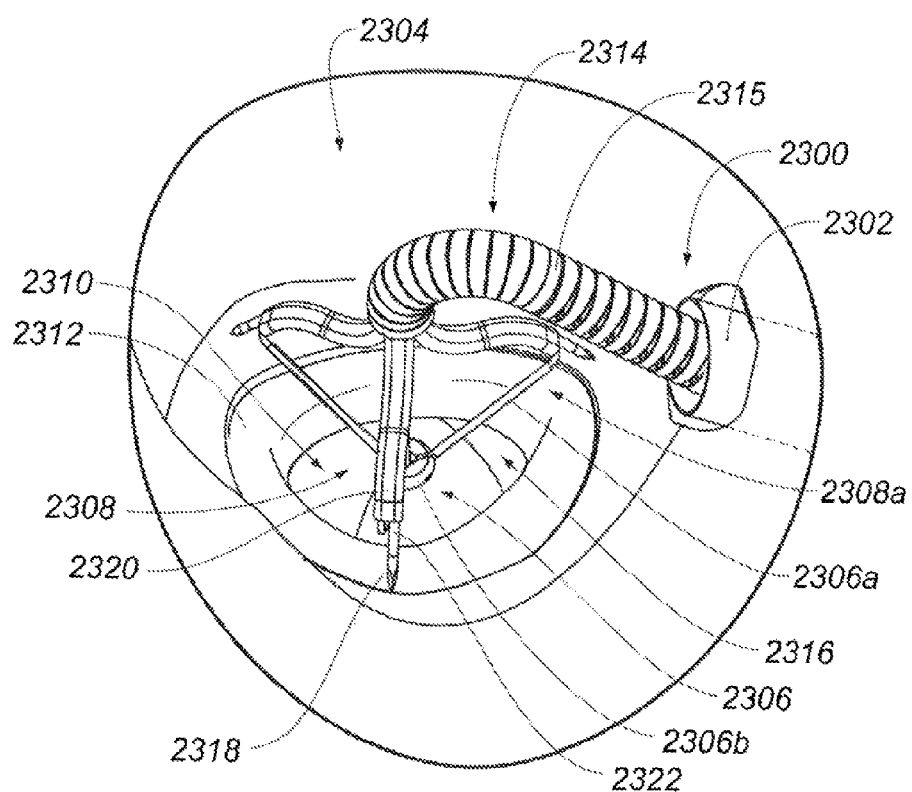
Figure 23L:
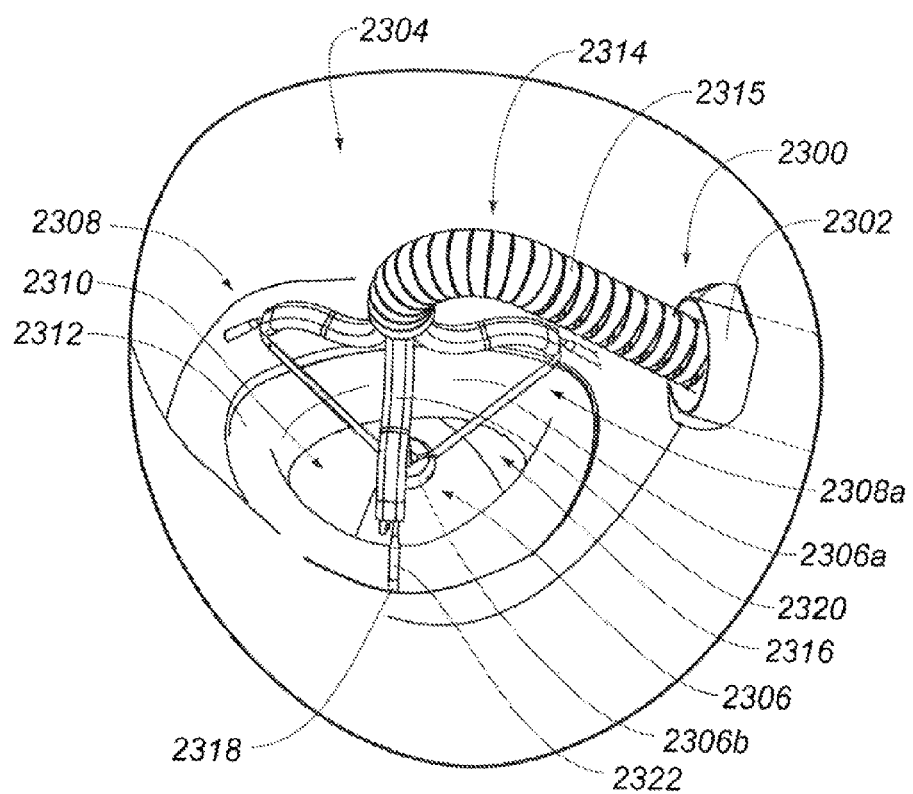
Figure 23M:
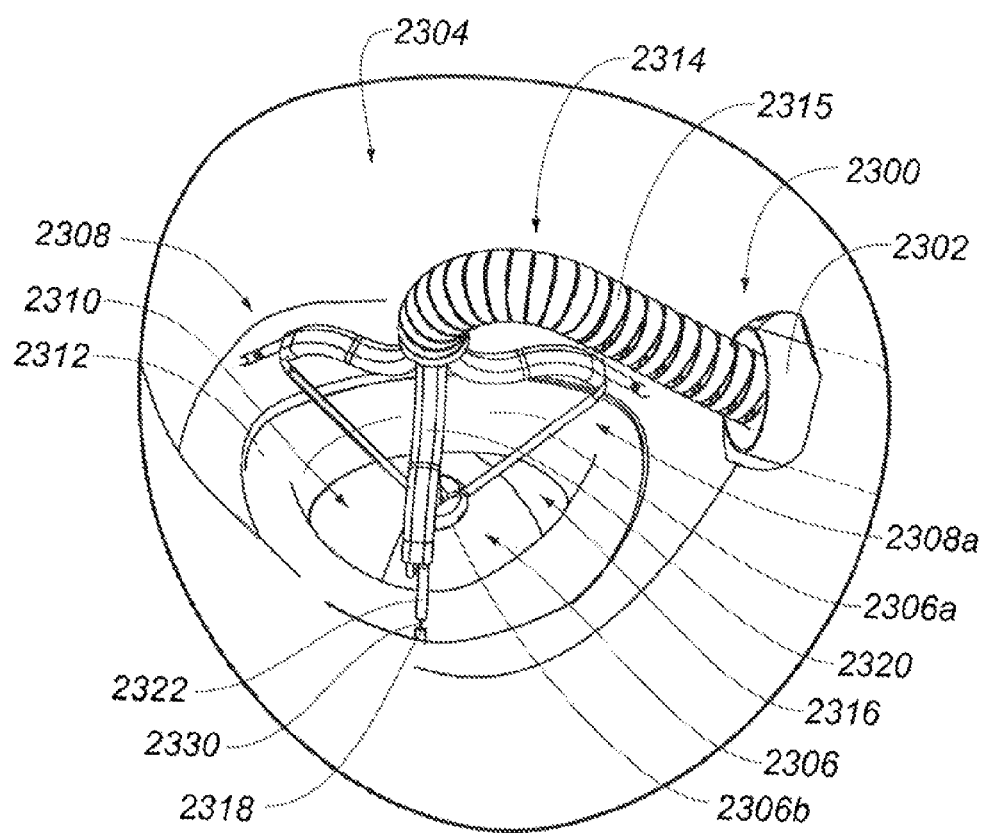
Figure 23N:
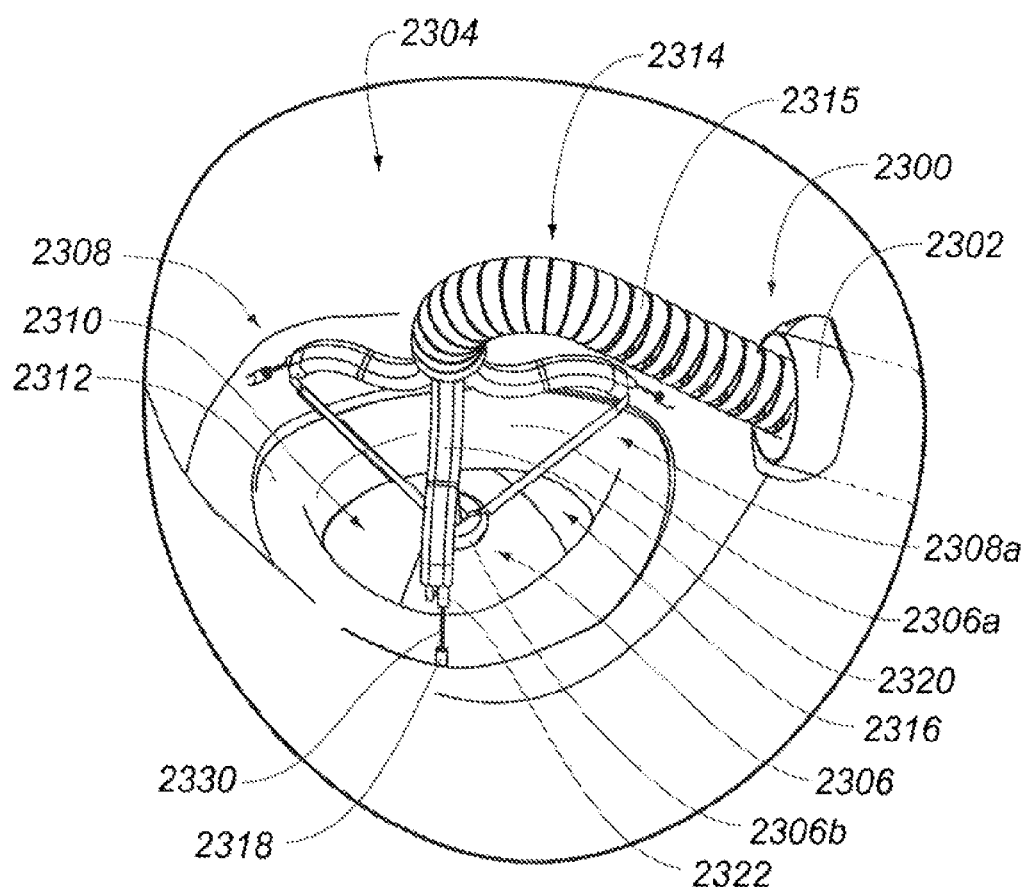
Figure 23O:
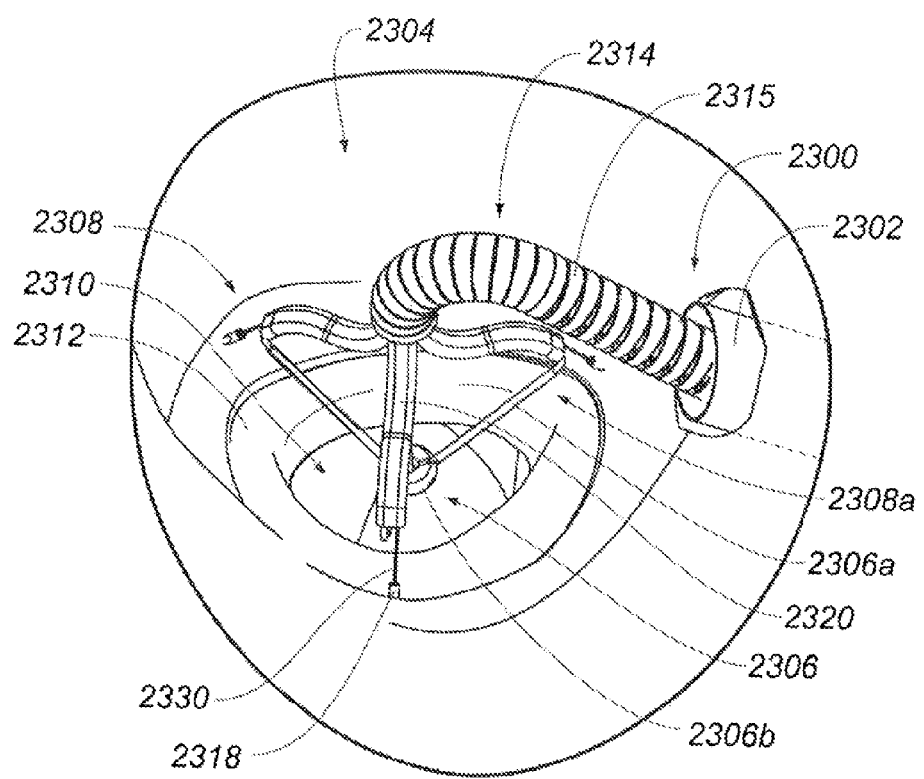
Figure 23P:
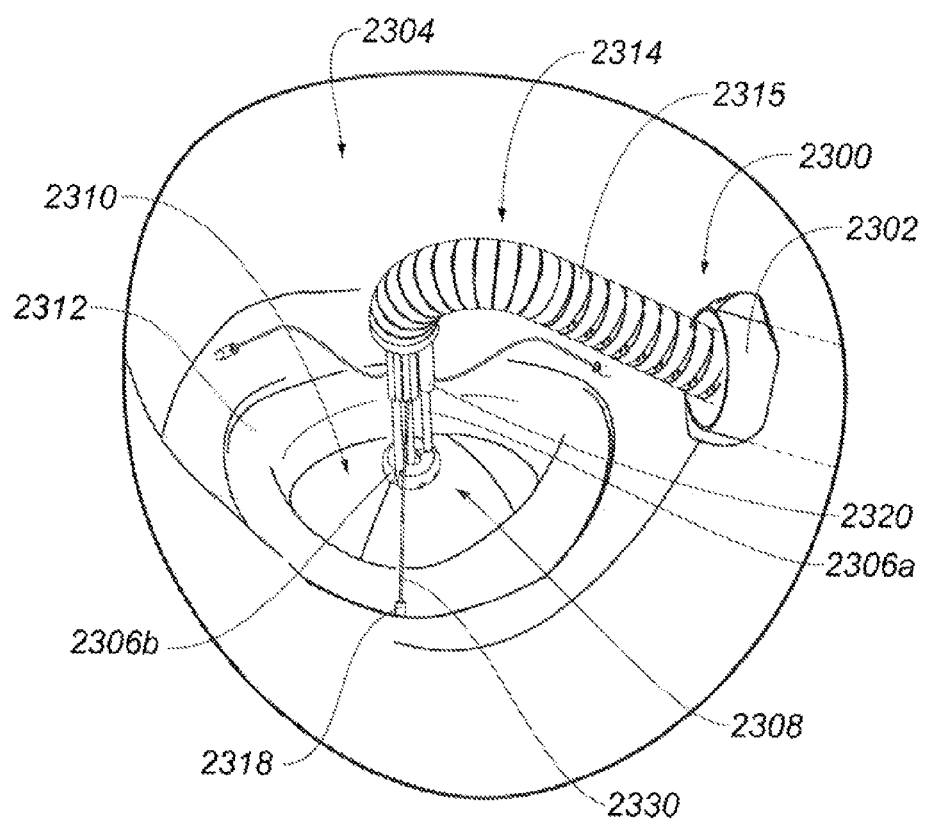
Figure 23Q:
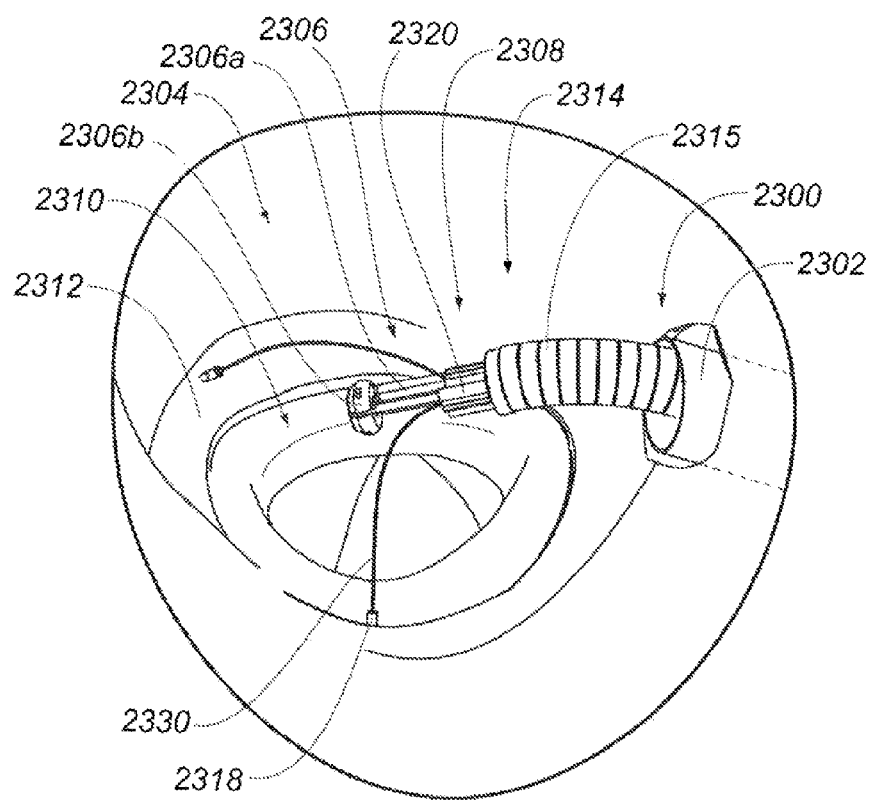
Figure 23R:
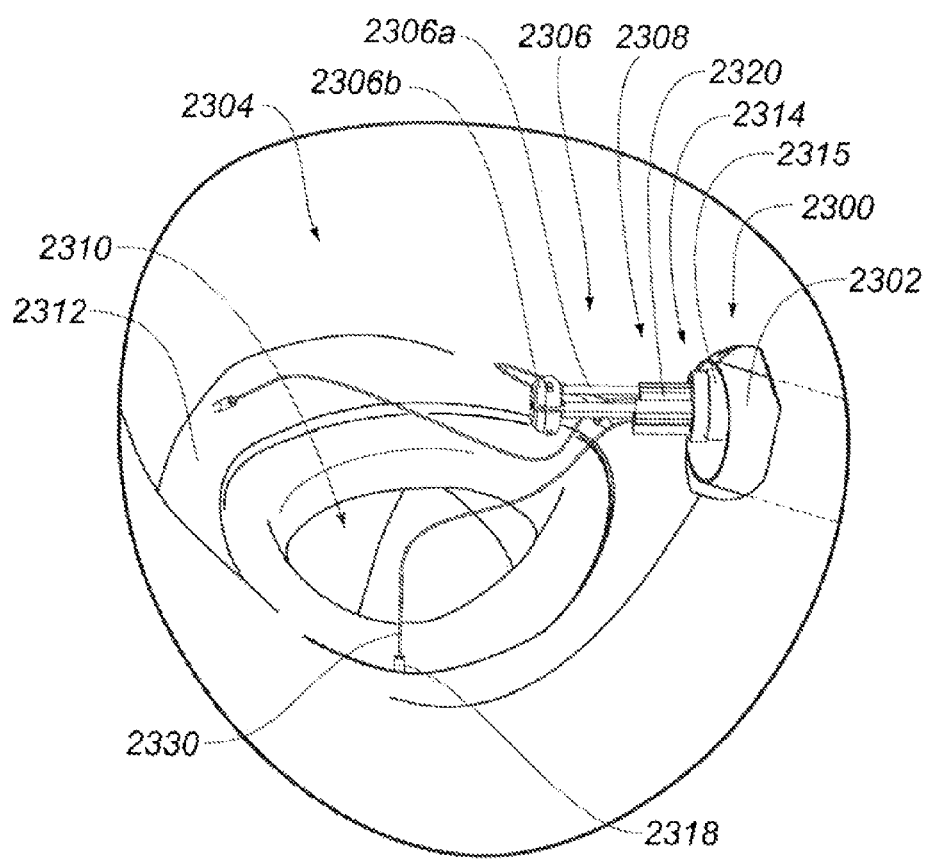
Figure 23S:
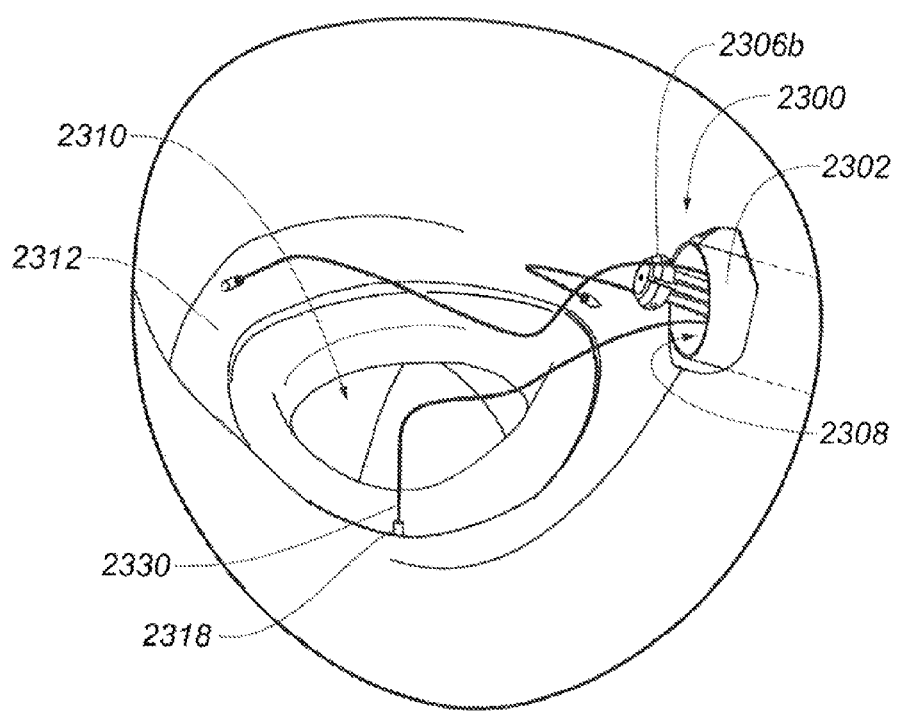
Figure 23T:
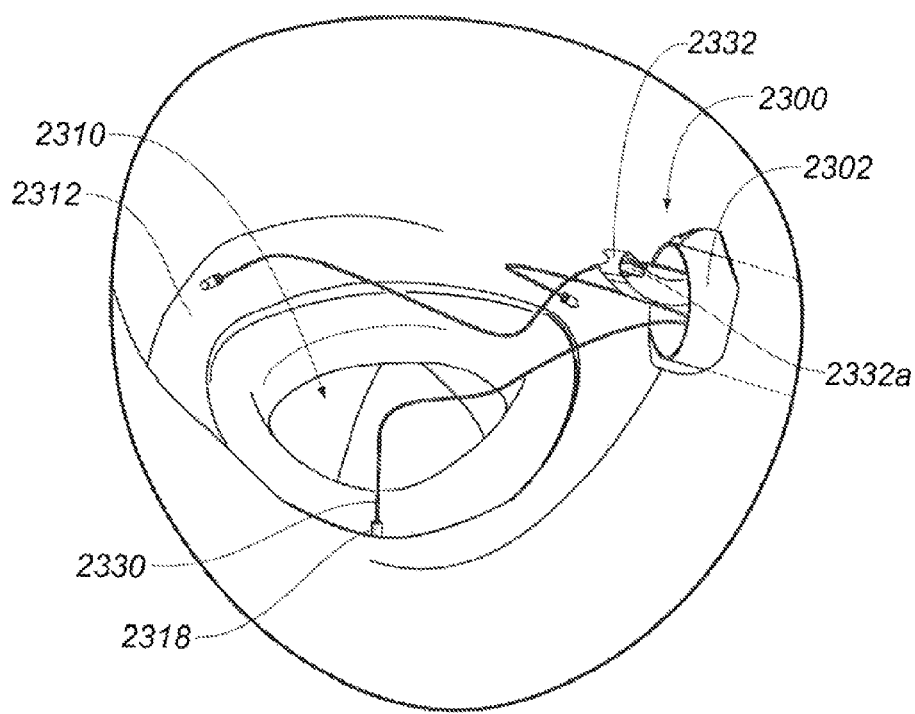

FIGS. 23A-23T sequentially show an implant procedure according to one illustrated embodiment. The implant procedure includes placement of tissue anchors via an anchor guide frame at selected locations in an annulus surrounding a mitral valve of a left atrium of a heart, and the securement of an implant member to the annulus via the embedded tissue anchors. Fluoroscopy, CT scanning, trans-esophageal echo (TEE) and/or other imaging or radiological techniques may be employed during all or part of the medical procedure, for example for guiding various catheters and/or locating the anchor guide frame for precisely placing or embedding the tissue anchors. For instance, TEE techniques may be employed to determine when to lock the implant member in position in the implantable configuration with the fasteners. Ultrasound may be employed before the medical procedure, or as part of the medical procedure, to determine a size of the mitral valve. Such information may be employed in selecting an appropriately sized implant member or in adjusting a size of the implant member. In some instances, the implant member may also be selected based on the actual locations of the tissue anchors.

In particular, FIG. 23A shows a distal end 2300 of a cardiac catheter 2302 advancing in a left atrium 2304 of a heart. The cardiac catheter 2302 may, for example, enter the heart via an inferior vena cava (not shown) or a superior vena cava (not shown), then enter the left atrium via a hole formed in a septum (not shown) of the heart. The cardiac catheter 2302 may be inserted using an introducer and guide wire, as is commonly known. A proximate end (not shown) of the cardiac catheter 2302 is outside of the bodily or accessible from outside of the body.

An engagement or locating member 2306 of an anchor guide frame 2308 is visible, extending out of the distal end 2300 of the cardiac catheter 2302. The engagement or locating member 2306 may have a number of arms 2306a (three illustrated, only one called out in FIGS. 23A-23T) and a hub 2306b. The hub 2306b may couple the arms 2306a. A mitral valve 2310 of the heart is also visible, including an annulus 2312, which is natural tissue that surrounds the mitral valve 2310. In use, the hub 2306b may be centered in the mitral valve 2310 in contact with the cusps or leaflets of the mitral valve 2310. The hub 2306b may take the form of an alignment member, for instance the alignment fin 1305 previously described with reference to FIG. 13.

FIG. 23B shows an anchoring catheter 2314 extending out of the cardiac catheter 2302. The anchoring catheter 2314 carries the anchor guide frame 2308. The anchoring catheter 2314 has a steerable portion 2316, which may be selectively steered from a location outside the body. The steerable portion 2316 may include an articulated section. The steerable portion 2316 may be steered mechanically, for example using wires (not shown in FIGS. 23A-23T) that extend through the anchoring catheter 2314 and which are attached to opposing portions of the articulated section. Alternatively, the steerable portion 2316 may be steered hydraulically, for example by controlling pressure in a number of lumens that extend through the anchoring catheter and which terminate in the articulated section. In addition to the engagement or locating member 2306, the anchor guide frame 2308 includes a number of anchor guides 2316 (three illustrated in FIGS. 23A-23T, only one called out) which guide tissue anchors 2318 (FIGS. 23J-23T) to selected locations on the annulus 2312. The anchor guides 2316 may each include a dual lumen outer tube 2320 (only one called out in FIGS. 23A-23T). One lumen may carry a respective one of the arms 2306a of the engagement or locating member 2306 for movement through the lumen. The other lumen may carry an inner or guide tube 2322, the tissue anchor 2318 and a guide line or guide wire 2330 (only one called out in FIGS. 23M-23T) for movement through the lumen. The inner or guide tube 2322 may be physically coupled to advance the tissue anchor 2318 through the lumen. Such a structure, and its use, were previously explained with reference to FIGS. 8C-8F.

FIG. 23C shows the anchoring catheter 2314 being steered to face the mitral valve 2310. FIG. 23D shows the anchoring catheter 2314 being advanced toward the mitral valve 2310.

FIG. 23E shows the engagement or locating member 2306 being extended from the anchoring catheter 2314 toward the mitral valve 2310. FIG. 23F shows the anchor guide frame 2308 beginning to open or expand, a slight bow in arms 2308a (only one called out in FIGS. 23F-23S) being visible in FIG. 23F. The anchor guide frame 2308 is opened once the engagement or locating member 2306 or hub 2306b is approximately in a desired position and orientation with respect to the mitral valve 2310. FIGS. 23G and 23H show the anchor guide frame 2308 opening or expanding further at successive intervals. FIG. 23I shows the anchor guide frame 2308 fully open or expanded. The anchor guide frame 2308 may move automatically into position because of the correspondence of the shape of the anchor guide frame 2308 with the anatomical structure of the valve. The anchor guide frame 2308 may be constructed so that the two rear most arms (as illustrated, one labeled 2306a and other one at the back of the figure) slide into the mitral commissures. Even if the anchor guide frame 2308 is deployed at the wrong angle, expanding the legs caused the anchor guide frame 2308 to rotate as the legs get pushed into the commissures. The mitral annulus is not perfectly round, and "corners" of the mitral annulus can advantageously be used to cause the anchor guide frame 2308 to automatically align with the mitral valve.

FIG. 23J shows the inner or guide tubes 2322 with tissue anchors 2318 beginning to protrude from the outer tubes 2320. FIGS. 23K and 23L show the inner or guide tubes 2322 with tissue anchors 2318 protruding further from the outer tubes 2320, at successive intervals, embedding the tissue anchors 2318 into the annulus 2312 of the mitral valve 2310. FIG. 23M shows the inner or guide tubes 2322 being withdrawn back into the outer tubes 2320, leaving the tissue anchors 2318 embedded in the tissue of the annulus 2312. The guide line or guide wire 2330 is first visible in FIG. 23M. As explained in reference to FIGS. 8C-8F, the guide line or guide wire 2330 may be pushed or held in place as the inner or guide tubes 2322 are withdrawn back into the outer tube 2320. FIG. 23N shows the inner or guide tubes 2322 almost fully withdrawn in the outer tube 2320, while FIG. 23O shows the inner or guide tubes 2322 fully withdrawn in the outer tube 2320.

FIG. 23P shows the anchor guide frame 2308 closing or collapsing. FIGS. 23Q and 23R shows the closed or collapsed anchor guide frame 2308 and anchoring catheter 2314 being positioned and oriented at successive intervals to be withdrawn into the cardiac catheter 2302. FIG. 23S shows the anchoring catheter 2314 withdrawn into the cardiac catheter 2302, leaving the tissue anchors 2318 and guide lines or guide wires 2330 behind in the left atrium 2304 of the heart. The anchoring catheter 2314 may then be removed, clearing the cardiac catheter 2302 for the next catheter, used to deliver an implant member. After the anchoring catheter 2314 is withdrawn from the cardiac catheter 2302, the guide lines or guide wires 2330 extend from the tissue anchors 2318 through the cardiac catheter 2302 at least to the proximate end thereof. Such allows an implant member to be coupled to the guide lines or guide wires 2330.

FIG. 23T shows a portion of an implant member 2332 being advanced into the left atrium 2304 through the cardiac catheter 2302. The implant member 2332 may take the form of an annuloplasty ring. As used herein and in the claims, a ring or annular structure may be an open structure (e.g., C-shaped) or a closed structure (O-shaped). The implant member 2332 has a number of guide line receivers 2332a (only one illustrated in FIG. 23T) that couple the implant member 2332 to a respective guide line or guide wire 2330. In the illustrated embodiment, the guide line receiver 2332a takes the form of a hole or aperture, sized to receive the guide line or guide wire 2330. Such allows the implant member 2332 to ride or otherwise advance along the guide lines or guide wires 2330 toward the tissue anchors 2318 embedded in the tissue around an orifice (e.g., mitral valve 2310). As previously explained in reference to FIGS. 5C and 5D, the implant member 2332 may include a relief (not illustrated in FIG. 23T) proximate the guide line receiver 2332a.

Figure 23U:
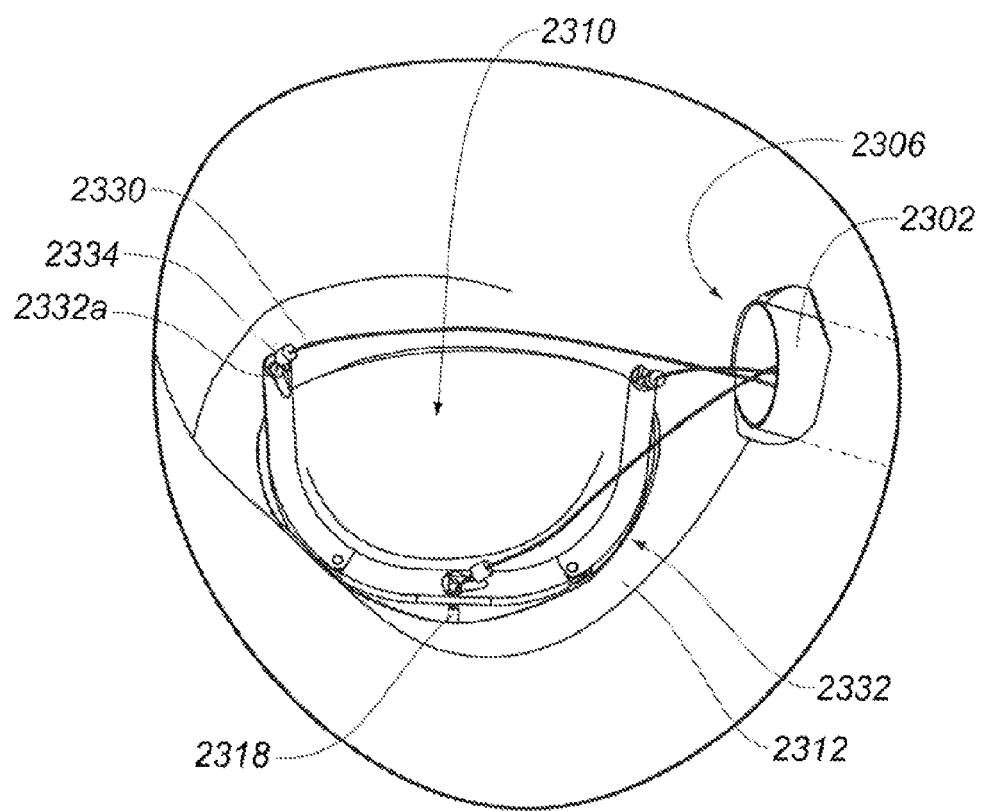

FIG. 23U shows the implant member 2332, guide lines or guide wires 2318 and fasteners 2334 (only one called out in FIG. 23U), according to one illustrated embodiment.

The implant member 2332 takes the form of an annuloplasty ring. Suitable segmented structures for the implant member 2332 have been previously described, for example in reference to FIGS. 19A-19D, 20A-20D, and 24A-24H although other implant member structures may be employed. The implant member 2332 is physically attached directly or coupled indirectly to the annulus 2312 of the mitral valve 2310. The implant member 2332 encompasses or surrounds a portion of the mitral valve 2310, for example angularly surrounding approximately half of the mitral valve 2310. In particular, the implant member 2332 is positioned and oriented to allow an anterior-posterior annular dimension of the mitral valve 2310 to be changed, for instance reduced. Such may cause the leaflets of the mitral valve 2310 to better coapt.

The implant member 2332 may ride or otherwise advance along the guide lines or guide wires 2318 to the locations on the annulus 2312 where the tissue anchors 2318 are embedded. A desired position and orientation is achieved due to the ability to precisely locate the tissue anchors 2318 using the anchor guide frame 2308. In particular, the engagement or locating member 2306 or hub 2306b and/or the anchor guides 2316 allows precise positioning and orientation of the embedding of the tissue anchors 1218, and hence the precise positioning and orientation of the implant member 2332.

In this example embodiment, fasteners 2334 are advanced along each of the guide lines or guide wires 2330 to secure the implant member 2332 to the annulus 2312. As previously described, the fasteners 2334 may take a variety of forms. For example, one-way clutch or cam mechanisms may allow the fasteners 2334 to advance in one direction along the guide lines or guide wires 2330 toward the tissue anchors 2318, but prevent or resist retreat of the fasteners 2334 along the guide lines or guide wires 2330 away from the tissue anchors 2318. After the fasteners 2334 are in place, excess portions of the guide lines or wires 2330 may be cut, broken or otherwise severed, and the excess portions removed from the body via the cardiac catheter 2302. Various embodiments of suitable cutting or severing mechanisms have been described above. Alternatively, a mechanism that facilitated a twisting or flexing of the guide lines or guide wires 2330 may be employed. The guide lines or guide wires 2330 are typically very fine, and may be easily severed with appropriate twisting or rotation about a longitudinal axis thereof. A small tail piece of guide line or guide wire 2330 may be left exposed beyond the fastener 2334 to allow later access, for example to replace the implant member 2332. In other example embodiments, fasteners 2334 are employed to couple directly with the embedded tissue anchors 2318 to secure implant member 2332 to the annulus 2312. In some example embodiments implant member 2332 and fasteners 2334 are combined into a unitary structure.

The various embodiments described above can be combined to provide further embodiments. All of any U.S. patents, U.S. patent application publications, U.S. patent applications, foreign patents, foreign patent applications and non-patent publications referred to in this specification and/or listed in the Application Data Sheet, including U.S. provisional patent application Ser. No. 61/278,232, filed Oct. 1, 2009, and commonly assigned U.S. nonprovisional application Ser. No. 12/894,912, filed on common date herewith and entitled "Medical Device, Kit and Method for Constricting Tissue or a Bodily Orifice, For Example, a Mitral Valve", are incorporated herein by reference, in their entirety. Aspects of the various embodiments can be modified, if necessary, to employ systems, circuits and concepts of the various patents, applications and publications to provide yet further embodiments.

These and other changes can be made in light of the above-detailed description. In general, in the following claims, the terms used should not be construed to limit the invention to the specific embodiments disclosed in the specification and the claims, but should be construed to include all medical treatment devices in accordance with the claims. Accordingly, the invention is not limited by the disclosure, but instead its scope is to be determined entirely by the following claims.

The invention claimed is:

1. A tissue anchor system for securing an implant member to tissue within a body during an implant procedure, the tissue anchor system comprising:
   a tissue anchor comprising plurality of elongated members, each of the elongated members comprising a first end, a second end and an intermediate portion positioned between the first and the second ends, wherein each of the second ends comprises a tip shaped to pierce the tissue, and the at least two of the elongated members are pivotably coupled together by a pivot member located at the intermediate portions with the elongated members crossing one another at the pivot member in a scissors configuration, where in response to movement of the first ends toward one another the second ends move from a first configuration in which the tips are spaced relatively apart from one another with a gap therebetween to a second configuration in which the tips are drawn together; and
   at least one coupler comprising a plurality of portions, at least a first portion of the at least one coupler physically coupled to at least a first one of the elongated members at a location on a portion of at least the first one of the elongated members extending between the pivot member and the first end of at least the first one of the elongated members, and at least a second portion of the at least one coupler physically coupled to at least a second one of the elongated members at a location on a portion of at least the second one of the elongated members extending between the pivot member and the first end of at least the second one of the elongated members, wherein the at least one coupler restricts pivoting of the at least two of the elongated members about an axis about which the intermediate portions of the at least two of the elongated members are pivotably coupled via an interaction between at least the first and the second portions of the coupler with: (a) at least a third portion of the coupler, (b) a portion of the implant member, or both.

2. The tissue anchor system of claim 1 wherein each elongated member of the at least two of the elongated members comprises an arcuate shaped portion as viewed along the axis about which the intermediate portions of the at least two of the elongated members are pivotably coupled.

3. The tissue anchor system of claim 1 wherein each elongated member of the at least two of the elongated members comprises a portion between the pivot member and the second end of the elongated member, and each portion between the pivot member and the second end of the elongated member of the at least two of the elongated members extends along a respective arcuate path as viewed along the axis about which the intermediate portions of the at least two of the elongated members are pivotably coupled.

4. The tissue anchor system of claim 3 wherein a terminus of each arcuate path is located at the tip of a respective elongated member of the at least two of the elongated members.

5. The tissue anchor system of claim 1 wherein each of the second ends comprises a barb.

6. The tissue anchor system of claim 1 wherein the at least one coupler is physically coupled to each of the at least two of the elongated members.

7. The tissue anchor system of claim 1 wherein at least the first portion of the at least one coupler and the first one of the elongated members form a unitary structure.

8. The tissue anchor system of claim 1 wherein an opening is provided in each of one or more of the elongated members, each opening sized to receive a guide line therethrough.

9. The tissue anchor system of claim 8 wherein each opening is provided in each respective one of the one or more of the elongated members at a respective location positioned relatively closer to the first end of the respective one of the one or more of the elongated members than to a location of the pivot member.

10. The tissue anchor system of claim 1 wherein the at least one coupler comprises an extension sized to be received within an opening provided in the implant member.

11. The tissue anchor system of claim 1 wherein each of the tissue anchor and the at least one coupler is sized to be delivered percutaneously to the tissue within the body during the implant procedure.

12. The tissue anchor system of claim 1 wherein a terminus of each elongated member of the at least two of the elongated members is located at the respective tip of the elongated member of the at least two of the elongated members.

13. The tissue anchor system of claim 1 wherein each elongated member of the at least two of the elongated members comprises a respective arcuate shaped portion, as viewed along the axis about which the intermediate portions of the at least two of the elongated members are pivotally coupled, that ends at the respective tip of the elongated member of the at least two of the elongated members.

14. The tissue anchor system of claim 1 wherein the intermediate portions of the at least two of the elongated members are pivotably coupled together by the pivot member to rotate the respective second ends of the at least two of the elongated members about the axis about which the intermediate portions of the at least two of the elongated members are pivotally coupled to move the respective second ends of the at least two of the elongated members towards or away from each other.

15. The tissue anchor system of claim 1 wherein the intermediate portions of the at least two of the elongated members are pivotably coupled together by the pivot member to rotate the respective tips of the at least two of the elongated members about the axis about which the intermediate portions of the at least two of the elongated members are pivotally coupled to move the respective tips of the at least two of the elongated members at least one of towards or away from each other.

16. The tissue anchor system of claim 1, further comprising:
   the implant member.

17. The tissue anchor system of claim 16 wherein the at least one coupler is distinct from the pivot member.

18. The tissue anchor system of claim 16 wherein the at least one coupler comprises at least two separate components, each of the at least two separate components coupled to a respective one of the at least two of the elongated members, each of the at least two separate components physically coupling the implant member when the tissue anchor is securely coupled to the implant member.

19. The tissue anchor system of claim 18 wherein both of the at least two separate components are received in a same opening provided in the implant member when the tissue anchor is securely coupled to the implant.

20. The tissue anchor system of claim 16 wherein the at least one coupler matingly couples the tissue anchor to the implant member when the tissue anchor is securely coupled to the implant member.

21. The tissue anchor system of claim 1 wherein the interaction includes an interaction with a fastener of the at least one coupler at least proximate the respective first end of each of the first one and the second one of the plurality of elongate members which restricts pivoting of the intermediate portions of the at least two of the elongated members.

22. The tissue anchor system of claim 1 wherein the respective first end, the respective second end and the respective intermediate portion of each elongated member of the at least two of the elongated members form part of a unitary member.

23. The tissue anchor system of claim 1 wherein each the at least two of the elongated members forms a respective prong.

* * * * *

UNITED STATES PATENT AND TRADEMARK OFFICE
CERTIFICATE OF CORRECTION

PATENT NO. : 8,940,002 B2  
APPLICATION NO. : 13/247380  
DATED : January 27, 2015  
INVENTOR(S) : Douglas Goertzen It is certified that error appears in the above-identified patent and that said Letters Patent is hereby corrected as shown below:

On the Title Page,

In the References Cited at Page 7, under the heading OTHER PUBLICATIONS, Line 5 (counted from the first text line after "OTHER PUBLICATIONS"), "Appl. No. 10/922,129, 17 pages." should read as --Appl. No. 10/622,129, 17 pages.--.

In the Claims,

Claim 1, at column 43, line 11, "comprising plurality" should read as --comprising a plurality--.

Signed and Sealed this  
Thirtieth Day of June, 2015

Michelle K. Lee  
*Director of the United States Patent and Trademark Office*